United States Patent
Faham et al.

(10) Patent No.: US 11,427,866 B2
(45) Date of Patent: Aug. 30, 2022

(54) METHOD OF IMPROVED SEQUENCING BY STRAND IDENTIFICATION

(71) Applicant: ACCURAGEN HOLDINGS LIMITED, Grand Cayman (KY)

(72) Inventors: Malek Faham, Burlingame, CA (US); Shengrong Lin, Fremont, CA (US); Ling Fung Tang, San Francisco, CA (US); Yontao Lu, Sunnyvale, CA (US); Zhaohui Sun, Albany, CA (US); Yingyu Wang, Mountain View, CA (US); Li Weng, Fremont, CA (US)

(73) Assignee: ACCURAGEN HOLDINGS LIMITED, Grand Cayman (KY)

(*) Notice: Subject to any disclaimer, the term of this patent is extended or adjusted under 35 U.S.C. 154(b) by 664 days.

(21) Appl. No.: 16/301,707

(22) PCT Filed: May 16, 2017

(86) PCT No.: PCT/US2017/032980
§ 371 (c)(1),
(2) Date: Nov. 14, 2018

(87) PCT Pub. No.: WO2017/201102
PCT Pub. Date: Nov. 23, 2017

(65) Prior Publication Data
US 2020/0010884 A1    Jan. 9, 2020

Related U.S. Application Data

(60) Provisional application No. 62/337,296, filed on May 16, 2016, provisional application No. 62/506,390, filed on May 15, 2017.

(51) Int. Cl.
*C12Q 1/6869*    (2018.01)
*C12Q 1/6827*    (2018.01)
*C12Q 1/6858*    (2018.01)
*C40B 50/06*    (2006.01)

(52) U.S. Cl.
CPC ......... *C12Q 1/6869* (2013.01); *C12Q 1/6827* (2013.01); *C12Q 1/6858* (2013.01); *C40B 50/06* (2013.01); *C12Q 2521/501* (2013.01); *C12Q 2535/139* (2013.01); *C12Q 2537/143* (2013.01)

(58) Field of Classification Search
CPC .. C12Q 1/6869; C12Q 1/6827; C12Q 1/6858; C12Q 2521/501; C12Q 2535/139; C12Q 2537/143; C40B 50/06; C12N 15/10
See application file for complete search history.

(56) References Cited

U.S. PATENT DOCUMENTS

| | | |
|---|---|---|
| 5,130,238 A | 7/1992 | Malek et al. |
| 5,234,809 A | 8/1993 | Boom et al. |
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |
| 5,492,808 A | 2/1996 | De et al. |
| 5,494,810 A | 2/1996 | Barany et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | De et al. |
| 5,648,212 A | 7/1997 | Albertsen et al. |
| 5,648,245 A | 7/1997 | Fire et al. |
| 5,691,454 A | 11/1997 | Albertsen et al. |
| 5,693,470 A | 12/1997 | De et al. |
| 5,693,536 A | 12/1997 | Vogelstein et al. |
| 5,705,365 A | 1/1998 | Ryder et al. |
| 5,705,628 A | 1/1998 | Hawkins et al. |
| 5,710,029 A | 1/1998 | Ryder et al. |
| 5,783,666 A | 7/1998 | Albertsen et al. |

(Continued)

FOREIGN PATENT DOCUMENTS

| AU | 9057901 A | 3/2002 |
|---|---|---|
| CN | 101985654 A | 3/2011 |

(Continued)

OTHER PUBLICATIONS

Amado, et al. Wild-type KRAS is required for panitumumab efficacy in patients with metastic colorectal cancer. Journal of Clinical Oncology. Apr. 1, 2008; 26(10);1626-1634.

(Continued)

*Primary Examiner* — Narayan K Bhat
(74) *Attorney, Agent, or Firm* — Wilson Sonsini Goodrich & Rosati

(57) ABSTRACT

In some aspects, the present disclosure provides methods for identifying sequence variants, as well as methods of determining copy number of a genetic locus in a sample. Systems and kits for performing methods of the disclosure, as well as compositions produced by or useful in methods of the disclosure are also provided. In some embodiments, methods comprise extending 3' ends of polynucleotides by adding one or more pre-determined nucleotides. In some embodiments, methods comprise use of a strand-tagging sequence.

16 Claims, 16 Drawing Sheets

(56) References Cited

U.S. PATENT DOCUMENTS

| | | |
|---|---|---|
| 5,807,692 A | 9/1998 | Kinzler et al. |
| 5,830,676 A | 11/1998 | Vogelstein et al. |
| 5,830,711 A | 11/1998 | Barany et al. |
| 5,837,443 A | 11/1998 | De et al. |
| 5,854,033 A | 12/1998 | Lizardi |
| 5,871,925 A | 2/1999 | De et al. |
| 5,871,968 A | 2/1999 | Kinzler et al. |
| 5,888,779 A | 3/1999 | Kacian et al. |
| 5,939,291 A | 8/1999 | Loewy et al. |
| 5,942,391 A | 8/1999 | Zhang et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,143,495 A | 11/2000 | Lizardi et al. |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,569,647 B1 | 5/2003 | Zhang et al. |
| 6,593,086 B2 | 7/2003 | Zhang |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,815,167 B2 | 11/2004 | Crothers et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield et al. |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | De et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,537,897 B2 | 5/2009 | Brenner et al. |
| 7,553,619 B2 | 6/2009 | Kumar et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski et al. |
| 8,048,629 B2 | 11/2011 | Gocke et al. |
| 8,209,130 B1 | 6/2012 | Kennedy et al. |
| 8,361,726 B2 | 1/2013 | Gocke et al. |
| 8,563,477 B2 | 10/2013 | Smith et al. |
| RE44,596 E | 11/2013 | Stroun et al. |
| 8,835,358 B2 | 9/2014 | Fodor et al. |
| 9,217,167 B2 | 12/2015 | Heller et al. |
| 9,260,753 B2 | 2/2016 | Xie et al. |
| 10,155,980 B2 | 12/2018 | Weng et al. |
| 10,443,087 B2 | 10/2019 | Rigatti et al. |
| 2002/0042061 A1 | 4/2002 | Yang et al. |
| 2002/0168645 A1 | 11/2002 | Taylor |
| 2003/0032024 A1 | 2/2003 | Lizardi |
| 2004/0058378 A1 | 3/2004 | Kong et al. |
| 2006/0228721 A1 | 10/2006 | Leamon et al. |
| 2007/0087362 A1 | 4/2007 | Church et al. |
| 2007/0099208 A1* | 5/2007 | Drmanac ............ C12Q 1/6806 435/6.12 |
| 2007/0134128 A1 | 6/2007 | Korlach |
| 2008/0021205 A1 | 1/2008 | Blau et al. |
| 2008/0039417 A1 | 2/2008 | Wang et al. |
| 2008/0160511 A1 | 7/2008 | Dawson et al. |
| 2009/0099041 A1 | 4/2009 | Church et al. |
| 2010/0075384 A1 | 3/2010 | Kong et al. |
| 2010/0115744 A1 | 5/2010 | Fong |
| 2010/0291548 A1 | 11/2010 | Sharaf et al. |
| 2010/0304989 A1 | 12/2010 | Von et al. |
| 2011/0003705 A1 | 1/2011 | Lowe et al. |
| 2011/0151438 A9 | 6/2011 | Nautiyal et al. |
| 2011/0237444 A1 | 9/2011 | Clancy et al. |
| 2011/0288284 A1 | 11/2011 | Makarov |
| 2011/0319299 A1 | 12/2011 | Osborne et al. |
| 2012/0115744 A1 | 5/2012 | Raymond et al. |
| 2012/0157326 A1 | 6/2012 | Tisi et al. |
| 2012/0164651 A1 | 6/2012 | Kazakov et al. |
| 2013/0217023 A1 | 8/2013 | Godwin et al. |
| 2013/0224740 A1 | 8/2013 | Thierry et al. |
| 2013/0244885 A1* | 9/2013 | Wang ................. C12Q 1/6804 506/2 |
| 2013/0331288 A1 | 12/2013 | Gunderson et al. |
| 2014/0051154 A1 | 2/2014 | Hyland et al. |
| 2014/0066317 A1 | 3/2014 | Talasaz et al. |
| 2014/0121116 A1 | 5/2014 | Richards et al. |
| 2014/0154683 A1 | 6/2014 | Vogelstein et al. |
| 2014/0221329 A1 | 8/2014 | Cronin et al. |
| 2014/0227705 A1 | 8/2014 | Vogelstein et al. |
| 2014/0234850 A1 | 8/2014 | Zhang et al. |
| 2014/0274740 A1 | 9/2014 | Srinivasan et al. |
| 2014/0295498 A1 | 10/2014 | Turner et al. |
| 2014/0296081 A1 | 10/2014 | Diehn et al. |
| 2014/0336236 A1 | 11/2014 | Cronin et al. |
| 2015/0031035 A1 | 1/2015 | Kvam et al. |
| 2015/0044687 A1 | 2/2015 | Schmitt et al. |
| 2015/0111789 A1 | 4/2015 | Betts et al. |
| 2015/0126376 A1 | 5/2015 | Bielas et al. |
| 2015/0133391 A1 | 5/2015 | De Vlaminick et al. |
| 2015/0141292 A1 | 5/2015 | Fodor et al. |
| 2015/0147815 A1 | 5/2015 | Babiarz et al. |
| 2015/0315636 A1 | 11/2015 | Nadeau et al. |
| 2015/0361492 A1 | 12/2015 | Vogelstein et al. |
| 2015/0366866 A1 | 12/2015 | Ali et al. |
| 2016/0040229 A1 | 2/2016 | Talasaz et al. |
| 2016/0145691 A1 | 5/2016 | Cronin et al. |
| 2016/0201135 A1 | 7/2016 | Cronin et al. |
| 2016/0304954 A1 | 10/2016 | Lin et al. |
| 2016/0319345 A1* | 11/2016 | Gnerre ................ C12N 15/1065 |
| 2017/0204456 A1 | 7/2017 | Nobile et al. |
| 2017/0362639 A1 | 12/2017 | Wilson |
| 2018/0298434 A1 | 10/2018 | Weng et al. |
| 2018/0363039 A1 | 12/2018 | Weng et al. |
| 2018/0363052 A1* | 12/2018 | Schmitt ................ C12Q 1/6806 |
| 2019/0119743 A1 | 4/2019 | Weng et al. |
| 2019/0241935 A1 | 8/2019 | Makarov et al. |
| 2020/0010883 A1 | 1/2020 | Weng et al. |
| 2020/0080141 A1 | 3/2020 | Weng et al. |

FOREIGN PATENT DOCUMENTS

| | | |
|---|---|---|
| CN | 102625850 A | 8/2012 |
| CN | 103717752 A | 4/2014 |
| CN | 104745679 A | 7/2015 |
| EP | 0684315 A1 | 11/1995 |

(56) References Cited

FOREIGN PATENT DOCUMENTS

| | | |
|---|---|---|
| EP | 0518650 B1 | 1/1997 |
| EP | 0390323 B1 | 12/1998 |
| EP | 0929694 A1 | 7/1999 |
| EP | 0580596 B1 | 7/2000 |
| EP | 0569527 B1 | 3/2001 |
| EP | 0730648 B1 | 8/2004 |
| EP | 2396430 B1 | 5/2013 |
| EP | 2828218 A1 | 1/2015 |
| JP | 2002503948 A | 2/2002 |
| JP | 2004512134 A | 4/2004 |
| JP | 2006516410 A | 7/2006 |
| JP | 2011505161 A | 2/2011 |
| JP | 2013143966 A | 7/2013 |
| JP | 2014138597 A | 7/2014 |
| WO | WO-9844151 A1 | 10/1998 |
| WO | WO-0049176 A1 | 8/2000 |
| WO | WO-0118230 A1 | 3/2001 |
| WO | WO-0120035 A2 | 3/2001 |
| WO | WO-0138580 A2 | 5/2001 |
| WO | WO-2007133703 A2 | 11/2007 |
| WO | WO-2007140417 A2 | 12/2007 |
| WO | WO-2007140417 A3 | 2/2008 |
| WO | WO-2007024653 A3 | 4/2008 |
| WO | WO-2008070352 A3 | 10/2008 |
| WO | WO-2013074632 A1 | 5/2013 |
| WO | WO-2013142389 A1 | 9/2013 |
| WO | WO-2013181170 A1 | 12/2013 |
| WO | WO-2013181276 A1 | 12/2013 |
| WO | WO-2014014498 A1 | 1/2014 |
| WO | WO-2014015084 A2 | 1/2014 |
| WO | WO-2014145128 A2 | 9/2014 |
| WO | WO-2015079042 A1 | 6/2015 |
| WO | WO-2015089333 A1 | 6/2015 |
| WO | WO-2015100427 A1 | 7/2015 |
| WO | WO-2016053638 A1 | 4/2016 |
| WO | WO-2017062863 A1 | 4/2017 |
| WO | WO-2017096322 A1 | 6/2017 |
| WO | WO-2017201102 A1 | 11/2017 |
| WO | WO-2017223366 A1 | 12/2017 |
| WO | WO-2018035170 A1 | 2/2018 |

OTHER PUBLICATIONS

Awuah, et al. Thermal inactivation kinetics of trypsin at aseptic processing temperatures. Journal of food process engineering 1993 v.16 No. 4 pp. 315-328 (abstract).

Blast. Basic local alignment search tool. Available at http://blast.ncbi.nlm.nih.gov/Blast.cgi. Accessed on Oct. 10, 2016.

Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.

Brenner. A cultivated taste for yeast. Genome Biol. 2000;1(1):REVIEWS103. Epub Apr. 27, 2000.

Brenner, C. Chemical genomics in yeast. Genome Biology. 2004; 5:240.

Brietbach et al. Direct Quantification of Cell-Free, Circulating DNA from Unpurified Plasma. PLoS One9(3):1-11 (2014).

Co-pending U.S. Appl. No. 16/368,355, filed Mar. 28, 2019.

Creating Standard Curves with Genomic DNA or Plasmid DNA Templates for Use in Quantitative PCR. Applied Biosystems 2003. Downloaded Oct. 17, 2017. URL:<http://www6.appliedbiosystems.com/support/tutorials/pdf/quant_pcr.pdf>.

Dawson, et al., Analysis of circulating tumor DNA to monitor metastatic breast cancer. The New England Journal of Medicine. Mar. 28, 2013. 368(13); 1199-1209.

Delcher, et al. Alignment of whole genomes. Nucleic Acids Research. Feb. 2, 1999; 27(11): 2369-2376.

Devonshire, Alison S. et al. Towards standardisation of cell-free DNA measurement in plasma: controls for extraction efficiency, fragment size bias and quantification, Analytical and Bioanalytical Chemistry, 406(26): 6499-6512 (2014).

Dicker, et al. The detection of TP53 mutations in chronic lymphocytic leukemia independently predicts rapid disease progression and is highly correlated with a complex aberrant karyotype. Leukemia. Jan. 2009; 23(1):117-124.

Eason, et al. Characterization of synthetic DNA barcodes in *Saccharomyces cerevisiae* genedeletion strains. Proc Natl Acad Sci U S A. Jul. 27, 2004; 101(30): 11046-11051.

Emboss. EMBOSS Water: Pairwise Sequence Alignment (Nucleotide). Available at http://www.ebi.ac.uk/Tools/psa/emboss_water/nucleotide.html. Accessed on Oct. 10, 2016.

Enari et al. A caspase-activated DNase that degrades DNA during apoptosis, and its inhibitor ICAD. Nature 391:43-50 (1998).

Florsheim, et al. Integrated Innate Mechanisms Involved in Airway Allergic Inflammation to the Serine Protease Subtilisin. J Immunol. May 15, 2015; 194(10): 4621-4630.

Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).

Freshney. Culture of Animal Cells: A Manual of Basic Technique and Specialized Applications. 6th Edition. 2010.

Giacona, et al. Cell-free DNA in human blood plasma: length measurements in patients with pancreatic cancer and healthy controls. Pancreas. Jul. 1998;17(1):89-97.

Giaever, et al. Chemogenomic profiling: identifying the functional interactions of small molecules in yeast. Proc Natl Acad Sci U S A. Jan. 20, 2004;101(3):793-8. Epub Jan. 12, 2004.

Guatelli et al. Isothermal, in vitro amplification of nucleic acids by a multienzyme reaction modeled after retroviral replication. PNAS USA 87(5):1874-1878 (1990).

Harkins, et al., Replicating fetal trisomy patient-like reference material for use in non-invasive prenatal screening tests. Sera Care. AMP 2015. Nov. 5-7, 2015.

Harlow, et al. Antibodies: A Laboratory manual. Cold Spring Harbor Laboratory. 1988.

Heinrich, et al. Kinase mutations and imatinib response in patients with metastatic gastrointestinal stromal tumor. Journal of Clinical Oncology. Dec. 1, 2003; 21 (23): 4342-4349.

Horizon Product Specification. cfDNA Reference Standard Set. 6068PSS-01(V-01). 2015.

Hussmann, et al. Reply to Schmitt et al.: Data-filtering schemes for avoiding double-counting in circle sequencing. PNAS. Apr. 22, 2014; 111(16).

Illumina. Genome Analyzer System. Available at http://support.illumina.com/content/dam/illumina-marketing/documents/products/datasheets/datasheet_genome_analyzeriix.pdf. Accessed on Oct. 10, 2016.

Jahr, et al. DNA fragments in the blood plasma of cancer patients: quantitations and evidence for their origin from apoptotic and necrotic cells. Cancer Res. Feb. 15, 2001;61(4):1659-65.

Jeffreys et al. DNA Enrichment by Allele-Specific Hybridization (DEASH): A Novel Method for Haplotyping and for Detecting Low-Frequency Base Substitutional Variants and Recombinant DNA Molecules. Genome Research 13:2316-2324 (2003).

Jiang et al. The Long and Short of Circulating Cell-Free DNA and the Ins and Outs of Molecular Diagnostics. Trends Genet 32(6):360-371 (2016).

Katayama, et al. Mechanisms of acquired crizotinib resistance in ALK-rearranged lung cancers. Sci. Transl Med. Feb. 8, 2012; 8(4).

Kent, W.J. Blat—The Blast-like alignment tool. Genome Research. 2012: 656-664.

Kumar, et al. Emerging technologies in yeast genomics. Nat Rev Genet. Apr. 2001;2(4):302-12.

Kurtz, et al. Versatile and open software for comparing large genomes. Biomed central. Jan. 30, 2004.

Landegren, U. Molecular mechanics of nucleic acid sequence amplification. Elsevier Science. Jun. 1993. 9(6). 199-204.

Langmead et al. Ultrafast and memory-efficient alignment of short DNA sequences to the human genome. Genome biology 10:R25 (10 pgs) (2009).

Larking, et al. Clustal W and Clustal X version 2.0. Bioinformatics applications note. 2007. 2947-2948; 23(21).

(56) References Cited

OTHER PUBLICATIONS

Lee, et al. Nucleic acid amplification technologies: application to disease diagnosis. Biotechniques books. 1997.
Li, et al. Fast and accurate long-read alignment with burrows-wheeler transform. Bioinformatics. Mar. 1, 2010;26(5):589-95.
Li et al. Fast and accurate short read alignment with burrows-wheeler transform. Bioinformatics 25(14):1754-1760 (2009).
Li, et al. Technical advance: Whole genome amplification of plasma-circulating DNA enables expanded screening for allelic imbalance in plasma. Journal of Molecular Diagnostics. Feb. 2006. 8(1); 22-30.
Lin, et al. Rolling Circle Enzymatic Replication of a Complex Multi-Crossover DNA Nanostructure. J Am Chem Soc. Nov. 21, 2007; 129(46): 14475-14481.
Lipman, et al. Rapid and sensitive protein similarity searches. Science. Mar. 22, 1985; 227(4693):1435-41.
Lizardi, et al. Exponential amplification of recombinant-RNA hybridization probes. Biotechnology. 1988. 6:1197-1202.
Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.
Lou et al., Supporting Information for "High-throughput DNA sequencing errors are reduced by orders of magnitude using circle sequencing," Proc Natl Acad Sci U S A., 110(49): 19872-7. doi: 10.1073/pnas.1319590110 (14 pages) (2013).
Lou et al. BioTechniques, pp. 1-14 [Support Information to Lou et al. BioTechniques 110(49) publication] (2013).
Maldonado, et al. Determinants of BRAF mutations in primary melanomas. Journal of the National Cancer Institute. Dec. 17, 2003; 95(24):1878-1880.
Matta, et al. Isolation and partial characterization of a thermostable extracellular protease of Bacillus polymyxa B-17. Int J Food Microbiol. Jul. 21, 1998;42(3):139-45 (abstract).
McLendon, et al. Survival analysis of presumptive prognostic markers among oligodendrogliomas. John Wiley & Sons. Oct. 15, 2005; 104(8):1693-1699.
McPherson, et al. eds. PCR 2: a practical approach. Oxford University Press. 1995.
Miller, et al. A simple salting out procedure for extracting DNA from human nucleated cells. Nucleic Acid Research. 1988; 16(3).
Misale, et al. Emergence of KRAS mutations and acquired resistance to anti-EGFR therapy in colorectal cancer. Nature. Jun. 13, 2012; 486(7404):532-536.
Neumann, et al., Frequency and type of KRAS mutations in routine diagnostic analysis of metastatic colorectal cancer. Pathol Res Pract. 2009;205(12):858-62.
Novocraft Technologies SDN BHD. NovoAlign. Available at http://www.novocraft.com/products/novoalign/. Accessed on Oct. 10, 2016.
Olivier, et al., TP53 mutations in human cancers: origins, consequences, and clinical use. Cold Spring Harb. Perspect Biology. 2010;1-17.
Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.
Paska et al. Effect of formalin, acetone, and RNAlater fixatives on tissue preservation and different size amplicons by real-time PCR from paraffin-embedded tissue. Diagn Mol Path 13(4): 234-240 (2004).
PCT/US2017/032980 International search Report and Written Opinion dated Oct. 19, 2017.
Pearson, et al. Improved Tools for Biological Sequence Comparison. Proc. Nat'l Acad. Sci. USA. 85 (1988): 2444-48.
Polidoros et al. Rolling circle amplification-RACE: a method for simultaneous isolation of 5' and 3' cDNA ends from amplified cDNA templates. BioTechniques 41:35-42 (2006).
Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.
Qiagen. How can QIAGEN Protease and Proteinase K be inactivated? Available at https://www.qiagen.com/ca/resources/faq?id=d24681d7-88e7-421a-84d9-27bfd5141103&lang=en. Accessed Apr. 11, 2018.
Remacle, et al. Substrate Cleavage Analysis of Furin and Related Proprotein Convertases—A Comparative Study. J Biol Chem. Jul. 25, 2008; 283(30): 20897-20906.
Samuels, et al. High Frequency of Mutations of the PIK3CA Gene in Human Cancers. Science Mag. Apr. 23, 2004; 304.
Schmitt, et al. Risks of double-counting in deep sequencing. PNAS. Apr. 22, 2014;111(16).
SeraCare and NIST Partner on Development of Circulating Tumor DNA Reference Standards for Diagnostics (Press Release). SeraCare Life Sciences, Inc. Jul. 14, 2016 (2 pages).
Seraseq(TM) ctDNA: A Breakthrough QC Technology. SeraCare Life Sciences, Inc. (2017) 6 pages.
Shaw, et al. Clinical Features and Outcome of Patients With Non-Small-Cell Lung Cancer Who Harbor EML4-ALK. Journal of Clinical Oncology. Sep. 10, 2009; 27(26):4247-4253.
Sievers, et al. Fast, Scalable generation of high-quality protein multiple sequence alignments using clustal omega. Molecular systems biology. 2011.
Sigma-Alorich. Protease from *Streptomyces griseus*. Available at https://www.sigmaaldrich.com/catalog/product/sigma/p6911?lang=en&region=US#. Accessed Apr. 11, 2018.
Slater, et al. Automated generation of heuristics for biological sequence comparison. BMC Bioinformatics. Feb. 15, 2005; 6(31): 1-11.
SOAP.Short Oligonucleotide Analysis Package. Available at http://soap.genomics.org.cn/. Accessed on Oct. 10, 2016.
SOURCEFORGE-Maq-Mapping-and-Assembly-with-Qualities. Available at http://maq.sourceforge.net/. Accessed on Oct. 10, 2016.
Spargo, et al. Detection of M. tuberculosis DNA using thermophilic strand displacement amplification. Mol Cell Probes. Aug. 1996;10(4):247-56.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology:Hybridization with nucleic acid probes. Elsevier Science. 1993.
U.S. Appl. No. 15/102,241 Office Action dated Oct. 12, 2018.
U.S. Appl. No. 15/800,558 Office Action dated Jan. 26, 2018.
U.S. Appl. No. 15/800,558 Final Office Action dated Jul. 6, 2018.
Walsh, et al. Chelex100 as a medium for simple extraction of DNA for PCR-based typing from forensic material. BioTechniques. 1991;10(4):506-513.
Wang, et al., Using ultra-sensitive next generation sequencing to dissect DNA damage-induced mutagenesis. Nature:Scientific Report. Dec. 2015.6:25310.
Wharam, et al. Specific detection of DNA and RNA targets using a novel isothermal nucleic acid amplification assay based on the formation of a three-way junction structure. Nucleic Acids Res. Jun. 1, 2001; 29(11): e54.
Widlak et al. Cleavage Preferences of the Apoptotic Endonuclease DFF40 (Caspase-activated DNase or Nuclease) on Naked DNA and Chromatin Substrates. The Journal of Biological Chemistry 275:8226-8232 (2000).
Winzeler, et al. Functional Characterization of the *S. cerevisiae* Genome by Gene Deletion and Parallel Analysis. Science. Aug. 6, 1999: vol. 285, Issue 5429, pp. 901-906.
Wang et al., DNA amplification method tolerant to sample degradation. Genome Research. 14(11):2357-2366 (2004).
Ali et al., Rolling circle amplification: a versatile tool for chemical biology, materials science and medicine. Chem Soc Rev 43(10): 3324-3341 (2014).
Dean et al., Comprehensive human genome amplification using multiple displacement amplification. Proc Natl Acad Sci USA 99(8): 5261-5266 (2002).

(56) References Cited

OTHER PUBLICATIONS

Hindson, et al. High-throughput droplet digital PCR system for absolute quantitation of DNA copy number. Analytical Chemistry. 83(22):8604-8610 (2011).
Newman, et al. An ultrasensitive method for quantitating circulating tumor DNA with broad patient coverage. Nat Med. May 2014;20(5):548-54. Epub Apr. 6, 2014.
Pinheiro et al., Evaluation of a Droplet Digital Polymerase Chain Reaction Format for DNA Copy Number Quantification. Analytical Chemistry. 84(2):1003-1011 (2012).
Schmitt et al., Detection of ultra-rare mutations by next-generation sequencing. PNAS. 109(36):14508-14523 (2012).
U.S. Appl. No. 16/434,941 Final Office Action dated Apr. 16, 2021.
U.S. Appl. No. 15/947,100 Office Action dated Oct. 24, 2019.
Yan, et al. Isothermal amplified detection of DNA and RNA. Mol Biosyst. May 2014;10(5):970-1003.
Beck, et al. Next generation sequencing of serum circulating nucleic acids from patients with invasive ductal breast cancer reveals differences to healthy and nonmalignant controls. Mol Cancer Res. Mar. 2010;8(3):335-42. doi: 10.1158/1541-7786.MCR-09-0314. Epub Mar. 9, 2010.
U.S. Appl. No. 16/689,018 Non-Final Office Action dated Dec. 24, 2021.
U.S. Appl. No. 16/945,553 Non-Final Office Action dated Dec. 22, 2021.

\* cited by examiner

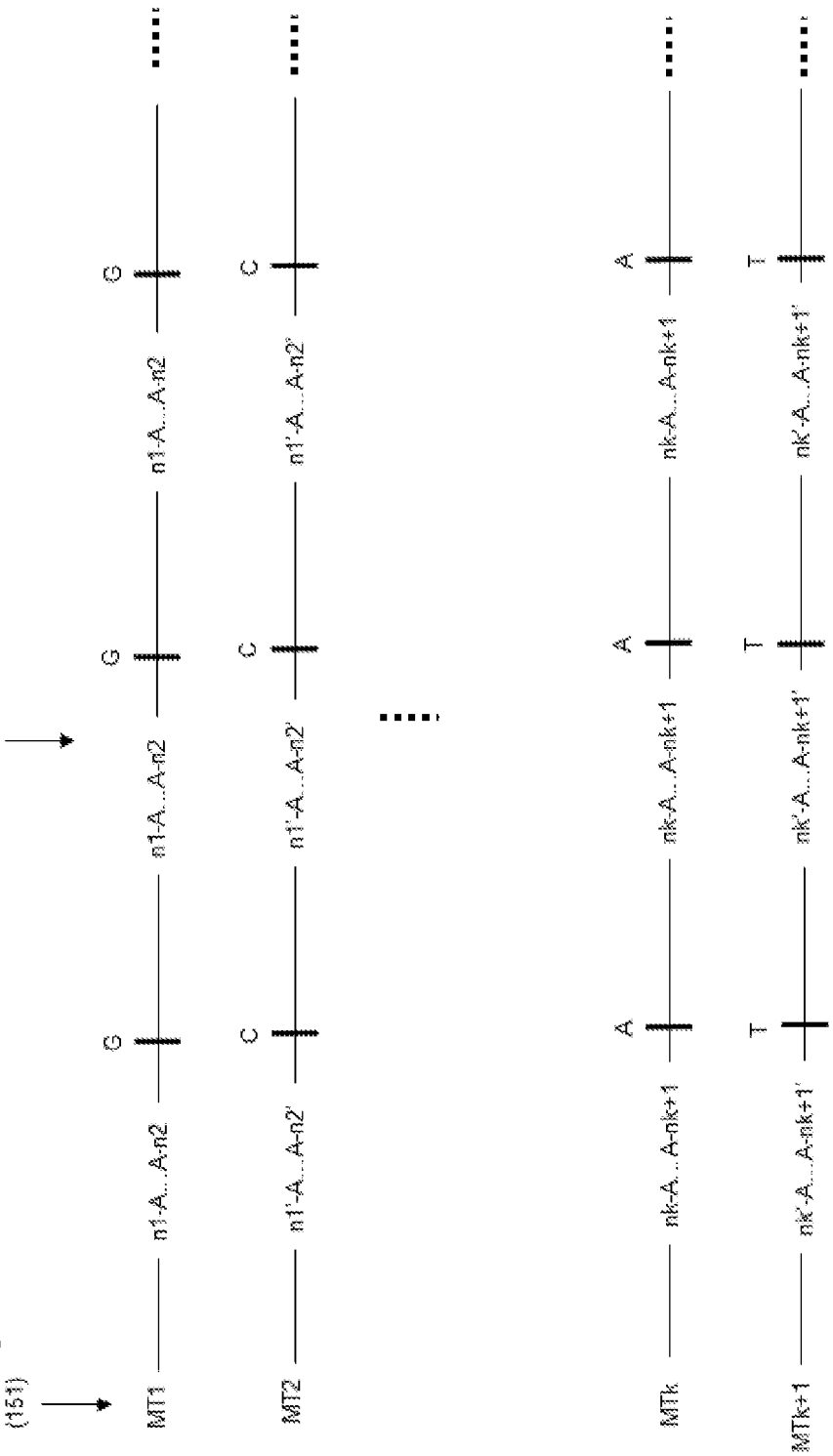

US 11,427,866 B2

METHOD OF IMPROVED SEQUENCING BY STRAND IDENTIFICATION

CROSS-REFERENCE

This application claims the benefit of U.S. Provisional Application No. 62/337,296, filed May 16, 2016, and U.S. Provisional Application No. 62/506,390, filed May 15, 2017, each of which is incorporated herein in its entirety by reference.

BACKGROUND

"Deep" sequencing of cell-free nucleic acids in clinical samples to identify rare variant sequences has made a significant impact on clinical science and medicine in general. However, distinguishing genuine sequence variants from sequencing, amplification and/or other processing errors remains a central challenge associated with these new sequence-based assays. This challenge has been addressed in several ways including, for example, by technology improvements that increase next-generation sequencing (NGS) read accuracy and by increasing the number of templates sequenced at each locus for improved error analysis. In spite of such advances, further improvements are still required, particularly in circumstances where the size of patient samples is severely limited.

SUMMARY

In view of the foregoing, there is a need for sequencing methods having higher accuracy and an ability to detect mutations that occur at lower frequency in a population. The present disclosure addresses these needs, and provides additional advantages as well. In some aspects, the present disclosure provides methods and compositions for identifying rare sequence variants at one or more genetic loci and for measuring copy number variations at one or more genetic loci. Aspects of the present disclosure are exemplified in a number of implementations and applications, some of which are summarized below and throughout the specification.

In one aspect, the present disclosure provides a method of identifying complementary strands in a nucleic acid sample comprising a plurality of double-stranded polynucleotides, each double-stranded polynucleotide of the plurality comprising a first complementary strand and a second complementary strand, each having a 5' end and a 3' end. In some embodiments, the method comprises: (a) modifying a polynucleotide sequence of at least one of a first complementary strand and a second complementary strand of individual double-stranded polynucleotides, wherein subsequent to the modifying, a first complementary strand and a second complementary strand originating from a common double-stranded polynucleotide are not perfectly complementary; (b) sequencing a plurality of first complementary strands and a plurality of second complementary strands, or amplification products thereof, to yield a plurality of sequencing reads; and (c) identifying from the plurality of sequencing reads, a given first complementary strand and a given second complementary strand as originating from a common double-stranded polynucleotide based on (i) sequences of the respective 3' ends and 5' ends and (ii) polynucleotide sequences of the corresponding complementary strands which are not perfectly complementary. In some embodiments, modifying a polynucleotide sequence comprises (i) extending a 3' end of at least one of the first complementary strand and the second complementary strand by adding one or more pre-determined nucleotides, (ii) attaching, for example by ligating, a polynucleotide having a predefined polynucleotide sequence to a 5' end, a 3' end, or both 5' and 3' ends of at least one of the first complementary strand and the second complementary strand, (iii) altering at least one nucleotide of the polynucleotide sequence, or (iv) a combination thereof. In some embodiments, modifying the polynucleotide sequence comprises altering at least one nucleotide of the polynucleotide sequence, and altering at least one nucleotide of the polynucleotide sequence is effected by treatment with bisulfite. In some embodiments, altering the at least one nucleotide changes the identity of the nucleotide.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each having a 5' end and a 3' end, the method comprising: modifying a polynucleotide sequence of at least one of a first complementary strand and a second complementary strand of individual double-stranded polynucleotides, wherein subsequent to modifying, a first complementary strand and a second complementary strand originating from a common double-stranded polynucleotide are not perfectly complementary; (b) sequencing a plurality of first complementary strands and a plurality of second complementary strands, or amplification products thereof, to yield a plurality of sequencing reads; (c) identifying from the plurality of sequencing reads, a given first complementary strand and a given second complementary strand as originating from a common double-stranded polynucleotide based on (i) sequences of the respective 3' end and 5' ends and (ii) polynucleotide sequences of the corresponding complementary strands which are not perfectly complementary; (d) comparing polynucleotide sequences of the given first complementary strand and the given second complementary strand of the common double-stranded polynucleotide; and (e) calling a sequence difference in the given first complementary strand relative to a reference sequence as the sequence variant only when the given second complementary strand originating from the common double-stranded polynucleotide comprises a complement of the sequence difference.

In one aspect, the present disclosure provides a method of identifying complementary strands in a nucleic acid sample comprising a plurality of double-stranded polynucleotides, each double-stranded polynucleotide of the plurality comprising a first complementary strand and a second complementary strand, each having a 5' end and a 3' end, the method comprising: (a) extending 3' ends of the complementary strands by adding one or more pre-determined nucleotides to produce extended polynucleotides; (b) amplifying the extended polynucleotides; (c) sequencing the amplified polynucleotides; and (d) identifying complementary strands as originating from the same double-stranded polynucleotide based on sequences of the respective 3' ends and 5' ends. In one aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each having a 5' end and a 3' end. In some embodiments, the method comprises (a) extending 3' ends of the complementary strands by adding one or more pre-determined nucleotides to produce extended polynucleotides; (b) amplifying the extended polynucleotides; (c) sequencing the amplified polynucleotides; (d) identifying complementary strands as originating from the same double-stranded polynucleotide based on sequences of the respective 3' ends and 5' ends; (e) comparing sequences of the first and second complementary strands of the same double-stranded polynucleotide based on the one or more predetermined nucleotides; and (f) calling a sequence difference in the first complementary strand relative to a reference sequence as the sequence variant only when the corresponding second complementary strand comprises a complement of the sequence difference. In some embodiments, the method further comprises identifying two first complementary strands or two second complementary strands as originating from different double-stranded polynucleotides based on extension of the respective 3' ends by a different number of predetermined nucleotides. In some embodiments, the method further comprises joining an adaptor polynucleotide to the 3' end of: (i) one or both strands of the double-stranded polynucleotides; or (ii) the extended polynucleotides; and optionally circularizing the adaptor-joined polynucleotides. In some embodiments, the step of amplifying the extended polynucleotides comprises extending a primer hybridized to the adaptor polynucleotide. In some embodiments, the extended polynucleotides are circularized to produce circularized polynucleotides prior to the amplifying step. In some embodiments, circularizing is effected by subjecting the extended polynucleotides to a ligation reaction. In some embodiments, the extended polynucleotides are denatured to form single-stranded polynucleotides prior to circularization. In some embodiments, amplification produces linear concatemers, and each concatemer comprises two or more copies of the corresponding circularized polynucleotide, or a complement thereof. In some embodiments, the method further comprises calling the sequence difference as the sequence variant only when (a) the same sequence difference occurs in more than one copy in the concatemer; and/or (b) the same sequence difference occurs in one or more double-stranded polynucleotides having different combinations of 3' ends and 5' ends. In some embodiments, the amplifying comprises rolling circle amplification. In some embodiments, the amplifying comprises extension of random primers. In some embodiments, the amplifying comprises extension of one or more primers specific to a target sequence. In some embodiments, the primers comprise a tag sequence, a sequencing primer binding sequence, or both. In some embodiments, the predetermined nucleotides are adenine nucleotides, and extending the 3' ends comprises adding one or more of the adenine nucleotides to the 3' ends.

In one aspect, the present disclosure provides systems for use in any of the methods described herein, including systems comprising units for carrying out one or more steps of a method. In one aspect, the disclosure provides a system for identifying a sequence variant in a nucleic acid sample comprising a plurality of double-stranded polynucleotides, each double-stranded polynucleotide of the plurality comprising a first and second complementary strand each having a 5' end and a 3' end. In some embodiments, the system comprises: (a) a computer configured to receive a user request to perform a detection reaction on a sample; (b) an amplification unit that performs a nucleic acid amplification reaction on the sample or a portion thereof in response to the user request, wherein the amplification reaction comprises the steps of: (i) extending 3' ends of the complementary strands by adding one or more predetermined nucleotides to produce extended polynucleotides; and (ii) amplifying the extended polynucleotides; (c) a sequencing unit that (i) generates sequencing reads for amplified polynucleotides; (ii) identifies differences between sequencing reads and a reference sequence; and (iii) calls a sequence difference in the first complementary strand relative to a reference sequence as the sequence variant only when the corresponding second complementary strand comprises a complement of the sequence difference; and (d) a report generator that sends a report to a recipient, wherein the report contains results of the sequence variant. In some embodiments, the amplification reaction further comprises joining an adaptor polynucleotide to the 3' end of: (i) one or both strands of the double-stranded polynucleotides; or (ii) the extended polynucleotides; and optionally circularizing the adaptor-joined polynucleotides. In some embodiments, the extended polynucleotides are circularized to produce circularized polynucleotides prior to the amplifying step. In some embodiments, the circularizing is effected by subjecting the extended polynucleotides to a ligation reaction. In some embodiments, the extended polynucleotides are denatured to form single-stranded polynucleotides prior to circularization. In some embodiments, amplification produces linear concatemers, and each concatemer comprises two or more copies of the corresponding circularized polynucleotide, or a complement thereof. In some embodiments, the sequencing unit calls the sequence difference as the sequence variant only when: (a) the same sequence difference occurs in more than one copy in the concatemer; and/or (b) the same sequence difference occurs in one or more double-stranded polynucleotides having different combinations of 3' ends and 5' ends. In some embodiments, the amplifying comprises rolling circle amplification. In some embodiments, the amplifying comprises extension of random primers. In some embodiments, the amplifying comprises extension of one or more primers specific to a target sequence. In some embodiments, the primers comprise a tag sequence, a sequencing primer binding sequence, or both. In some embodiments, the predetermined nucleotides are adenine nucleotides, and extending the 3' ends comprises adding one or more of the adenine nucleotides to the 3' ends.

In one aspect, the present disclosure provides computer readable media comprising codes that, upon execution by one or more processors, implement one or more of the methods described herein, such as a method of detecting a sequence variant in a nucleic acid sample comprising a plurality of double-stranded polynucleotides, each double-stranded polynucleotide of the plurality comprising a first and second complementary strand each having a 5' end and a 3' end. In some embodiments, the method implemented by execution of the computer readable medium comprises: (a) in response to a user request, performing a sequencing reaction to generate sequencing reads for polynucleotides amplified in an amplification reaction, wherein the amplification reaction comprises the steps of (i) extending 3' ends of the complementary strands by adding one or more predetermined nucleotides to produce extended polynucleotides; and (ii) amplifying the extended polynucleotides; (b) performing a sequencing analysis comprising the steps of: (i) identifying complementary strands as originating from the same double-stranded polynucleotide based on sequences of the respective 3' ends and 5' ends; (ii) comparing sequences of the first and second complementary strands of the same double-stranded polynucleotide based on the one or more predetermined nucleotides; and (iii) calling a sequence difference in the first complementary strand relative to a reference sequence as the sequence variant only when the corresponding second complementary strand comprises a complement of the sequence difference; and (c) generating a report that contains results for detection of the sequence variant.

In one aspect, the present disclosure provides a method of determining copy number of a genetic locus in a sample comprising a plurality of target polynucleotides comprising the genetic locus, each target polynucleotide having a 5' end and a 3' end. In some embodiments, the method comprises: (a) extending 3' ends of the target polynucleotides by adding one or more pre-determined nucleotides to produce extended polynucleotides; (b) amplifying the extended polynucleotides; (c) sequencing the amplified polynucleotides; (d) identifying one or more distinct polynucleotides comprising the genetic locus as originating from distinct target polynucleotides when respective sequences of one or more of the following are distinct: (i) a reference sequence to which the 5' end or a complement thereof aligns; (ii) a reference sequence to which the 3' end or a complement thereof aligns; and (iii) the 3' end extension; and (e) counting the number of distinct polynucleotides comprising the genetic locus to obtain the copy number of the genetic locus. In some embodiments, the step of amplifying comprises extension of primers having unique molecular tags, and further wherein distinct polynucleotides comprising the genetic locus are identified as originating from distinct target polynucleotides when respective sequences of one or more of the following are distinct: (i) a reference sequence to which the 5' end or a complement thereof aligns; (ii) a reference sequence to which the 3' end or a complement thereof aligns; (iii) the 3' end extension; and (iv) the unique molecular tag. In some embodiments, the target polynucleotides are double-stranded polynucleotides, and the method further comprises comparing sequences of first and second complementary strands of the same double-stranded polynucleotide based on the one or more predetermined nucleotides. In some embodiments, the method further comprises joining an adaptor polynucleotide to the 3' end of: (i) one or both strands of the double-stranded polynucleotides; or (ii) the extended polynucleotides; and optionally circularizing the adaptor-joined polynucleotides. In some embodiments, the extended polynucleotides are circularized to produce circularized polynucleotides prior to the amplifying step. In some embodiments, circularizing is effected by subjecting the extended polynucleotides to a ligation reaction. In some embodiments, the extended polynucleotides are denatured to form single-stranded polynucleotides prior to circularization. In some embodiments, amplification produces linear concatemers, and each concatemer comprises two or more copies of the corresponding circularized polynucleotide, or a complement thereof. In some embodiments, the amplifying comprises rolling circle amplification. In some embodiments, the amplifying comprises extension of random primers. In some embodiments, the amplifying comprises extension of one or more primers specific to a target sequence. In some embodiments, the primers comprise a tag sequence, a sequencing primer binding sequence, or both. In some embodiments, the predetermined nucleotides are adenine nucleotides, and extending the 3' ends comprises adding one or more of the adenine nucleotides to the 3' ends.

In one aspect, the present disclosure provides a method of identifying a sequence variant at a genetic locus in a sample comprising a plurality of target polynucleotides comprising the genetic locus, each target polynucleotide having a 5' end and a 3' end. In some embodiments, the method comprises: (a) extending 3' ends of the target polynucleotides by adding one or more pre-determined nucleotides to produce extended polynucleotides; (b) amplifying the extended polynucleotides; (c) sequencing the amplified polynucleotides to produce sequencing reads; (d) identifying a sequence change relative to a reference sequence by type of nucleotide change based on the sequence of the respective one or more pre-determined nucleotides; (e) determining the frequency of the identified type of sequence change at the genetic locus; and (f) calling the sequence change as the sequence variant when frequency of the type of nucleotide change is above a background level for that type of nucleotide change. In some embodiments, the method further comprises joining an adaptor polynucleotide to the 3' end of: (i) one or both strands of the double-stranded polynucleotides; or (ii) the extended polynucleotides; and optionally circularizing the adaptor-joined polynucleotides. In some embodiments, the extended polynucleotides are circularized to produce circularized polynucleotides prior to the amplifying step. In some embodiments, circularizing is effected by subjecting the extended polynucleotides to a ligation reaction. In some embodiments, the extended polynucleotides are denatured to form single-stranded polynucleotides prior to circularization. In some embodiments, amplification produces linear concatemers, and each concatemer comprises two or more copies of the corresponding circularized polynucleotide, or a complement thereof. In some embodiments, the amplifying comprises rolling circle amplification. In some embodiments, the amplifying comprises extension of random primers. In some embodiments, the amplifying comprises extension of one or more primers specific to a target sequence. In some embodiments, the primers comprise a tag sequence, a sequencing primer binding sequence, or both. In some embodiments, the predetermined nucleotides are adenine nucleotides, and extending the 3' ends comprises adding one or more of the adenine nucleotides to the 3' ends. In some embodiments, a C→T transition is distinguished from a G→A transition at the genetic locus.

In one aspect, the present disclosure provides compositions useful in or produced by one or more methods of the present disclosure. In one aspect, the present disclosure provides a nucleic acid composition comprising multiple pairs of single-stranded circularized polynucleotides; wherein (a) each strand of a pair consists of a first portion and a second portion; (b) the first portions of a pair share 100% sequence complementarity; (c) the second portions of a pair are not complementary; and (d) the second portions consist of 3' end extensions by one or more predetermined nucleotides. In some embodiments, the composition comprises at least 10000 pairs of single-stranded circularized polynucleotides (e.g. at least 50000, 100000, 500000, or 1000000 pairs), each of which comprises a distinct first portion sequence. In some embodiments, less than 50% (e.g. less than 25%, 10%, 5%, or 1%) of the single-stranded circularized polynucleotides are 100% complementary to another single-stranded circularized polynucleotide present in the composition. In some embodiments, the first portions are longer than the second portions. In some embodiments, the first portions comprise cell-free polynucleotides. In some embodiments, the pre-determined nucleotides consist of a single type of nucleotide. In some embodiments, the 3' end extensions consist of a single pre-determined nucleotide.

In one aspect, the present disclosure provides a method of identifying complementary strands of polynucleotides comprising the following steps: (a) extending by one or more predetermined nucleotides 3' ends of the polynucleotides; (b) amplifying individual strands of the extended polynucleotides; (c) sequencing the amplified individual strands of the extended polynucleotides; and (d) identifying extended polynucleotides having complementary strands by the identity of 3' sequences and/or 5' sequences adjacent to the one or more predetermined nucleotides. In some embodiments, the step of identifying includes identifying extended polynucleotides having complementary strands by numbers of the one or more predetermined nucleotides added to the 3' ends. In some embodiments, the step of amplifying includes ligating adaptors having primer binding sites or complements thereof to ends of the individual strands of the extended polynucleotides and performing a polymerase chain reaction. In some embodiments, the step of amplifying includes circularizing the individual strands of the polynucleotides to form single stranded polynucleotide circles, the one or more predetermined nucleotides defining a boundary between 3' sequences and 5' sequences of the polynucleotides in each single stranded polynucleotide circle, and amplifying by rolling circle replication the single stranded polynucleotide circles to form concatemers of the single stranded polynucleotide circles; and wherein the step of identifying includes identifying concatemers containing complementary strands of polynucleotides by the identity of 3' sequences and 5' sequences adjacent to the one or more predetermined nucleotides.

In one aspect, the present disclosure provides a method of identifying complementary strands of polynucleotides comprising the steps of: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying by rolling circle replication the single stranded polynucleotide circles to form concatemers of the single stranded polynucleotide circles; and (d) identifying concatemers containing complementary strands of polynucleotides by the identity of 3' sequences and 5' sequences adjacent to the one or more predetermined nucleotides. In some embodiments, the one or more predetermined nucleotides is a plurality of predetermined nucleotides. In some embodiments, the method further includes a step of attaching a unique molecular tag to each of the concatemers and identifying the concatemers containing complementary stands of the polynucleotides by the identity of the unique molecular tag and the identity of the 3' sequences and 5' sequences adjacent to the one or more predetermined nucleotides. In some embodiments, the step of identifying includes (a) annealing reverse primers to the concatemers and extending the reverse primers to form double stranded sequencing templates, and (b) sequencing the double stranded sequencing templates.

In one aspect, the present disclosure provides a method of identifying a sequence variant at a genetic locus in a sample comprising polynucleotides containing the genetic locus, wherein the method comprises the steps of: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying by rolling circle replication the single stranded polynucleotide circles to form concatemers; (d) sequencing the concatemers; (e) identifying pairs of concatemers containing complementary strands of polynucleotides by the identity of 3' sequences and 5' sequences adjacent to the one or more predetermined nucleotides; and (f) determining the sequence of the genetic locus from the sequences of the pairs of concatemers comprising complementary strands of the same polynucleotide. In some embodiments, the one or more predetermined nucleotides is a plurality of predetermined nucleotides. In some embodiments, the step of determining includes identifying a nucleotide at a sequence position of the genetic locus whenever nucleotides at that position or the reverse complement thereof are the same in each of the concatemers of the pair. In some embodiments, the step of determining includes identifying a nucleotide at a sequence position of the genetic locus whenever nucleotides at that position or the reverse complement thereof are the same in a majority of the concatemers of the pair.

In one aspect, the present disclosure provides a method of determining copy number of a genetic locus in a sample containing polynucleotides comprising the genetic locus, wherein the method comprises the following steps: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying the single stranded polynucleotide circles by rolling circle replication with primers each comprising a unique molecular tag to form concatemers each comprising a unique molecular tag; (d) sequencing the concatemers; (e) identifying pairs of concatemers containing complementary strands of polynucleotides by the identity of 3' sequences and 5' sequences adjacent to the one or more predetermined nucleotides; (f) determining the sequence of the genetic locus and molecular tags from the sequences of the pairs of concatemers comprising complementary strands of the same polynucleotide; and (g) counting a number of different molecular tags attached to polynucleotides comprising the genetic locus to obtain a copy number of the genetic locus.

In one aspect, the present disclosure provides a method of identifying a genetic variant at a genetic locus carried by polynucleotides by the following steps: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of the polynucleotides in each single stranded polynucleotide circle; (c) amplifying by rolling circle replication the single stranded polynucleotide circles to form concatemers of the single stranded polynucleotide circles; (d) identifying concatemers containing complementary strands of polynucleotides by the identity of 3' sequences and 5' sequences adjacent to the one or more predetermined nucleotides and identifying nucleotides of each strand at the genetic locus; and (e) determining a frequency of a nucleotide at the genetic locus from the identified concatemers for identifying the genetic variant. In some embodiments, the method is used for distinguishing a genetic variant from nucleotide damage, wherein the method further includes the step of calling the nucleotide whose frequency is determined as a genetic variant whenever the frequency of strands displaying the nucleotide exceeds by a predetermined factor a baseline frequency of strands having nucleotide damage that gives rise to the same nucleotide. In some embodiments, the predetermined factor corresponds to a confidence level of at least ninety-five percent. In some embodiments, a C→T transition is distinguished from a G→A transition at the genetic locus.

In an aspect, the disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and a 3' end, the method comprising: (a) providing a plurality of circularized single-stranded polynucleotides in a plurality of reaction volumes, wherein an individual reaction volume contains only one circularized single-stranded polynucleotide formed by linking the 5' end and the 3' end of a first complementary strand or those of a second complementary strand, wherein the one circularized single-stranded polynucleotide has a junction sequence formed by the linking, and wherein a polynucleotide sequence of at least one of a first complementary strand and a second complementary strand has been modified such that a first complementary strand and a second complementary strand originating from a common double-stranded polynucleotide are not perfectly complementary; (b) sequencing the plurality of circularized single-stranded polynucleotides, or amplification products thereof, to yield a plurality of sequencing reads; (c) identifying from the plurality of sequencing reads, a given first complementary strand and a given second complementary strand as originating from a common double-stranded polynucleotide if (i) the given first complementary strand comprises a junction sequence that is complementary to that of the given second complementary strand and (ii) the polynucleotide sequences of the corresponding complementary strands are not perfectly complementary; and (d) calling a sequence difference in the given first complementary strand relative to a reference sequence as the sequence variant only when the corresponding given second complementary strand which originates from the common double-stranded polynucleotide comprises a complement of the sequence difference. In some embodiments, the polynucleotide sequence of at least one of a first complementary strand and a second complementary strand originating from a common double-stranded polynucleotide is modified by (i) extending a 3' end of at least one of the first complementary strand and the second complementary strand by adding one or more pre-determined nucleotides, (ii) attaching, for example by ligating, a polynucleotide having a predefined polynucleotide sequence to a 5' end, a 3' end, or both 5' and 3' ends of at least one of the first complementary strand and the second complementary strand, (iii) altering at least one nucleotide of the polynucleotide sequence, or (iv) a combination thereof. In some embodiments, modifying the polynucleotide sequence comprises altering at least one nucleotide of the polynucleotide sequence, and altering at least one nucleotide of the polynucleotide sequence is effected by treatment with bisulfite, as previously described.

In an aspect, the disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and a 3' end, the method comprising: (a) providing a plurality of circularized single-stranded polynucleotides in a plurality of reaction volumes, wherein an individual reaction volume contains only one circularized single-stranded polynucleotide formed by linking the 5' end and the 3' end of a first complementary strand or those of a second complementary strand, wherein the one circularized single-stranded polynucleotide has a junction sequence formed by the linking; (b) in a plurality of reaction volumes, conducting a primer extension reaction using a pair of forward and reverse strand-tagging primers, at least one of the pair comprising a strand identifying tag, to yield a plurality of strand-tagged, linear double-stranded concatemers, each comprising a strand identifying tag sequence, wherein the strand identifying tag sequence is unique to a circularized single-stranded polynucleotide in a given reaction volume; (c) sequencing the plurality of strand-tagged, linear double-stranded concatemers to yield a plurality of sequencing reads; (d) identifying from the plurality of sequencing reads, a given first complementary strand and a given second complementary strand as originating from a common double-stranded polynucleotide if (i) the given first complementary strand comprises a junction sequence that is complementary to that of the given second complementary strand, and (ii) the given first complementary strand comprises a strand identifying tag sequence that is different from that of the second complementary strand; and (e) calling a sequence difference in the given first complementary strand relative to a reference sequence as the sequence variant only when the corresponding given second complementary strand which originates from the common double-stranded polynucleotide comprises a complement of the sequence difference. In some embodiments, in (a), linking the 5' end and the 3' end of the first complementary strand or those of the second complementary strand comprises ligating the 5' end to the 3' end.

In some embodiments, the primer extension reaction of (b) comprises rolling circle replication, polymerase chain reaction, or a combination thereof. In some embodiments, the primer extension reaction of (b) comprises: rolling circle replication using a pair of forward and reverse amplification primers to yield a plurality of linear double-stranded concatemers comprising a common sequence, wherein each of the pair of forward and reverse amplification primers comprises (i) a target specific sequence at a 3' end complementary to a circular single-stranded polynucleotide sequence, or a complement thereof, and (ii) a common sequence at a 5' end not complementary to the circular single-stranded polynucleotide sequence, or a complement thereof, and polymerase chain reaction using the pair of forward and reverse strand-tagging primers to yield the plurality of strand-tagged, linear double-stranded concatemers, wherein (i) each of the pair of forward and reverse strand-tagging primers comprises the common sequence at a 3' end which hybridizes to an individual strand of a linear double-stranded concatemer comprising the common sequence and (ii) at least one of the pair of forward and reverse strand-tagging primers comprises the strand identifying tag at a 5' end. In some embodiments, the primer extension reaction of (b) comprises rolling circle replication using the pair of forward and reverse strand-tagging primers to yield the plurality of strand-tagged, linear double-stranded concatemers, wherein (i) each of the pair of forward and reverse strand-tagging primers comprises a target specific sequence at a 3' end complementary to a circular single-stranded polynucleotide sequence, or a complement thereof, and (ii) a common sequence at a 5' end not complementary to the circular single-stranded polynucleotide sequence, or a complement thereof. In some embodiments, the primer extension reaction of (b) further comprises polymerase chain reaction using a pair of forward and reverse amplification primers to yield amplification product comprising additional strand-tagged, linear double-stranded concatemers, wherein each of the pair of forward and reverse amplification primers comprises the common sequence at a 3' end which hybridizes to an individual strand of a strand-tagged, double-stranded linear concatemer.

In some embodiments, at least one of the pair of forward and reverse strand-tagging primers further comprises an amplification primer binding sequence, a sequencing primer binding sequence, or a combination thereof. In some embodiments, at least one of the pair of forward and reverse amplification primers further comprises an amplification primer binding sequence, a sequencing primer binding sequence, or a combination thereof.

In some embodiments, an individual strand-tagged, linear double-stranded concatemer of the plurality comprises two or more copies of the corresponding circularized single-stranded polynucleotide. In some embodiments, the method further comprises comprising calling the sequence difference as the sequence variant only when the same sequence difference occurs in at least one copy in the linear concatemer.

In some embodiments, the method further comprises calling the sequence difference as the sequence variant only when the same sequence difference occurs in at least two double-stranded polynucleotides having different combinations of 3' ends and 5' ends.

In some embodiments, the plurality of double-stranded polynucleotides comprises cell-free polynucleotides. In some embodiments, the plurality of double-stranded polynucleotides comprises cell-free DNA. In some embodiments, the plurality of double-stranded polynucleotides comprises circulating tumor DNA.

In some embodiments, the plurality of reaction volumes comprises a plurality of PCR tubes, microfluidic chambers, or droplets.

In an aspect, the present disclosure provides a method of identifying complementary strands in a nucleic acid sample comprising a plurality of a double-stranded polynucleotides, each double-stranded polynucleotide of the plurality comprising a first complementary strand and a second complementary strand, each strand having a 5' end and 3' end, the method comprising: (a) providing a plurality of single-stranded polynucleotides in a plurality of reaction volumes, wherein an individual reaction volume contains only one single-stranded polynucleotide comprising a first complementary strand or a second complementary strand of a double-stranded polynucleotide; (b) in a plurality of reaction volumes, modifying a polynucleotide sequence of a single-stranded polynucleotide, wherein subsequent to the modifying, a first complementary strand and a second complementary strand originating from a common double-stranded polynucleotide are not perfectly complementary; (c) sequencing single-stranded polynucleotides, or amplification products thereof, to yield a plurality of sequencing reads; and (d) identifying from the plurality of sequencing reads, a given first complementary strand and a given second complementary strand as originating from a common double-stranded polynucleotide based on (i) sequences of the respective 3' ends and 5' ends and (ii) polynucleotide sequences of the corresponding complementary strands which are not perfectly complementary.

In an aspect, the present disclosure provides a method of identifying complementary strands in a nucleic acid sample comprising a plurality of a double-stranded polynucleotides, each double-stranded polynucleotide of the plurality comprising a first complementary strand and a second complementary strand, each strand having a 5' end and 3' end, the method comprising: (a) providing a plurality of single-stranded polynucleotides in a plurality of reaction volumes, wherein an individual reaction volume contains only one single-stranded polynucleotide comprising a first complementary strand or a second complementary strand of a double-stranded polynucleotide of the nucleic acid sample, wherein a polynucleotide sequence of the only one single-stranded polynucleotide has been modified such that a first complementary strand and a second complementary strand originating from a common double-stranded polynucleotide are no longer perfectly complementary; (b) sequencing a plurality of single-stranded polynucleotides, or amplification products thereof, to yield a plurality of sequencing reads; and (c) identifying from the plurality of sequencing reads, a given first complementary strand and a given second complementary strand as originating from a common double-stranded polynucleotide based on (i) sequences of the respective 3' ends and 5' ends and (ii) polynucleotide sequences of the corresponding complementary strands which are not perfectly complementary.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and 3' end, the method comprising: (a) providing a plurality of single-stranded polynucleotides in a plurality of reaction volumes, wherein an individual reaction volume contains only one single-stranded polynucleotide comprising a first complementary strand or a second complementary strand of a double-stranded polynucleotide; (b) in a plurality of reaction volumes, modifying a polynucleotide sequence of a single-stranded polynucleotide, wherein subsequent to the modifying, a first complementary strand and a second complementary strand originating from a common double-stranded polynucleotide are not perfectly complementary; (c) sequencing single-stranded polynucleotides, or amplification products thereof, to yield a plurality of sequencing reads; (d) identifying from the plurality of sequencing reads, a given first complementary strand and a given second complementary strand as originating from a common double-stranded polynucleotide based on (i) sequences of the respective 3' ends and 5' ends and (ii) polynucleotide sequences of the corresponding complementary strands which are not perfectly complementary; (e) comparing polynucleotide sequences of the given first complementary strand and the given second complementary strand originating from the common double-stranded polynucleotide; and (f) calling a sequence difference in the given first complementary strand relative to a reference sequence as the sequence variant only when the corresponding given second complementary strand originating from the common double-stranded polynucleotide comprises a complement of the sequence difference.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and 3' end, the method comprising: (a) providing a plurality of single-stranded polynucleotides in a plurality of reaction volumes, wherein an individual reaction volume contains only one single-stranded polynucleotide comprising a first complementary strand or a second complementary strand of a double-stranded polynucleotide, wherein a polynucleotide sequence of the only one single-stranded polynucleotide has been modified such that a first complementary strand and a second complementary strand originating from a common double-stranded polynucleotide are no longer perfectly complementary; (b) sequencing a plurality of single-stranded polynucleotides, or amplification products thereof, to yield a plurality of sequencing reads; (c) identifying from the plurality of sequencing reads, a given first complementary strand a given second complementary strand as originating from a common double-stranded polynucleotide based on (i) sequences of the respective 3' ends and 5' ends and (ii) polynucleotide sequences of the corresponding complementary strands which are not perfectly complementary; (d) comparing polynucleotide sequences of the given first complementary strand and the given second complementary strand originating from the common double-stranded polynucleotide; and (e) calling a sequence difference in the given first complementary strand relative to a reference sequence as the sequence variant only when the corresponding given second complementary strand originating from the common double-stranded polynucleotide comprises a complement of the sequence difference.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and 3' end, the method comprising: (a) providing a plurality of single-stranded polynucleotides in a plurality of reaction volumes, wherein an individual reaction volume contains only one single-stranded polynucleotide comprising a first complementary strand or a second complementary strand of a double-stranded polynucleotide; (b) in a plurality of reaction volumes, conducting an amplification reaction to yield a plurality of amplification products, wherein the amplification reaction comprises: (i) for a given reaction volume, first circularizing the single-stranded polynucleotide to yield a circularized single-stranded polynucleotide, wherein the circularized single-stranded polynucleotide has a junction sequence formed by linking the 5' end to the 3' end of the single-stranded polynucleotide, and second, conducting a primer extension reaction using a pair of forward and reverse strand-tagging primers, at least one of the pair comprising a strand identifying tag, to yield the plurality of amplification products, wherein the amplification products comprise strand-tagged, linear double-stranded concatemers, each comprising a strand identifying tag sequence, wherein the strand identifying tag sequence is unique to the single-stranded polynucleotide in the given reaction volume; or (ii) for a given reaction volume, first attaching at least one adaptor to the single-stranded polynucleotide to yield a strand-tagged single-stranded polynucleotide, wherein the at least one adaptor comprises a strand identifying tag sequence, wherein the strand identifying tag sequence is unique to the single-stranded polynucleotide in the given reaction volume, and second, conducting a primer extension reaction to yield a plurality of amplification products comprising strand-tagged double-stranded polynucleotides; (c) sequencing said amplification products to yield a plurality of sequencing reads; (d) identifying from the plurality of sequencing reads, a given first complementary strand and a given second complementary strand as originating from a common double-stranded polynucleotide based on (i) sequences of the respective 3' ends and 5' ends and (ii) polynucleotide sequences of the corresponding complementary strands which are not perfectly complementary; (e) comparing polynucleotide sequences of the given first complementary strand and the given second complementary strand originating from the common double-stranded polynucleotide; and (f) calling a sequence difference in the given first complementary strand relative to a reference sequence as the sequence variant only when the corresponding given second complementary strand originating from the common double-stranded polynucleotide comprises a complement of the sequence difference.

In various embodiments of the aforementioned aspects, an individual strand-tagged, linear double-stranded concatemer comprises two or more copies of the corresponding single-stranded polynucleotide (e.g., circularized single-stranded polynucleotide). In some embodiments, the method further comprises comprising calling the sequence difference as the sequence variant only when the same sequence difference occurs in at least one copy in the linear concatemer.

In various embodiments of the aforementioned aspects, the method further comprises calling the sequence difference as the sequence variant only when the same sequence difference occurs in at least two double-stranded polynucleotides having different combinations of 3' ends and 5' ends, or junction sequences formed from linking 5' and 3' ends.

In various embodiments of the aforementioned aspects, the nucleic acid sample comprises cell-free polynucleotides, non-limiting examples of which include cell-free DNA, cell-free RNA, and circulating tumor DNA. In some embodiments, the nucleic acid sample comprises genomic DNA.

In various embodiments of the aforementioned aspects, the plurality of reaction volumes comprises a plurality of PCR tubes, microfluidic chambers, or droplets.

These above-characterized aspects of the present disclosure, as well as other aspects, are exemplified in a number of illustrated implementations and applications, some of which are shown in the figures and characterized in the claims section that follows. However, the above summary is not intended to describe each illustrated embodiment or every implementation of the present invention.

BRIEF DESCRIPTION OF THE DRAWINGS

FIGS. 1A-1H illustrate steps of various embodiments of the invention.

DETAILED DESCRIPTION

Figure 1A:
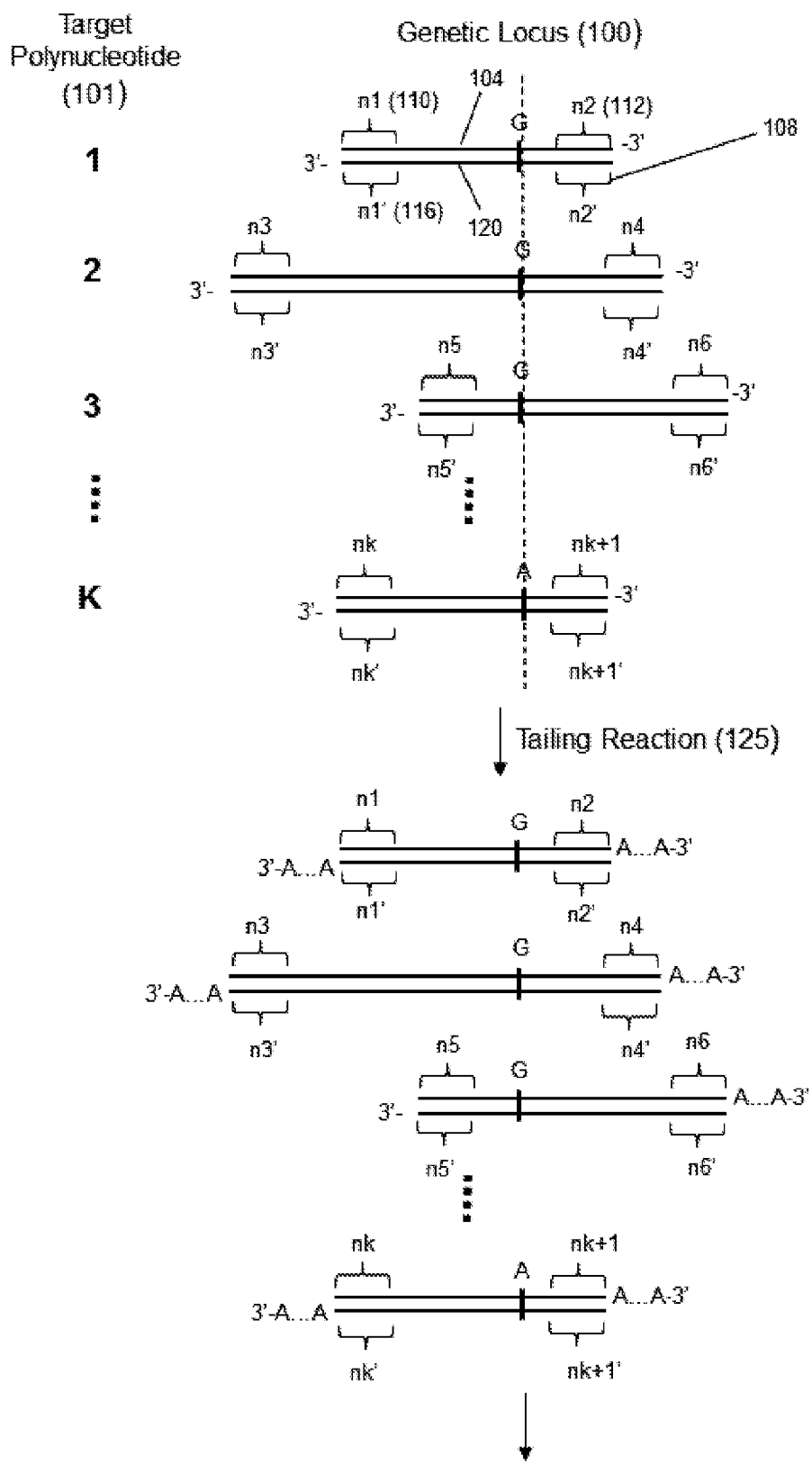

The practice of the various aspects and embodiments of the present disclosure may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation and use of synthetic peptides, synthetic polynucleotides, monoclonal antibodies, nucleic acid cloning, amplifying, sequencing and analysis, and related techniques. Specific illustrations of suitable techniques are provided in the examples provided herein. However, other equivalent conventional procedures can also be used. Such conventional techniques and descriptions can be found in standard laboratory manuals such as *Genome Analysis: A Laboratory Manual Series* (Vols. I-IV); *PCR*

Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); and Strachan and Read, Human Molecular Genetics, Second Edition (Wiley-Liss, New York, 1999).

"Amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation.

"Concatemer," as used herein, generally refers to a ligation product or an amplification product comprising a continuous polynucleotide that in one embodiment contains more than one copy of a target polynucleotide sequence (e.g. more than 1, 2, 3, 4, 5, 6, 7, 8, 9, or 10 copies of the target sequence). In some embodiments, a concatemer comprises at least 2 copies of a target polynucleotide sequence. In some embodiments, a concatemer contains multiple copies, or a plurality of copies, of a target polynucleotide sequence linked in tandem. In some embodiments, additional polynucleotide sequences are interspersed between the multiple copies, or plurality of copies, of a target polynucleotide sequence.

"Extension product," as used herein, generally refers to a product of a reaction in which a polynucleotide (e.g. a nucleotide primer or a target polynucleotide) is extended by the covalent addition of nucleotides. In some cases, the nucleotide incorporation can be guided by a template. In some cases, the nucleotide incorporation can occur without a template. In some cases, an extension product is an amplification product, such as from PCR amplification or rolling circle amplification (RCA).

"Genetic locus," or "locus" in reference to a genome or target polynucleotide, refers to a contiguous sub-region or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In some embodiments, a genetic locus refers to any portion of genomic sequence, including mitochondrial DNA, from a single nucleotide to a segment of few hundred nucleotides, e.g. 100-300, in length. In other embodiments, a genetic locus refers to any portion of genomic sequence from a single nucleotide to a segment of a few tens of nucleotides, e.g. 10-30, in length. In some embodiments, a particular genetic locus may be identified by its nucleotide sequence, or the nucleotide sequence, or sequences, of one or both adjacent or flanking regions. In some embodiments, a genetic locus may be a single nucleotide position. In some embodiments, a genetic locus comprises a sequence variant, or equivalently, a genetic variant. In such embodiments, a genetic variant at the genetic locus may be a nucleotide at the position of the genetic locus, which nucleotide occurs naturally in a population and which may be referred to as a single nucleotide polymorphism, or as an allele. In other embodiments, a genetic locus may comprise an insertion of one or more nucleotides or a deletion of one or more nucleotides with respect to a reference sequence.

In general, the term "kit" refers to any delivery system for delivering materials or reagents for carrying out a method of the present disclosure. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Molecular tag" or "barcode" (the terms are used interchangeably herein) refers to an oligonucleotide that is attached to a polynucleotide and is used to identify and/or track the polynucleotide in a reaction. In some embodiments, a molecular tag is attached to the 3'- or 5'-end of a polynucleotide to form a linear conjugate, sometimes referred to herein as a "tagged polynucleotide," or equivalently, a "tag-polynucleotide conjugate." Molecular tags may vary widely in size and composition. In some embodiments, molecular tags can each have a length within a range of from 2 to 36 nucleotides, or from 4 to 30 nucleotides, or from 8 to 20 nucleotides. In some embodiments, molecular tags are selected from defined sets, or repertoires. In some embodiments, molecular tags are selected from random sequence oligonucleotides of a predetermined length.

In general, the term "primer" refers to an oligonucleotide, either natural or synthetic, that is capable, upon forming a duplex with a polynucleotide template, acting as a point of initiation of nucleic acid synthesis and being extended from its 3' end along the template so that an extended duplex is formed. The sequence of nucleotides added during the extension process may be determined by the sequence of the template polynucleotide. Usually primers are extended by a DNA polymerase. Primers usually have a length in the range of from 5 to 36 nucleotides, but can be longer than 36 nucleotides or shorter than 5 nucleotides.

"Rolling circle amplification" or "RCA" and "rolling circle replication (RCR)" or "RCR" (which are used synonymously) refer to a process in which a primer is annealed to a circular nucleic acid molecule and extended by a nucleic acid polymerase in the presence of nucleoside triphosphates to produce an extension product that contains one or more copies, and usually a plurality of copies, of the complementary sequence of the circular DNA molecule.

"Sequence variant" refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including but not limited to a translocation or fusion gene.

"Terminal transferase" (TdT) refers to a template independent polymerase, e.g., terminal a deoxynucleotidyl transferase, that catalyzes the addition of deoxynucleotides to the 3' hydroxyl terminus of DNA molecules, e.g., tailing. Protruding, recessed or blunt-ended double or single-stranded DNA molecules can serve as a substrate for TdT. In some forms, TdT is a 58.3 kDa enzyme that does not have 5' or 3' exonuclease activity. For some TdTs, the addition of Co2+ in the reaction makes tailing more efficient. For some TdTs, the addition of dNTPs to 3' OH protruding ends is more efficient than with 3' OH recessed or blunt ends.

In general, the term "predetermined nucleotide" refers to a nucleotide of a known type, such as in the case where nucleotides of only a single type are added to a reaction (e.g. a tailing reaction). Extending a 3' end of a polynucleotide by addition of a predetermined nucleotide typically involves the addition of one or more of the predetermined nucleotides to only the 3' end of the extended polynucleotide, such that complementary strands are identifiable based in part on the identity of the predetermined nucleotide to which it is attached. In some cases, the predetermined nucleotide comprises two or more different types of nucleotides; however, at least one nucleotide type selected from A, T, G, or C is excluded so as to facilitate strand identification (e.g. 2 or 3 types are used). The precise length (and in the cases of multiple types, order) are not necessarily predetermined, and may vary between different target polynucleotides in the same reaction, and even between strands of a double-stranded molecule. The predetermined nucleotide may be a selected from naturally occurring types (e.g. A, T, G, C, or U), or analogues thereof. Because the composition of the extension is by a predetermined nucleotide, it is possible to computationally ignore sequences corresponding to the added predetermined nucleotides in constructing consensus sequences, particularly where the 3' end of the target polynucleotide is identified based on alignment to a reference sequence. The identity and length of the sequence ignored in constructing a consensus sequence may still be evaluated for the purposes of distinguishing strands from the same initial double-stranded molecule (e.g. based on the type of nucleotide in the sequence compared to the type of predetermined nucleotide), as well as distinguishing different initial target polynucleotide molecules (e.g. based on differences in length of the added sequence). In some embodiments, one or more predetermined nucleotides are added by the activity of a terminal a deoxynucleotidyl transferase (TdT) or an exonuclease-free nucleic acid polymerase. In some embodiments, the predetermined nucleotides are not added by ligation.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary," as used herein, refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa emboss_water/nucleotide.html, optionally with default settings). Optimal alignment may be assessed using any suitable parameters of a chosen algorithm, including default parameters.

In an aspect, the present disclosure provides methods for accurately determining rare sequence variants by combining sequence information from complementary strands of target polynucleotides. In some embodiments, one or both of the complementary strands of a target, double-stranded polynucleotide are modified such that the resulting polynucleotide sequences are no longer perfectly complementary and are rendered separately identifiable by their polynucleotide sequences. In some embodiments, two strands are identified as originating from the same double-stranded polynucleotide in a sample based on sequences at the 5' and 3' ends and the two strands whose 5' and 3' ends indicate their origins from a common, or the same, double-stranded polynucleotide are distinguished from one another based on non-complementary polynucleotide sequences.

In some embodiments, complementary strands are distinctly tagged and rendered separately identifiable by adding one or more predetermined nucleotides to the 3' ends of target-polynucleotides to mark its complementary strands. In accordance with some embodiments, such nucleotide additions help in later pairing of strands from sequencing data that have originated from the same target polynucleotide in a sample. In some embodiments, such nucleotide additions also create a well-defined boundary between the ends of each of the target polynucleotide strands after their respective circularization. That is, in some embodiments, target polynucleotides are "tailed" with one or more (and in some embodiments, a plurality of) predetermined nucleotides in a tailing reaction. In some embodiments, polynucleotides having predefined sequences are attached, for example, by ligation to the 3' ends, 5' ends, or both 3' and 5' ends of complementary strands. In some embodiments, two strands are identified as originating from the same double-stranded polynucleotide in a sample by complementary junction sequences formed from linking 5' and 3' polynucleotide ends (e.g., after circularizing) and the two strands are rendered identifiable by strand-tagging sequences. In accordance with some embodiments, the junction sequences formed by linking 5' and 3' polynucleotide ends identified in sequencing data can be used identify sequencing reads as originating from a particular double-stranded input, or starting, molecule. In some embodiments, strand-tagging sequences uniquely associated with individual single-stranded input, or starting, molecules can be used to distinguish sequencing reads as originating from a particular strand of complementary strands. In additional embodiments, amplification and sequencing errors may be further reduced by amplifying circularized polynucleotides with primers containing barcodes or molecular tags (which terms are used herein synonymously).

As mentioned above, one aspect of the present disclosure provides the identification of complementary strands of target polynucleotides by a method comprising the following steps: (a) extending by one or more predetermined nucleotides 3' ends of the polynucleotides; (b) amplifying individual strands of the extended polynucleotides; (c) sequencing the amplified individual strands of the extended polynucleotides; and (d) identifying extended polynucleotides having complementary strands by the identity of 3' sequences and/or 5' sequences adjacent to the one or more predetermined nucleotides.

In one aspect, the present disclosure provides a method of identifying complementary strands in a nucleic acid sample comprising a plurality of double stranded polynucleotides, each double-stranded polynucleotide of the plurality of comprising a first complementary strand and a second complementary strand, each of which has a 5' end and 3' end. In some embodiments, the method comprises: (a) modifying at least one of the first complementary strand and second complementary strand of individual double-stranded polynucleotides to yield a plurality of modified first complementary strands, a plurality of modified second complementary strands, or a combination thereof, wherein subsequent to the modifying, a polynucleotide sequence of a first complementary strand is not identical to a polynucleotide sequence of the corresponding modified first complementary strand and a polynucleotide sequence of a second complementary strand is not identical to a polynucleotide sequence of the corresponding modified second complementary strand; (b) sequencing at least some of the first complementary strands, the second complementary strands, the modified first complementary strands, the modified second complementary strands, or amplification products thereof; and (c) identifying (i) a given first complementary strand and a given modified second complementary strand, (ii) a given modified first complementary strand and a given second complementary strand, or (iii) a given modified first complementary strand and a given modified second complementary strand, as originating from a common double-stranded polynucleotide based on (i) sequences of the respective 3' ends and 5' ends and (ii) polynucleotide sequences which are not perfectly complementary. In some embodiments, modifying at least one of the first complementary strand and second complementary strand comprises (i) extending a 3' end by adding one or more pre-determined nucleotides, (ii) attaching, for example by ligating, a polynucleotide having a predefined sequence to a 5' end, a 3' end, or both 5' and 3' ends, (iii) modifying a polynucleotide sequence of at least one of the first complementary strand and the second complementary strand, or (iv) combinations thereof. In some embodiments, modifying the polynucleotide sequence of at least one of the first complementary strand and the second complementary strand comprises subjecting at least one of the first complementary strand and second complementary strand to bisulfite treatment. Treatment of denatured DNA (e.g., single-stranded DNA) with sodium bisulfite generally leads to deamination of unmethylated cytosine residues to uracil, leaving 5-mC or 5-hmC intact. When amplified in subsequent polymerase chain reactions (PCR), the uracils are amplified as thymines, whereas 5-mC or 5-hmC residues are amplified as cytosines. Differences in polynucleotide sequences after bisulfide treatment can, in some cases, be used to distinguish complementary strands of a double-stranded polynucleotide.

Another aspect of the present disclosure provides the identification of complementary strands of target polynucleotides obtained from a sample, which in some embodiments may be implemented in a method comprising the following steps: (a) extending by one or more predetermined nucleotides ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying by rolling circle replication (RCR) of the single stranded polynucleotide circles to form concatemers of the single stranded polynucleotide circles; and (d) identifying concatemers containing complementary strands of polynucleotides by the identity of 3' sequences and 5' sequences adjacent to the one or more predetermined nucleotides. In some embodiments, the step of extending is implemented by extending 3' ends of both strands of the target polynucleotides with an untemplated 3' nucleotide addition activity. In some embodiments, such 3' nucleotide addition activity may be provided by a terminal deoxynucleotidyl transferase (TdT) or an exonuclease-free nucleic acid polymerase. In some embodiments, the one or more predetermined nucleotides is a plurality of predetermined nucleotides. The foregoing steps of extending may be implemented by conventional extension reaction conditions, for example, using manufacturer's recommended reaction conditions for either the TdT or the polymerase enzymes. In other embodiments, the step of extending may be implemented by ligation of a plurality of predetermined nucleotides in double stranded form, for example, by blunt-end ligation. In this latter embodiment, target polynucleotides may be phosphorylated prior to ligation.

In some embodiments, after amplification by RCR, sequences of the resulting concatemers are identified using conventional sequencing methods. Such methods include converting concatemers to double stranded form by complementary strand synthesis and/or attaching adaptors, as may be required for particular sequencing approaches. In some embodiments, the complementary strand is synthesized by providing one or more reverse primers that each anneal to a specific site of the copied target polynucleotide and extending the one or more reverse primers by a polymerase, for example, in a process described in Lin et al, International patent publication WO2015/089333, and its counterpart U.S. application, which are incorporated herein by reference.

In some embodiments, the step of extending is carried out on target polynucleotides in double stranded form. In other embodiments, the step of extending is carried out on target polynucleotides in single stranded form, for example, after a denaturation step. In some embodiments, the step of circularizing the strands of the target polynucleotide may include a step of denaturing and/or separating the two strands of the target polynucleotides prior to circularization.

In accordance with some embodiments, the step of identifying pairs of concatemers containing complementary strands of a target polynucleotide is implemented by sequencing the concatemers followed by sequence comparisons using data analysis techniques, as described more fully below. In particular embodiments, the step of identifying includes steps of attaching sequencing primer binding sites (e.g. via adaptor ligation, PCR, or like treatments) to prepare the concatemers for particular sequencing techniques, described more fully below.

Illustrations of processes in accordance with some embodiments are provided in FIGS. 1A-1H, and in particular for embodiments employing 3' tailing reactions. FIG. 1A shows cell-free double stranded polynucleotides 1, 2, 3 . . . K (101) (e.g., target polynucleotide) of a sample, which each contain a genetic locus (100) consisting of a single nucleotide, which may be occupied by a "G" or a rare variant "A". A sample containing such polynucleotides may be a patient tissue sample, such as a blood or plasma sample, or the like. Typically, reference sequences (e.g. in human genome databases) are available to compare the polynucleotide sequences to. Each polynucleotide has four sequence regions corresponding to the sequences of the two complementary strands at each end. Thus, for example, target polynucleotide 1 of FIG. 1A has sequence regions n1 (110) and n2 (112) at each end of strand and has complementary sequence regions n1' (116) and n2' (108) at the ends of complementary strand (120). Although sequence regions of the various polynucleotide strands are illustrated as small portions of strands, the sequence regions may comprise the entire segments from the end of a strand to genetic locus (100).

To the target polynucleotides of the sample is added a 3' tailing activity along with nucleic acid monomers and/or other reaction components to implement tailing reaction (125) that extends the 3' ends with one or more A's. In this embodiment, the extension of predetermined nucleotides is shown as "A . . . A" to indicate that one or more nucleotides are added, but that the exact number added to each strand may be undetermined (unless an exo-polymerase is used, as noted below). The representation of the added nucleotide by "A . . . A" is not intended to limit the kind of added nucleotides to only A's. The added nucleotides are predetermined in the sense that the kind of nucleotide precursors used in a tailing reaction are known and selected as an assay design choice. For example, a factor in the selection of a kind of predetermined nucleotide for a particular embodiment may be the efficiency of the circularization step in view of the kind of nucleotide selected. In some embodiments, nucleotide precursors may be nucleoside triphosphates of any of the four nucleotides, either separately, so that homopolymer tails are produced, or in mixtures, so that bi- or tri-nucleotide tails are produced. In some cases, uracil, and/or nucleotide analogues may be used in addition to or in place of the four natural DNA bases. In some embodiments in which a CircLigase™ enzyme is used, predetermined nucleotides may be A's and/or T's. In some embodiments, an exo-polymerase is used in a tailing reaction, and only a single deoxyadenylate is added to a 3' end.

Figure 1B:
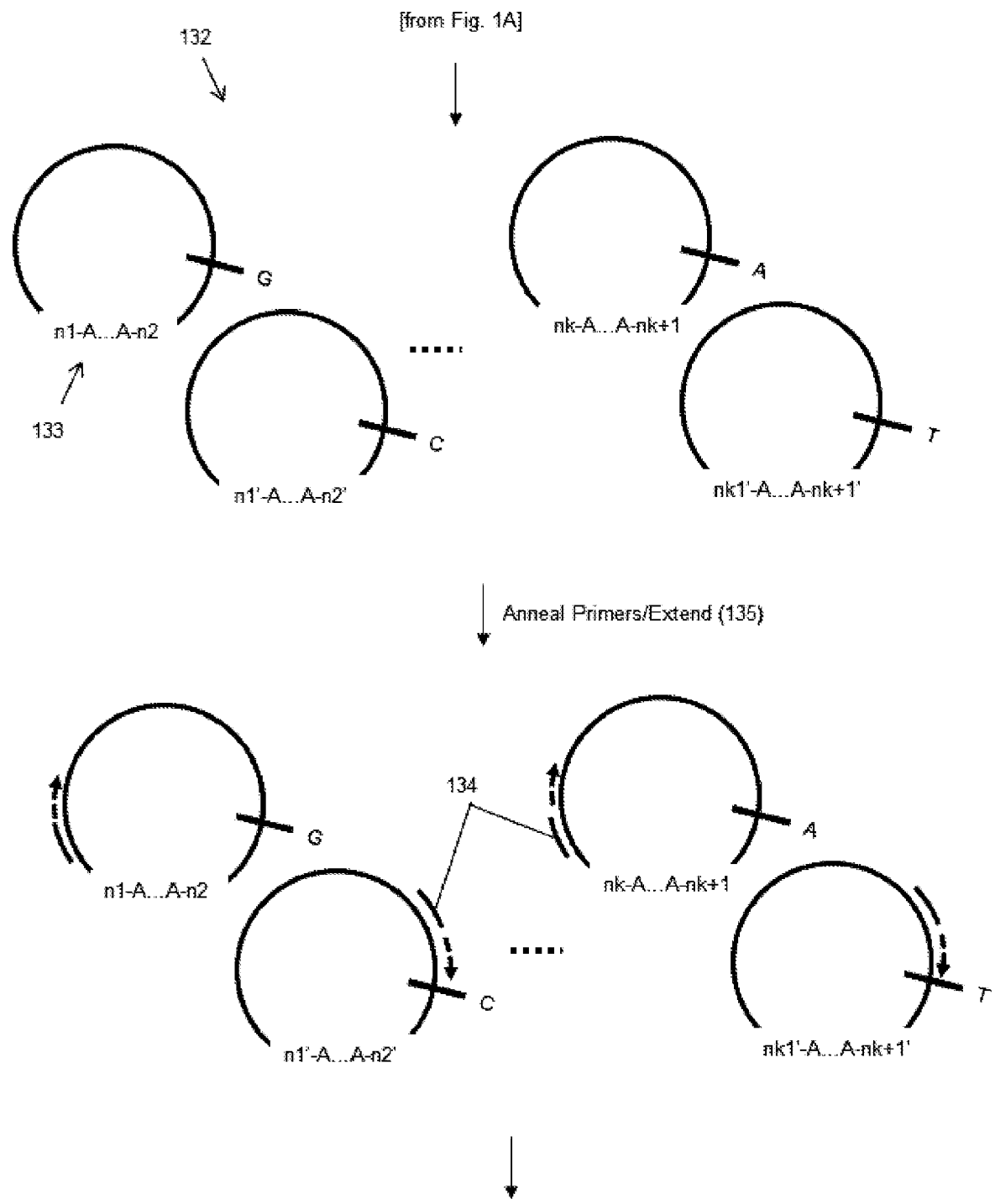

After tailing, and optional separation of the reaction products from the reaction mixture, individual strands are circularized, as shown in FIG. 1B, using a circularization reaction to produce circles (132), each comprising a sequence element of the form "nj-A . . . A-nj+1" (133). After circularization, and optional separation of circles (132) from the reaction mixture, primers (134) are annealed to one or more primer binding sites of circles (132), after which they are extended to produce concatemers each containing copies of their respective nj-A . . . A-nj+1 sequence element, as illustrated in FIG. 1E. After sequencing, complementary strands, such as (136) and (138), may be identified by matching sequence element components, nj and nj+1, with their respective complements, nj' and nj+1'. Selection of primer binding sites on circles (132) is a matter of design choice, or alternatively, random sequence primers may be used. In some embodiments, a single primer binding site is selected adjacent to genetic locus (100); in other embodiments, a plurality of primer binding sites are selected, each for a separate primer, to ensure amplification even if a boundary happens to occur in one of the primer binding sites. In some embodiments, two primers with separate primer binding sites are used to produce concatemers.

After identification of pairs of concatemers containing complementary strands, the concatemer sequences may be aligned and base calls at matching positions of the two strands may be compared. At some positions of concatemer pairs, as illustrated by (140) in FIG. 1F, a base called at a given position in one member of a pair may not be complementary to the base called on the other member of the pair, indicating that an incorrect call has been made due to, for example, amplification error, sequencing error, or the like. In this case, the indeterminacy at the given position may be resolve by examining the base calls at corresponding positions of other copies within the concatemer pair. For example, a base call at the given position may be taken to be a consensus, or a majority, of the base calls made for the individual copies in a pair of concatemers. Other methods for making such determinations would be available to one of ordinary skill in the art, which may be used in place of or in addition to these methods to supplement efforts to resolve base calls when sequence information between complementary strands are not complementary. In some cases, where bases at a specified position in complementary strands originating from the same double-stranded molecule (e.g. as identified by the 3' and 5' end sequences) are not complementary, a base call is resolved in favor of the reference sequence to which the sample sequence is compared, such that the difference is not identified as a true sequence variant with respect to such reference sequence.

Figure 1C:
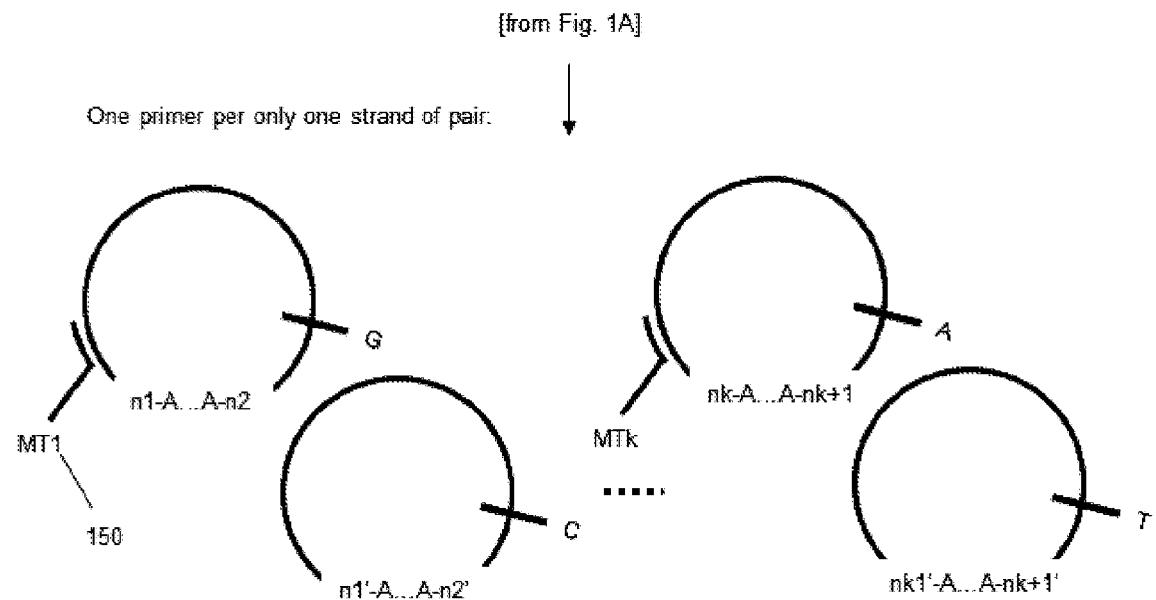
Figure 1D:
Figure 1D:
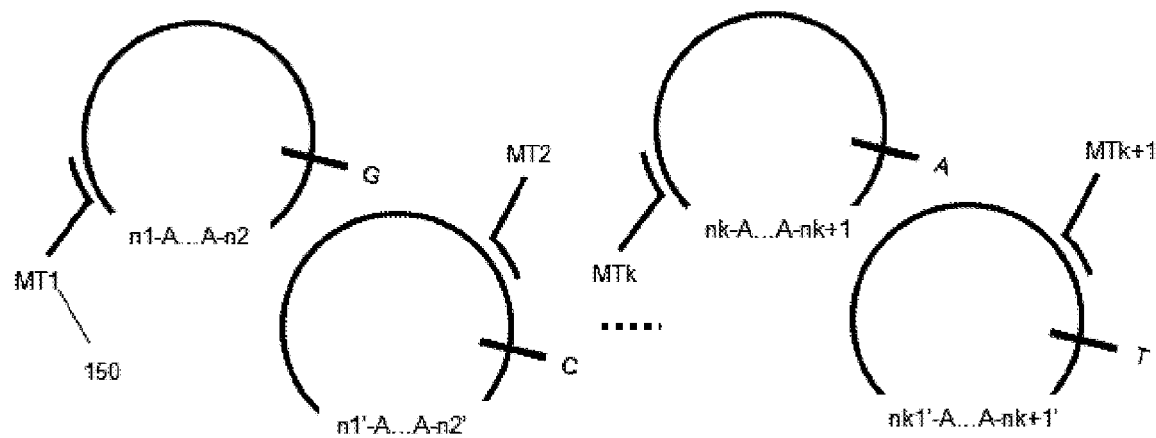
Figure 1E:
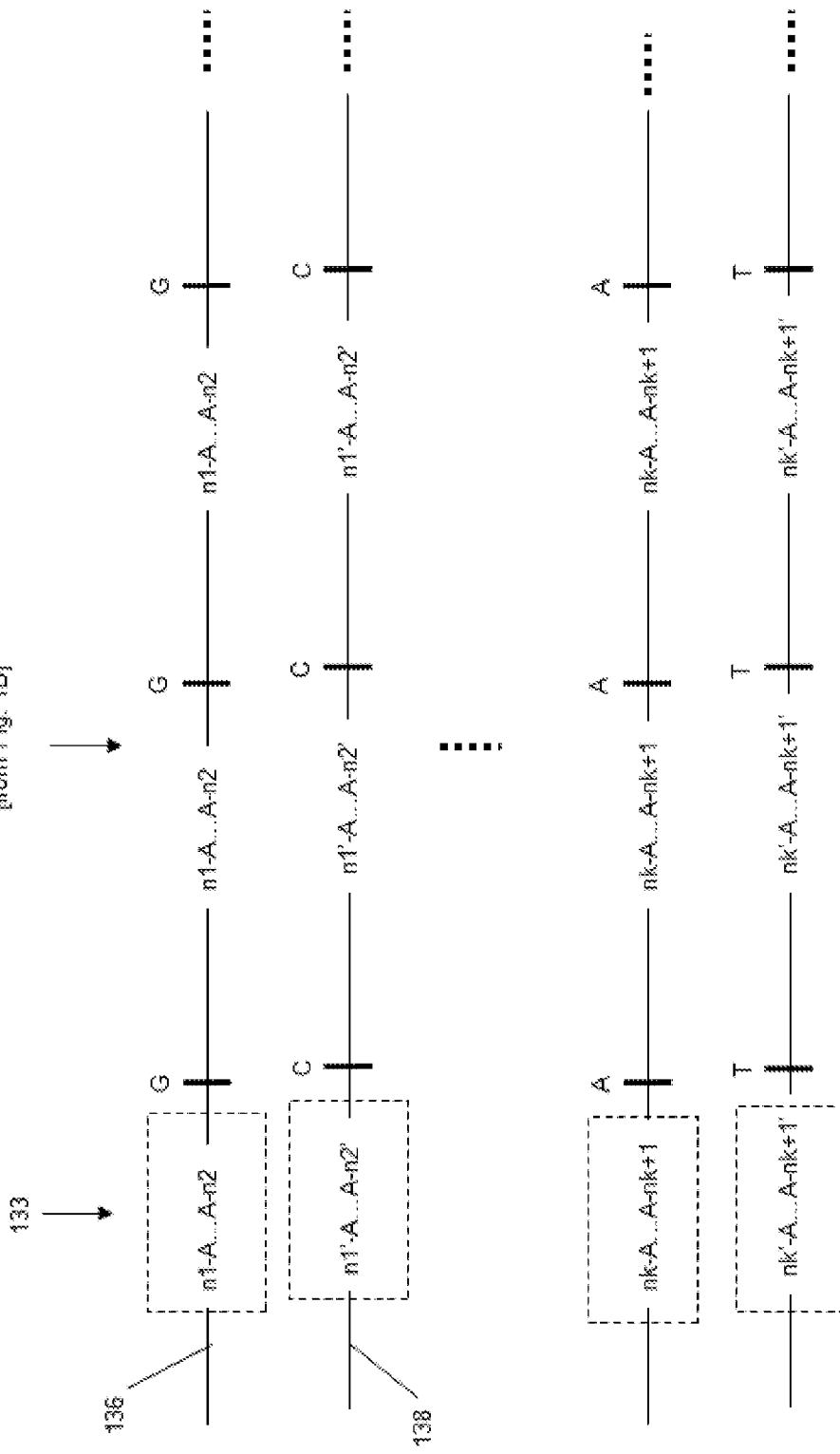
Figure 1F:
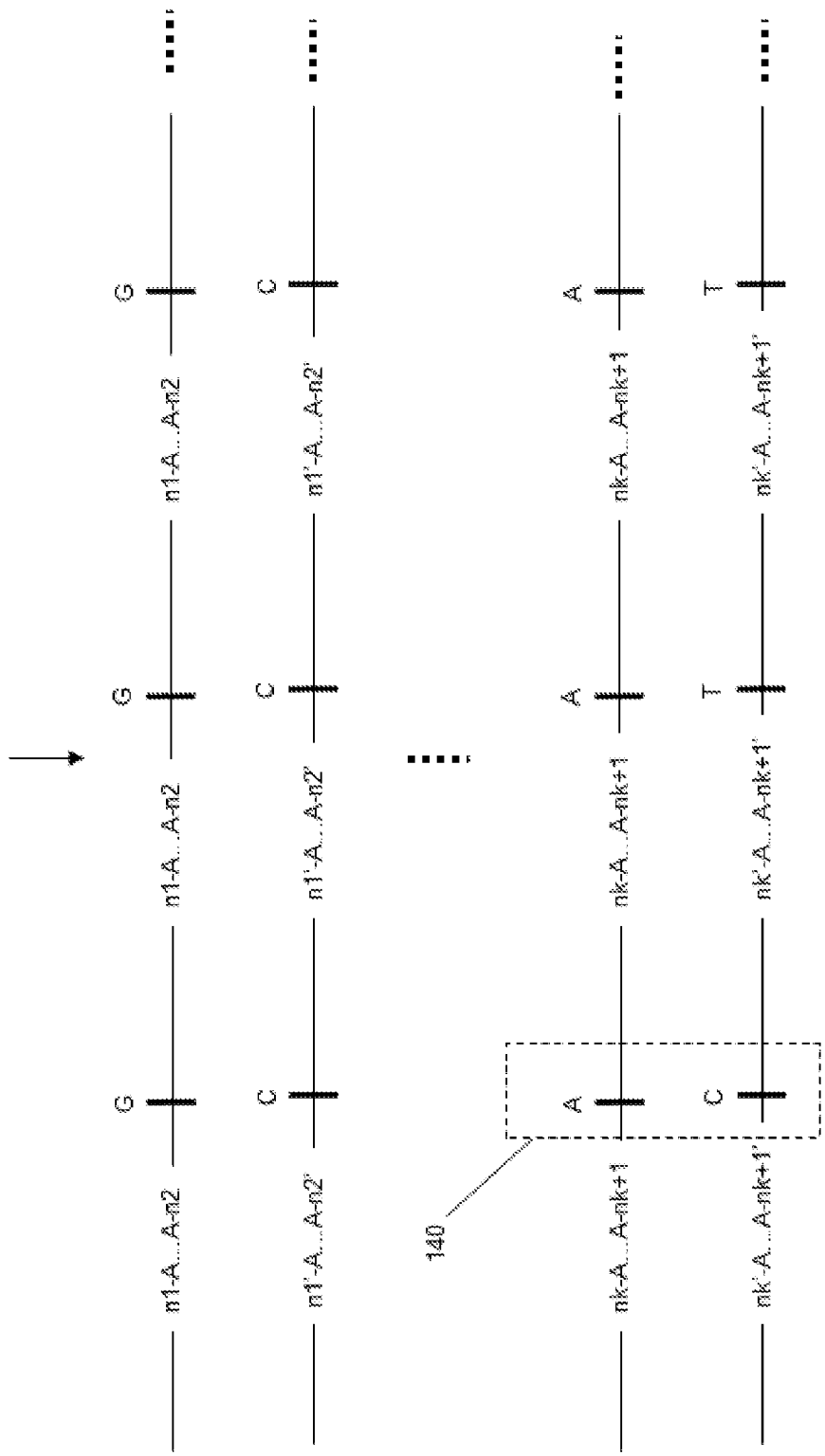
Figure 1G:
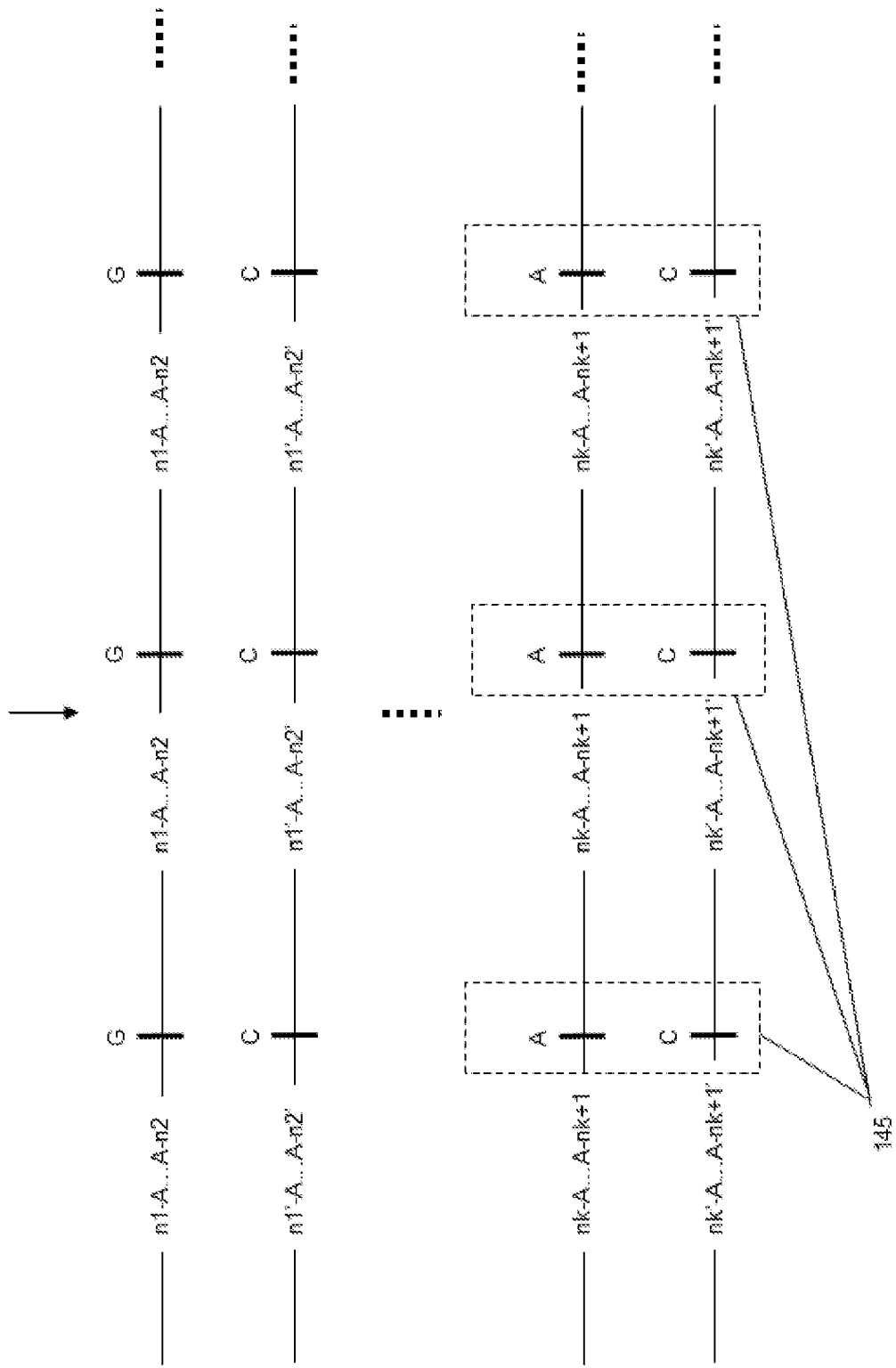

In other circumstances, the same error may appear in each copy of a target polynucleotide within a concatemer, as illustrated by (145) in FIG. 1G. Such data would suggest that the target polynucleotide was damaged before amplification or sequencing.

Figure 2A:
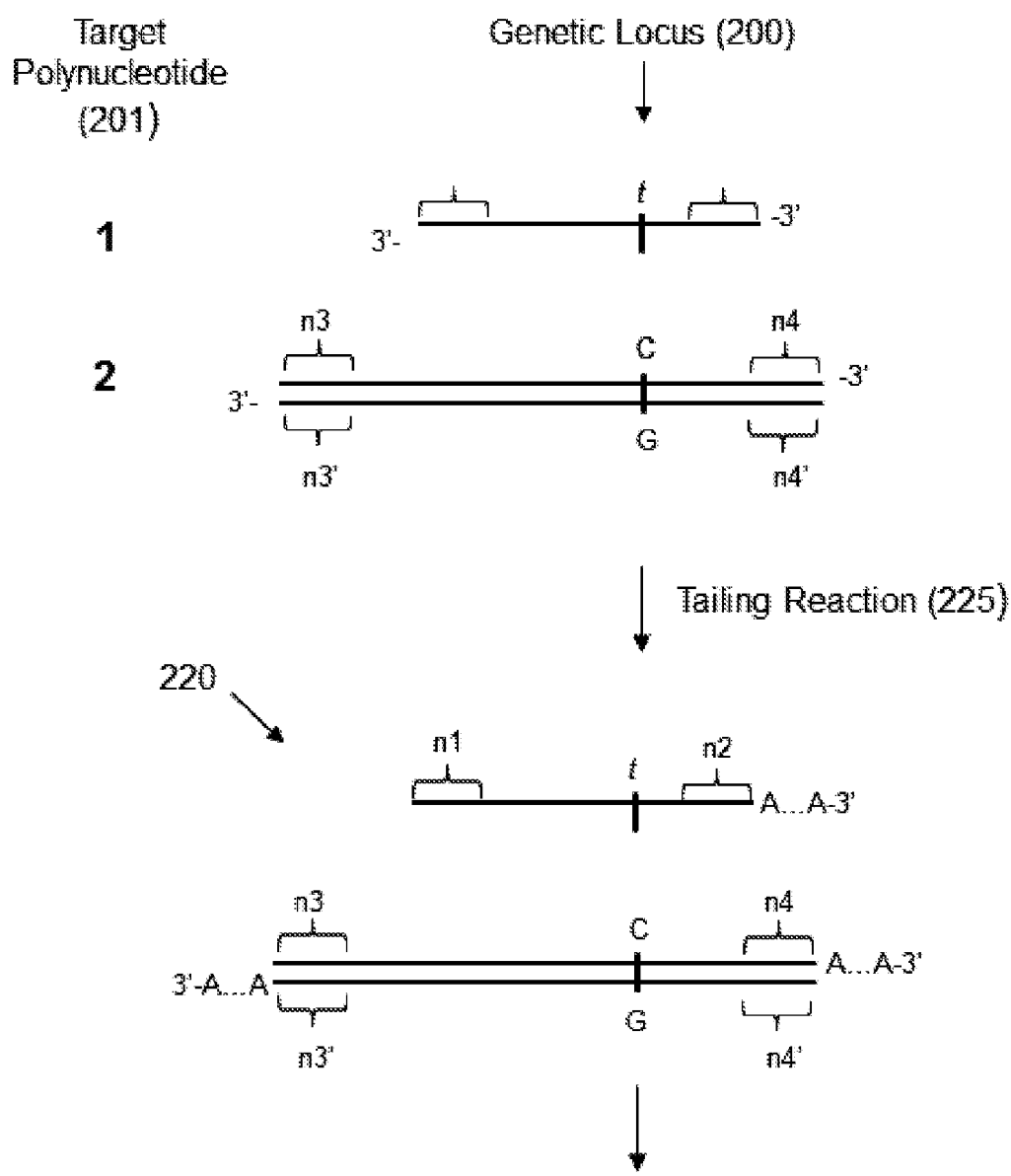
FIGS. 2A-2B illustrate embodiments where target polynucleotides include single stranded polynucleotides.
Figure 2B:
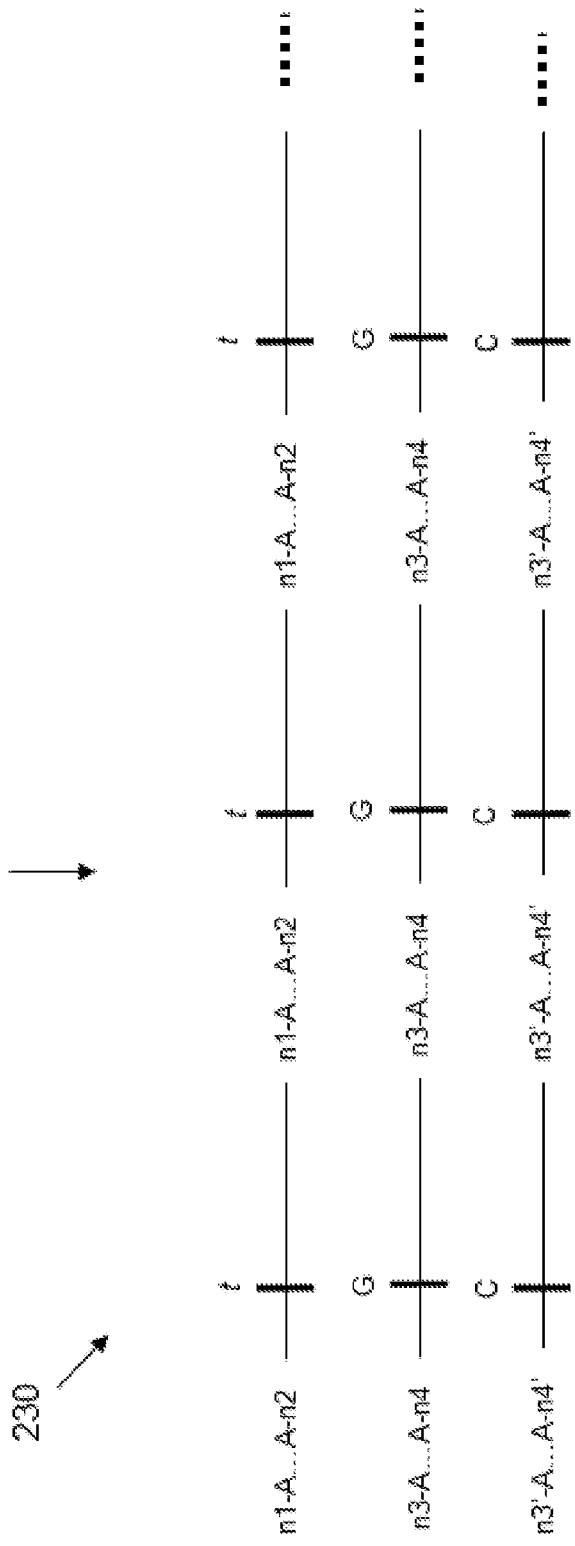

In still other circumstances, only a single concatemer may be identified; that is, a concatemer for which no match is found based on boundary information, such as, length of the segment of predetermined nucleotides, sequences of adjacent 3' and 5' ends, or the like. Such circumstances are illustrated in FIGS. 2A and 2B. In this illustrative example, target polynucleotides (201) comprise single stranded polynucleotide 1 and double stranded polynucleotide 2, each encompassing genetic locus (200). Predetermined nucleotides (for example, adenylates) may be attached to both polynucleotides 1 and 2 in tailing reaction (225) to form 3' tailed polynucleotides (220). As described above, polynucleotides (220) may then be circularized, amplified by RCA, and sequenced to give concatemer sequences (230), shown in FIG. 2B. In case an observed variant is common in DNA damage, for example, C to T or G to T, such information from an unpaired concatemer will still be helpful in deciding if it is a true mutation versus DNA damage.

In some embodiments, as illustrated in FIGS. 1C and 1D, primers each containing a molecular tag, e.g. MT1 (150), MT2, and so on, may be annealed to each single stranded circle at predetermined primer binding sites in order to produce concatemers each with a unique tag. The presence of unique molecular tags will distinguish products of single stranded circles that happen to have the same boundary, or nj-AA-nj+1 sequence element. Such tags may also be used for counting molecules to determine copy number variation at a genetic locus, for example, in accordance with methods described in Brenner et al, U.S. Pat. No. 7,537,897, or the like, which is incorporated herein by reference. In some embodiments, primers with molecular tags may be selected that have binding sites only on one strand of a target polynucleotide so that concatemers with molecular tags represent only one of the two strands of a target polynucleotide (as illustrated in FIG. 1C). In other embodiments, circles from complementary strands of a target polynucleotide may each be amplified using a primer having a molecular tag (as illustrated in FIG. 1D).

In some embodiments, the above steps for identifying complementary strands of target polynucleotides may be incorporated in a method for detecting rare variants at a genetic locus. In some embodiments, the method comprises the following steps: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying by rolling circle replication (RCR) the single stranded polynucleotide circles to form concatemers; (d) sequencing the concatemers; (e) identifying pairs of concatemers containing complementary strands of polynucleotides by the identity of 3' sequences and 5' sequences adjacent to the one or more predetermined nucleotides; and (f) determining the sequence of the genetic locus from the sequences of the pairs of concatemers comprising complementary strands of the same polynucleotide. In other embodiments, the step of amplifying by RCR the single stranded circles includes annealing a primer having a 5'-noncomplementary tail to the single stranded circles wherein such primer includes a unique molecular tag in the 5'-noncomplementary tail and extending such primer in accordance with an RCR protocol. The resulting product is a concatemer containing a unique molecular tag, which may be counted along with other molecular tags attached to circles from the same locus to provide a copy number measurement for the locus.

In some embodiments, the step of extending may be implemented by tailing by one or more predetermined nucleotides 3' ends of the polynucleotides in a tailing reaction. In some embodiments, such tailing may be implemented by an untemplated 3' nucleotide addition activity, such as a TdT activity, an exo-polymerase activity, or the like.

Using the steps described above, concatemer sequences can be identified from polynucleotide sequences. In large-scale-parallel-sequencing (also referred to as "next generation sequencing" or NGS), reads containing concatemers can be identified and used to perform error correction and find sequence variants. Junctions of the original input molecules (e.g., the start and the end of the DNA/RNA sequence) can be reconstructed from the concatemers by aligning them to reference sequences; and the junctions can be used to identify the original input molecule and to remove sequencing duplicates for more accurate counting. The strand identity of each read which may contain a concatemer can be computed by aligning the reads to reference sequences and checking the sequence element components, nj and nj+1 as described in FIG. 1A. Variants found in both concatemers labeled as complementary strands have a higher statistical confidence level, which can be used to perform further error correction. Variant confirmation using strand identity may be carried out by (but is not limited to) the following steps: a) variants found in reads with complementary strand identities are considered more confident; b) reads carrying variants can be grouped by its junction identification, the variants are more confident when complementary strand identities are found in reads within a group of reads having the same junction identification; c) reads carrying variants can be grouped by their molecular barcodes or the combination of molecular barcodes and junction identifications. The variants are more confident when the complement strand identities are found in reads within a group of reads having the same molecular barcodes and/or junction identifications.

Error correction using molecular barcodes and junction identification can be used independently, or combined with the error correction with concatemer sequencing as described in the previous steps. Error correction techniques may include a) grouping reads with different molecular barcodes (or junction identifications) into different read families which represent reads originating from different input molecules, b) building consensus sequences from the families of reads, c) using consensus sequences for variant calling, and d) combining molecular barcodes and junction identifications to form a composite identification (ID) for reads, which can be used to identify the original input molecules. In some embodiments, a base call (e.g. a sequence difference with respect to a reference sequence) found in different read families are assigned a higher confidence. In some cases, a sequence difference is only identified as a true sequence variant representative of the original source polynucleotide (as opposed to an error of sample processing or analysis) if the sequence difference passes one or more filters that increase confidence of a base call, such as those described above. In some embodiments, a sequence difference is only identified as a true sequence variant if (a) it is identified on both strands of a double-stranded input molecule; (b) it occurs in the consensus sequence for the concatemer from which it originates (e.g. more than 50%, 80%, 90% or more of the repeats within the concatemer contain the sequence difference); and/or (c) it occurs in two different molecules (e.g. as identified by different 3' and 5' endpoints, and/or by an exogenous tag sequence).

Strand identity can be determined by 1) reconstructing junctions of the original input molecules from reads which may contain concatemer sequences by aligning the sequences to reference sequences; 2) locating the junctions in the reads using the alignments; 3) extracting the sequence element component , nj and nj+1 , as described in FIG. 1A, which represents the strand identity from the sequence based on the junction locations in the reads; and in the case of concatemers, the sequence can be found between the junctions in the concatemer sequences; and 4) using the strand (positive or negative) of the reference sequence that the reads align to, combined with the strand identity sequences within the reads identified in step 3, to identify the original strand that was incorporated into the sequence library and sequenced, and to identify which strand a sequence variant originated from. For example, suppose a strand identity sequence "AA" is added to the end of a strand of original input DNA fragment. After sequencing, the read of the DNA fragment is aligned to the "+" strand of the reference and the strand identity sequence in the read is "AA" and we know the original input strand is the "+" strand. If the strand identity sequence is "TT", the read is reverse complementary to the original input strand and the original input strand is "-" strand. The strand identity determination allows a sequence variant to be distinguished from its reverse complementary counterpart, for example, C>T substitution from G>A substitution. The precise identification of allele changes can be used to carry out allele-specific error reduction in variant calling. For example, some DNA damage occurs more often as certain allele changes, and allele-specific error reduction can be carried out to suppress such damage. Such error reduction can be done by various statistical methods, for example, 1) calculation of distribution of different allele changes in sequencing data (baseline), followed by 2) z-test or other statistical tests to determine if a observed allele change is different from the baseline distribution.

In some embodiments, the present disclosure provides a method of identifying a genetic variant on a particular strand at a genetic locus by comparing the frequency of a measured sequence, or one or more nucleotides, to a baseline frequency of nucleotide damage that results in the same sequence, or one or more nucleotides, as the measured sequence. In some embodiments, such a method may comprise the following steps: (a) extending by one or more predetermined nucleotides 3' ends of the polynucleotides; (b) amplifying individual strands of the extended polynucleotides; (c) sequencing the amplified individual strands of the extended polynucleotides; (d) identifying complementary strands of polynucleotides by the identity of 3' sequences and/or 5' sequences adjacent to the one or more predetermined nucleotides and identifying nucleotides of each strand at the genetic locus; and (e) determining a frequency of each of one or more nucleotides at the genetic locus from the identified concatemers for identifying the genetic variant. In some embodiments, this method may be used to distinguish a genetic variant from nucleotide damage by the following step: calling at least one of the one or more nucleotides at the genetic locus on the strand identified by the one or more predetermined nucleotides as the genetic variant whenever the frequency of strands displaying the at least one nucleotide exceeds by a predetermined factor a baseline frequency of strands having nucleotide damage that gives rise to the same nucleotide.

As mentioned above, in some embodiments, the step of amplifying may be carried out by (i) circularizing individual strands of the polynucleotides to form single stranded polynucleotide circles, the one or more predetermined nucleotides defining a boundary between 3' sequences and 5' sequences of the polynucleotides in each single stranded polynucleotide circle; and (ii) amplifying by rolling circle replication the single stranded polynucleotide circles to form concatemers of the single stranded polynucleotide circles.

A baseline frequency of strands having nucleotide damage may be based on prior measurements on samples from the same individual who is being tested by the method, or a baseline frequency may be based on prior measurements on a population of individuals other than the individual being tested. A baseline frequency may also depend on and/or be specific for the kind of steps or protocol used in preparing a sample for analysis by a method of the disclosure. By comparing measured frequencies with baseline frequencies, a statistical measure may be obtained of a likelihood (or confidence level) that a measured or determined sequence is a genuine genetic variant and not damage or error due to processing.

Figure 3:
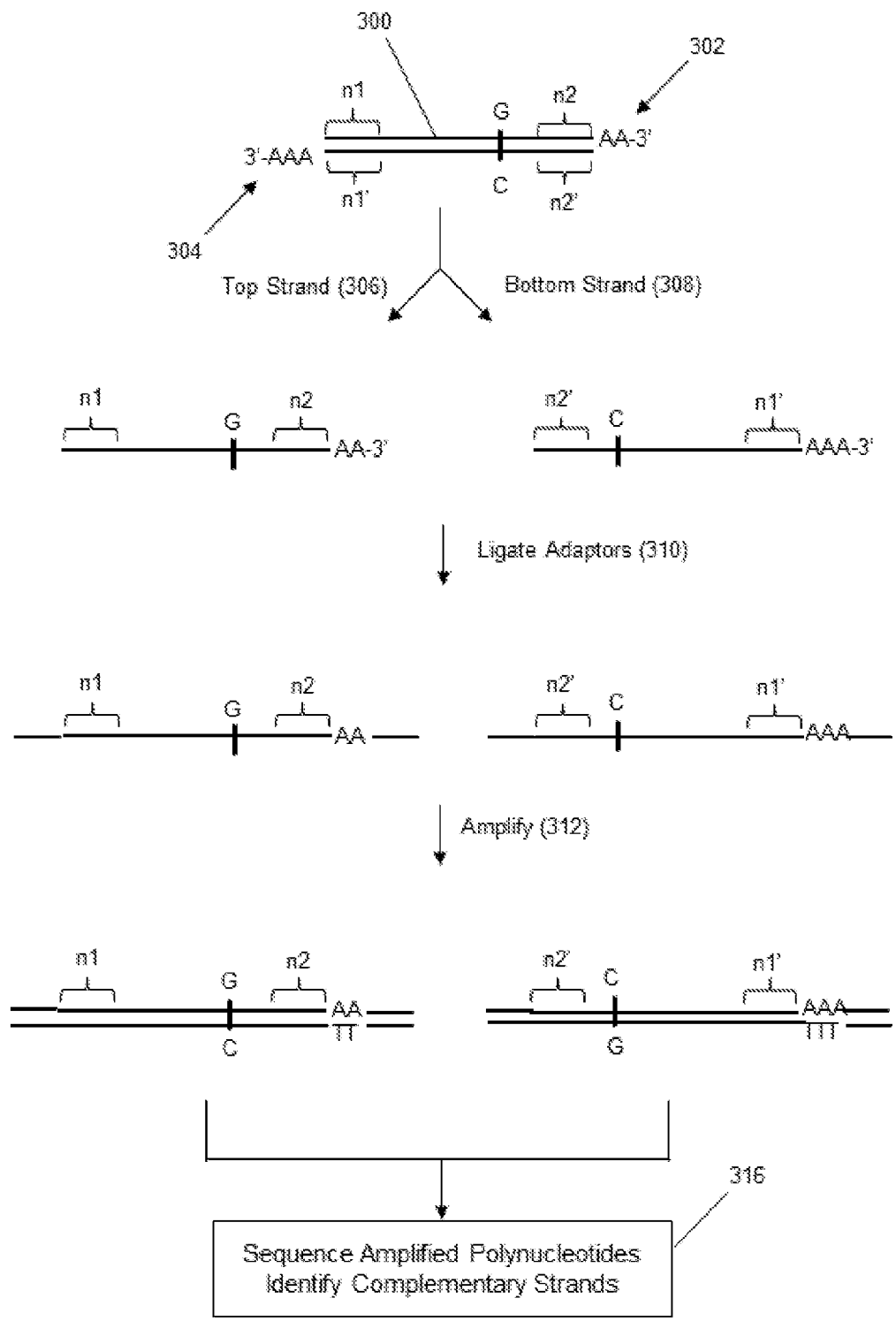
FIG. 3 illustrates steps of an embodiment of the invention employing PCR amplification.
Figure 4:
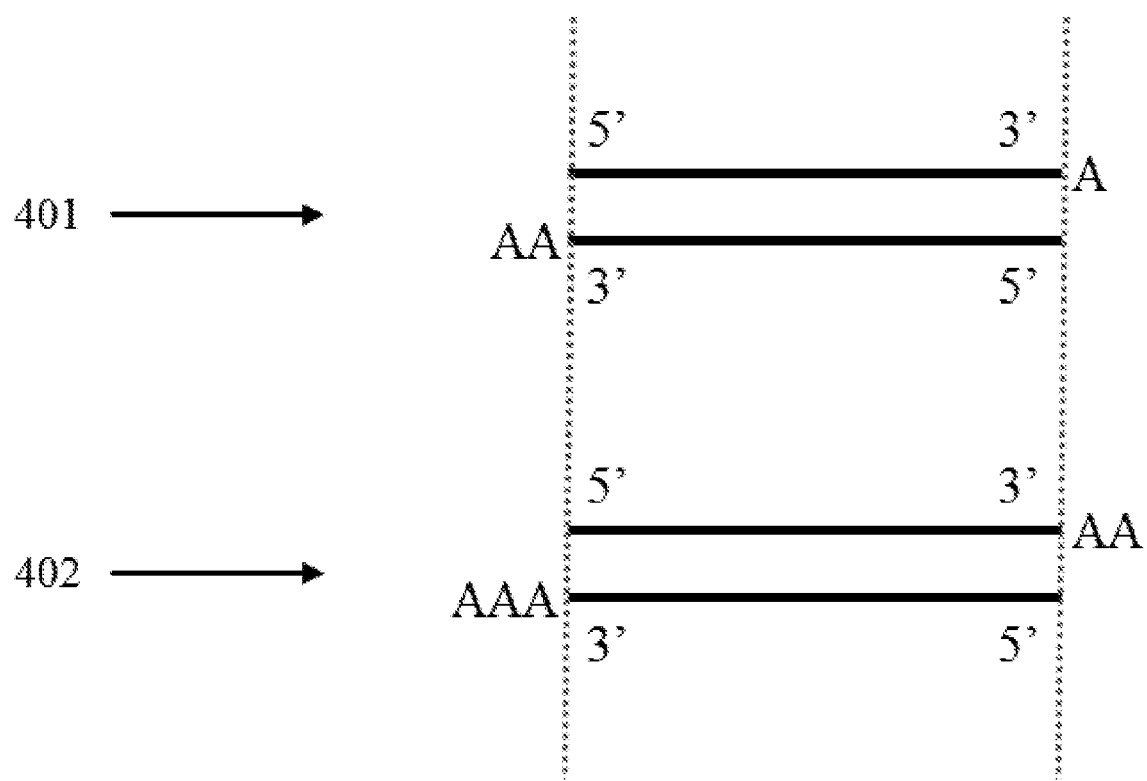
FIG. 4 illustrates an example of two double-stranded polynucleotides (401) and (402), having the same combination of original 5' and 3' ends (indicated by the dotted line), but are rendered distinguishable from one another by a difference in the number of predetermined nucleotides (in this case, adenine nucleotides) by which their respective 3' ends are extended.

In some embodiments, the step of amplifying is carried out using polymerase chain reaction (PCR). In such embodiments, the step of amplifying may comprise the following steps: ligating adaptors having primer binding sites or complements thereof to ends of the individual strands of the extended polynucleotides and performing a polymerase chain reaction. Individual strands of a target polynucleotide may be obtaining by denaturing the target polynucleotide after the one or more predetermined nucleotides are added to the 3' ends of its complementary strands. Exemplary steps for such amplification are illustrated in FIG. 3. 3' ends of target polynucleotide (300) are extended or tailed with poly-A additions of two A's (302) on the top strand and three A's (304) on the bottom strand. The two additions serve as tags for the top and bottom strands, along with the sequences n1 and n2 and n1' and n2', respectively. In particular, if strands originating from different target polynucleotides have the same sequences, n1, n2, n1' and n2', the strands may be matched to their correct complements (that is, the complements originating from the same parent target polynucleotides) whenever the number of predetermined nucleotides is different. Top strand (306) and bottom strand (308) are separated, for example by heating to a melting temperature, after which adaptors are ligated (310) to their ends. In some embodiments, such adaptors may be single stranded and may be attached to the ends of strand (306) and (308) by a single stranded ligation reaction, which may be preceded by a kinase treatment to phosphorylate 5' ends. In other embodiments, double stranded adaptors may be employed. After ligation of adaptors to 5' and 3' ends of strands (306) and (308), the products may be amplified (312) in a single stranded PCR using primers specific for primer binding sites in the adaptors or complements thereof. After amplification, the amplified strands may be prepared for sequencing, sequenced, and then analyzed to identify complementary strands.

In an aspect, the present disclosure provides a method of identifying complementary strands of a double-stranded polynucleotide without extending the 3' ends of the polynucleotides. In some embodiments, identifying complementary strands of a double-stranded polynucleotide involves use of "strand-tagging sequences" or "strand-identifying tag sequences" (used interchangeably herein), which refers to sequences that allow the amplification products derived from a given single-stranded input, or starting, polynucleotide to be distinguished from the amplification products derived from other single-stranded input polynucleotides of a sample. Strand-tagging sequences or strand-identifying tag sequences refer to oligonucleotide sequences linked or joined to the oligonucleotide sequences of amplification products derived from single-stranded input polynucleotides of a sample which can be used to distinguish amplification products derived from one input polynucleotide of a sample from those derived from another input molecule of the sample.

In some embodiments, strand tags comprising strand-tagging sequences are present on primers (e.g., strand-tagging primers), for example primers used in primer extension reactions. Primers for strand-tagging may comprise a pair of primers, e.g., forward and reverse primers. In some embodiments, only one primer of a strand-tagging primer pair carries the strand tag. In some embodiments, both primers of a strand-tagging primer pair carries a strand tag. In cases where both primers carry a strand tag, the individual strand tags of the pair (e.g., forward and reverse primers) may not be identical but are known to be related as a pair.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and a 3' end, the method comprising: (a) providing a plurality of circularized single-stranded polynucleotides in a plurality of reaction volumes, wherein an individual reaction volume contains only one circularized single-stranded polynucleotide formed by linking (i) the 5' end and the 3' end of a first complementary strand, (ii) the 5' end and the 3' end of a second complementary strand, (iii) the 5' end and the 3' end of a modified first complementary strand, or (iv) the 5' end and the 3' end of a modified second complementary strand, wherein the one circularized single-stranded polynucleotide has a junction sequence formed by said linking, and wherein a polynucleotide sequence of a first complementary strand and a polynucleotide sequence of the corresponding modified first complementary strand are not identical and a polynucleotide sequence of a second complementary strand and a polynucleotide sequence of the corresponding modified second complementary strand are not identical; (b) sequencing said plurality of circularized single-stranded polynucleotides, or amplification products thereof, to yield a plurality of sequencing reads; (c) identifying from the plurality of sequencing reads, (i) a given first complementary strand and a given modified second complementary, (ii) a given modified first complementary strand and a given second complementary strand, or (iii) a given modified first complementary strand and a given modified second complementary strand, as originating from a common double-stranded polynucleotide if (i) the given first complementary strand, or modified counterpart thereof, comprises a junction sequence that is complementary to that of the given second complementary strand, or modified counterpart thereof, and (ii) polynucleotide sequences which are not perfectly complementary; and (d) calling a sequence difference in the given first complementary strand, or modified counterpart thereof, relative to a reference sequence as the sequence variant only when the corresponding given second complementary strand, or modified counterpart thereof, which originates from the common double-stranded polynucleotide comprises a complement of the sequence difference.

In some embodiments, complementary strands are distinctly tagged and rendered separately identifiable by adding one or more predetermined nucleotides to the 3' ends of target-polynucleotides to mark its complementary strands. In accordance with some embodiments, such nucleotide additions help in later pairing of strands from sequencing data that have originated from the same target polynucleotide in a sample. In some embodiments, such nucleotide additions also create a well-defined boundary between the ends of each of the target polynucleotide strands after their respective circularization. That is, in some embodiments, target polynucleotides are "tailed" with one or more (and in some embodiments, a plurality of) predetermined nucleotides in a tailing reaction. In some embodiments, polynucleotides having predefined sequences are attached, for example, by ligation to the 3' ends, 5' ends, or both 3' and 5' ends of complementary strands. In some embodiments, two strands are identified as originating from the same double-stranded polynucleotide in a sample by complementary junction sequences formed from linking 5' and 3' polynucleotide ends (e.g., after circularizing) and the two strands are rendered identifiable by polynucleotide sequences which are not perfectly complementary. In accordance with some embodiments, the junction sequences formed by linking 5' and 3' polynucleotide ends identified in sequencing data can be used identify sequencing reads as originating from a particular double-stranded input, or starting, molecule. In some embodiments, strand-tagging sequences uniquely associated with individual single-stranded input, or starting, molecules can be used to distinguish sequencing reads as originating from a particular strand of complementary strands. In additional embodiments, amplification and sequencing errors may be further reduced by amplifying circularized polynucleotides with primers containing barcodes or molecular tags (which terms are used herein synonymously).

In some embodiments, modifying the polynucleotide sequence of at least one of the first complementary strand and the second complementary strand comprises subjecting at least one of the first complementary strand and second complementary strand to bisulfite treatment. Bisulfite treatment can alter particular nucleotides of a polynucleotide sequence, resulting in a modified polynucleotide sequence. Differences in polynucleotide sequences after bisulfide treatment can, in some cases, be used to distinguish complementary strands.

In an aspect, the present disclosure provides a method of identifying a sequence variant in a nucleic acid sample comprising a plurality of double-stranded polynucleotides, each double-stranded polynucleotide of the plurality comprising a first complementary strand and a second complementary strand, each strand having a 5' end and 3' end. In some embodiments, the method comprises (a) providing a plurality of circularized single-stranded polynucleotides in a plurality of reaction volumes, wherein an individual reaction volume contains only one circularized single-stranded polynucleotide formed by linking the 5' end and the 3' end of a first complementary strand or the 5' end and the 3' end of a second complementary strand, wherein the one circularized single-stranded polynucleotide has a junction sequence formed by the linking; (b) in a plurality of reaction volumes, conducting a primer extension reaction using a pair of forward and reverse strand-tagging primers, at least one of the pair comprising a strand identifying tag, to yield a plurality of strand-tagged, linear double-stranded concatemers, each of the concatemers comprising a strand identifying tag sequence, wherein the strand identifying tag sequence is unique to a circularized single-stranded polynucleotide in a given reaction volume; (c) sequencing the plurality of strand-tagged, linear double-stranded concatemers to yield a plurality of sequencing reads; (d) identifying from the plurality of sequencing reads, a given first complementary strand and a given second complementary strand as originating from a common double-stranded polynucleotide if (i) the given first complementary strand comprises a junction sequence that is complementary to that of the given second complementary strand, and (ii) the given first complementary strand comprises a strand identifying tag sequence that is different from that of the second complementary strand; and (e) calling a sequence difference in the given first complementary strand relative to a reference sequence as the sequence variant only when the corresponding given second complementary strand originates from the common double-stranded polynucleotide comprises a complement of the sequence difference.

Double-stranded polynucleotides, in some embodiments, comprise cell-free polynucleotides, including, but not limited to cell-free DNA and cell-free RNA. In some embodiments, the double-stranded polynucleotides comprise cell-free DNA. In some embodiments, the double-stranded polynucleotides comprise circulating tumor DNA.

In some embodiments, the circularized single-stranded polynucleotides are formed by first separating the double-stranded polynucleotides into separate single-stranded first and second complementary strands and then circularizing the separated first and second complementary strands by linking their respective 5' and 3' ends. Double-stranded polynucleotides can be separated into single-stranded form by various methods, including, but not limited, to thermal and chemical denaturation. In some embodiments, the double-stranded polynucleotides are separated into single-stranded first and second complementary strands by thermal denaturation. Following strand separation, the single-stranded polynucleotides can then be circularized by linking the 5' end and the 3' end of the polynucleotide. A single-stranded polynucleotide with a 5' end linked to a 3' end has junction sequence formed by the linking. A junction sequence refers to the nucleotides comprising the junction where the 5' end and the 3' end are linked and is generally read from a 5' to 3' direction. Junction sequences of two circularized single-stranded polynucleotides comprising a first complementary strand and a second complementary strand originating from a common double-stranded polynucleotide are likely to have complementary junction sequences. A junction sequence can comprise any suitable number of nucleotides, for example at least 2, 3, 4, 5, 6, 7, 8, 9, 10 nucleotides or more so long as complementary junction sequences can be identified. In some cases, however, junction sequences of complementary strands may not be complementary, for example, if the double-stranded polynucleotide has staggered or overhanging ends. In some embodiments, the circularized single-stranded polynucleotides are formed by first circularizing double-stranded polynucleotides and then separating circularized, double-stranded polynucleotides into individual single-stranded circles. When circularizing double-stranded polynucleotides, the respective 5' and 3' ends of the first and second complementary strands are linked to form, for each strand, a junction sequence.

Single-stranded polynucleotides and double-stranded polynucleotides can be circularized by various methods, including those described elsewhere herein. In some embodiments, circularized single-stranded polynucleotides are formed by first separating double-stranded polynucleotides into individual single-stranded polynucleotides, for example by thermal denaturation, and then circularizing the individual single-stranded polynucleotides using an enzyme such as a ligase. In some embodiments, circularized single-stranded polynucleotides are formed by first circularizing double-stranded polynucleotides using an enzyme such as a ligase and then separating circularized double-stranded polynucleotides into individual single-stranded circles, for example by thermal or chemical denaturation.

A plurality of circularized single-stranded polynucleotides can be provided in a plurality of reaction volumes such that an individual reaction volume contains only one circularized single-stranded polynucleotide. Reaction volume refers to a volume to which one or more reagents and/or products of a reaction can be confined. In some embodiments, a reaction volume is volume confined by physical boundaries, non-limiting examples of which include tubes, e.g., PCR tubes; wells, e.g., microwells; chambers, e.g., microfluidic chambers; and channels, e.g., microfluidic channels. In some embodiments, a reaction volume is not confined by physical boundaries, but rather the movement of reagents and/or products, for example by diffusion, away from the reaction volume is inhibited or minimized by electrical forces, magnetic forces, chemical forces, or combinations thereof. Non-limiting examples of such reaction volumes include droplets, e.g., water in oil droplets, in which the hydrophobic/hydrophilic properties of the water and oil can prevent the movement of reagents and/or products from one liquid phase to another liquid phase.

In a plurality of reaction volumes, primer extension can be conducted using a pair of forward and reverse strand-tagging primers. At least one of the pair of strand-tagging primers comprises a strand identifying tag and the primer extension reaction yields a plurality of strand-tagged, linear double stranded concatemers, each concatemer comprising a strand identifying tag sequence. In preferred embodiments, the strand identifying tag sequence is unique to a circularized single-stranded polynucleotide in a given reaction volume. A primer extension reaction can comprise rolling circle replication, polymerase chain reaction, or a combination thereof. A primer extension reaction can comprise thermal cycling methods, isothermal methods, or a combination thereof.

In some embodiments, the primer extension reaction comprises rolling circle replication and optionally further comprises polymerase chain reaction (PCR). In some cases, rolling circle replication using the pair of forward and reverse strand-tagging primers yields the plurality of strand-tagged, linear double-stranded concatemers. Each of the forward and reverse strand-tagging primers can comprise a target specific sequence at a 3' end that is complementary to a circular single-stranded polynucleotide sequence, or a complement thereof. These target specific sequences can hybridize to the single-stranded polynucleotide, or amplification products derived therefrom, and initiate primer extension. In some embodiments, each of the forward and reverse strand-tagging primers further comprises a common sequence at a 5' end not complementary to the circular single-stranded polynucleotide sequence, or a complement thereof. This common sequence, when present and incorporated into strand-tagged, linear double stranded concatemers can be used in an optional PCR step in which the strand-tagged, linear double-stranded concatemers are amplified with a pair of forward and reverse amplification primers to create additional copies of strand-tagged, double-stranded linear concatemers. In some embodiments, the primer extension reaction further comprises polymerase chain reaction using forward and reverse amplification primers, wherein the forward and reverse amplification primers comprise the common sequence at a 3' end which hybridizes to individual strands of a strand-tagged, double stranded linear concatemer and initiates primer extension.

In some embodiments, the primer extension reaction comprises both rolling circle replication and polymerase chain reaction (PCR). In some cases, rolling circle replication is first performed using a pair of forward and reverse amplification primers, each primer of the pair comprising a target specific sequence at a 3' end and a common sequence at a 5' end. The target specific sequences at the 3' end can be complementary to a circular single-stranded polynucleotide sequence, or a complement thereof, whereas the common sequence at the 5' end may not be complementary to the circular single-stranded polynucleotide sequence, or a complement thereof. Rolling circle replication using the pair of forward and reverse amplification primers can yield a plurality of linear double-stranded concatemers comprising the common sequence. These linear double-stranded concatemers comprising the common sequence can then be used as template for primer extension in subsequent polymerase chain reaction (PCR). PCR using a pair of forward and reverse strand-tagging primers can yield a plurality of strand-tagged, linear double-stranded concatemers. In some embodiments, each of the pair of forward and reverse strand-tagging primers comprises the common sequence at the primer 3' end which can hybridize to an individual strand of a linear double-stranded concatemer comprising the common sequence obtained previously from rolling circle replication and initiate primer extension. At least one of the pair of forward and reverse strand-tagging primers comprises the strand identifying tag at a 5' end. The strand-tagging sequence is subsequently incorporated into the amplification product, resulting in strand-tagged, linear double-stranded concatemers. As previously mentioned, in preferred embodiments, the strand identifying tag sequence or the strand-tagging sequence is unique to a circularized single-stranded polynucleotide in a given reaction volume, and therefore, the amplification products derived from a circularized single-stranded polynucleotide in a particular reaction volume is distinguishable from the amplification products derived from other circularized single-stranded polynucleotides in other reaction volumes.

Concatemers and/or amplification products thereof having strand identifying tag sequences can then be prepared for sequencing and then sequenced to yield sequencing reads, as described for other embodiments disclosed herein. The sequencing reads can be analyzed to identify a first complementary strand and a second complementary strand as originating from a common double-stranded polynucleotide if (i) the given first complementary strand comprises a junction sequence that is complementary to that of a given second complementary strand and (ii) if the first complementary strand comprises a strand identifying tag sequence that is different from that of the second complementary strand. For example, junctions of the original input molecules can be reconstructed from the concatemers by aligning them to reference sequences. Complementary junction sequences can be used to identify the original input molecules as originating from a common double stranded polynucleotide and to remove sequence duplicates, e.g., for more accurate counting. Among sequences identified as originating from a common double-stranded input molecule of a sample, the sequences of the strand identifying tags can be used to identify the first and second complementary strands.

After identification of pairs of concatemers containing complementary strands, the concatemer sequences may be aligned and base calls at matching positions of the two strands may be compared. At some positions of concatemer pairs, a base called at a given position in one member of a pair may not be complementary to the base called on the other member of the pair, indicating that an incorrect call has been made due to, for example, amplification error, sequencing error, or the like. In this case, the indeterminacy at the given position may be resolved by examining the base calls at corresponding positions of other copies within the concatemer pair. For example, a base call at the given position may be taken to be a consensus, or a majority, of the base calls made for the individual copies in a pair of concatemers. Other methods for making such determinations would be available to one of ordinary skill in the art, which may be used in place of or in addition to these methods to supplement efforts to resolve base calls when sequence information between complementary strands are not complementary. In some cases, where bases at a specified position in complementary strands originating from the same double-stranded molecule (e.g. as identified by the 3' and 5' end sequences and strand tag sequences) are not complementary, a base call is resolved in favor of the reference sequence to which the sample sequence is compared, such that the difference is not identified as a true sequence variant with respect to such reference sequence.

In some embodiments, the same error may appear in each copy of a target polynucleotide within a concatemer. Such data would suggest that the target polynucleotide was damaged before amplification or sequencing.

In some embodiments, sequencing reads containing concatemers are used to identify sequence variants and optionally perform error correction. In some aspects, a sequence difference in a first complementary strand relative to a reference is called as a sequence variant only when the corresponding second complementary strand which originates from the same (e.g., a common) double-stranded polynucleotide comprises a complement of the sequence difference. Reads carrying variants, for example, can be grouped by junction sequence, and the variants can be considered more confident when complementary strands originating from the same (e.g., a common) double-stranded polynucleotide are found in reads within a group of reads having the same junction identification, e.g., junction sequences which are complementary. In some embodiments, the sequence difference is only called as the sequence variant when the same sequence difference occurs in at least two double-stranded polynucleotides having different combinations of 3' ends and 5' ends (e.g., different double-stranded polynucleotide molecules).

In some embodiments, error correction using junction identification and strand identifying tag sequences is also performed when calling sequence variants. Error correction techniques include, but are not limited to, a) grouping reads with different junction sequences into different read families which represent reads originating from different input molecules, b) building consensus sequences from the families of reads, c) using consensus sequences for variant calling, and d) combining junction sequences and strand identifying tag sequences to form a composite identification (ID) for reads, which can be used to identify the original input molecules. In some embodiments, a base call (e.g. a sequence difference with respect to a reference sequence) found in different read families is assigned a higher confidence. In some cases, a sequence difference is only identified as a true sequence variant representative of the original source polynucleotide (as opposed to an error of sample processing or analysis) if the sequence difference passes one or more filters that increase confidence of a base call, such as confirming the presence on both first and second complementary strands. In some embodiments, a sequence difference is only identified as a true sequence variant if it is identified on both strands of a double-stranded input molecule (e.g., first complementary strand and second complementary strand). In some embodiments, a sequence difference is only identified as a true sequence variant if it occurs in the consensus sequence for the concatemer from which it originates (e.g. more than 50%, 80%, 90% or more of the repeats within the concatemer contain the sequence difference). In various embodiments of the aspects herein, each strand-tagged, linear double-stranded concatemer comprises at least one copy (e.g., greater than 1 copy, 2 copies, 3 copies, 4 copies, 5 copies or more) of the corresponding circularized single-stranded polynucleotide, and the sequence difference is called as the sequence variant only when the same sequence difference occurs in at least one copy (e.g., at least 2, 3, 4, 5, or more copies) in the concatemer. In some embodiments, a sequence difference is only identified as a true sequence variant if it occurs in two different molecules (e.g. as identified by different 3' and 5' endpoints, and/or by an exogenous tag sequence). In various embodiments, several variant calling criteria are used concurrently to improve the accuracy of base calls.

Figure 5A:
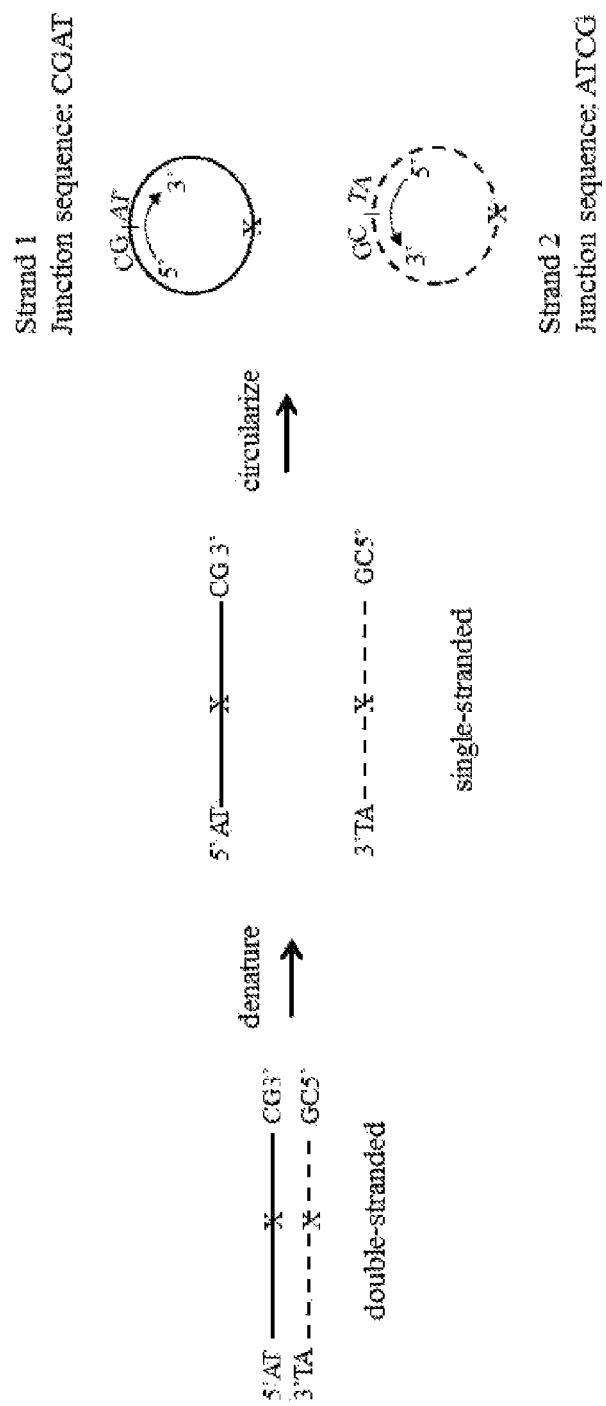
FIGS. 5A-5D illustrate embodiments wherein two strands of a double-stranded polynucleotide are identifying using strand-tagging sequences.

Illustrations of processes in accordance with some embodiments of the disclosure are provided in FIGS. 5A-5D, and in particular for embodiments where strand identifying tag sequences are used. FIG. 5A shows a target cell-free double stranded polynucleotide. The target cell-free double stranded polynucleotide comprises a gene sequence and the gene comprises a true mutation indicated by 'X' on both the first complementary strand (solid line, strand 1) and second complementary strand (dashed line, strand 2). In some embodiments, the double-stranded polynucleotides of the sample are treated, for example by thermal denaturation, to yield single-stranded polynucleotides. The single-stranded polynucleotides can then be circularized to form circular single-stranded polynucleotides, each of which has a junction between a 5' end and a 3' end comprising a junction sequence. The junction sequence for strand 1, read from a 5' to 3' direction, is CGAT. The junction sequence for strand 2, read from a 5' to 3' direction, is ATCG. The junction sequences of strand 1 and strand 2 are complementary. FIG. 5A illustrates this process for a single double-stranded polynucleotide for simplicity, but any given nucleic acid sample can contain a plurality of double-stranded polynucleotides which can undergo the sample preparation steps (e.g., denaturation and circularization) in parallel. As discussed previously, in some embodiments, the double-stranded polynucleotides are first circularized and then separated into circular single-stranded polynucleotides.

Prior to or subsequent to circularization of linear single-stranded polynucleotides to form circular single-stranded polynucleotides, the polynucleotides of the sample may be separated into multiple reaction volumes. In preferred embodiments, each reaction volume contains at most one single-stranded polynucleotide (linear or circular). In some embodiments, however, the reaction volumes may contain differing numbers of single-stranded polynucleotides (e.g., occupancy). For example, some of the reaction volumes may contain no single-stranded polynucleotides (e.g., empty), while some of the reaction volumes may contain one single-stranded polynucleotide (e.g., single occupancy) and some of the reaction volumes can contain greater than one single-stranded polynucleotide, e.g., two (e.g., double occupancy), three (e.g., triple occupancy), four (e.g., quadruple occupancy) or more single-stranded polynucleotides. The occupancy of the reaction volumes may vary depending on the process by which the polynucleotides are separated. In some embodiments, the polynucleotide sample is provided at a concentration, such that, when provided to the plurality of partitions, each partition comprises 0 or 1 single-stranded polynucleotide. In some embodiments, the individual circularized single-stranded polynucleotides are then subjected to a primer extension reaction, such as a primer extension reaction involving changes in temperature (thermocycling) or constant temperature (isothermal), or a combination thereof.

Figure 5B:
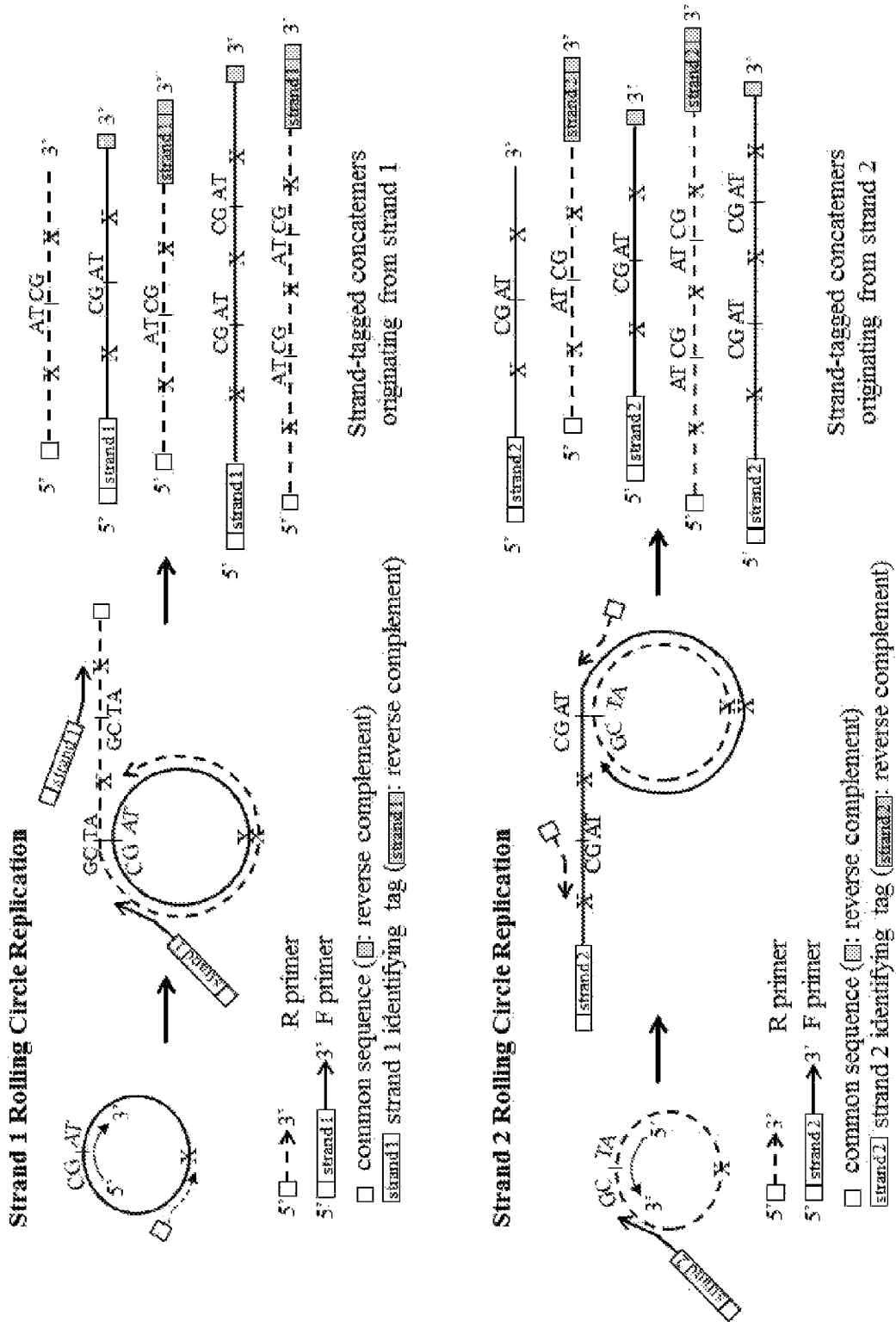

FIG. 5B illustrates schematically a primer extension reaction comprising rolling circle replication. As illustrated in FIG. 5B, a pair of forward and reverse strand-tagging primers are used in rolling circle replication to generate a plurality of strand-tagged, linear double stranded concatemers. Both primers of the pair comprise, at a 3' end, target specific sequences which can initiate primer extension from a portion of the circular single-stranded polynucleotide or amplification products thereof. At least one of the primer pair comprises the strand-identifying sequence and optionally, both primers of the pair comprise a common sequence at a 5' end. Double-stranded linear concatemers are generated by primer extension of a pair of forward and reverse primers for strand 1 and strand 2 as illustrated in FIG. 5B. As previously discussed, the strand identifying tag sequence is unique to a circularized single-stranded polynucleotide in a given reaction volume and thus strand 1 concatemers are linked to a strand-tag sequence that is different from that of strand 2 concatemers. In some embodiments, following the generation of concatemers in individual reaction volumes, the concatemers are further amplified, for example by polymerase chain reaction methods. Strand-tagged concatemers from multiple reaction volumes can be combined and amplified in bulk if desired, as the strand tags associated with each concatemer can be used to distinguish amplification products derived from strand 1 from those products derived from strand 2. The strand-tagged concatemers can then be optionally further processed and sequenced to yield sequencing reads for variant analysis as previously discussed herein.

Figure 5C:
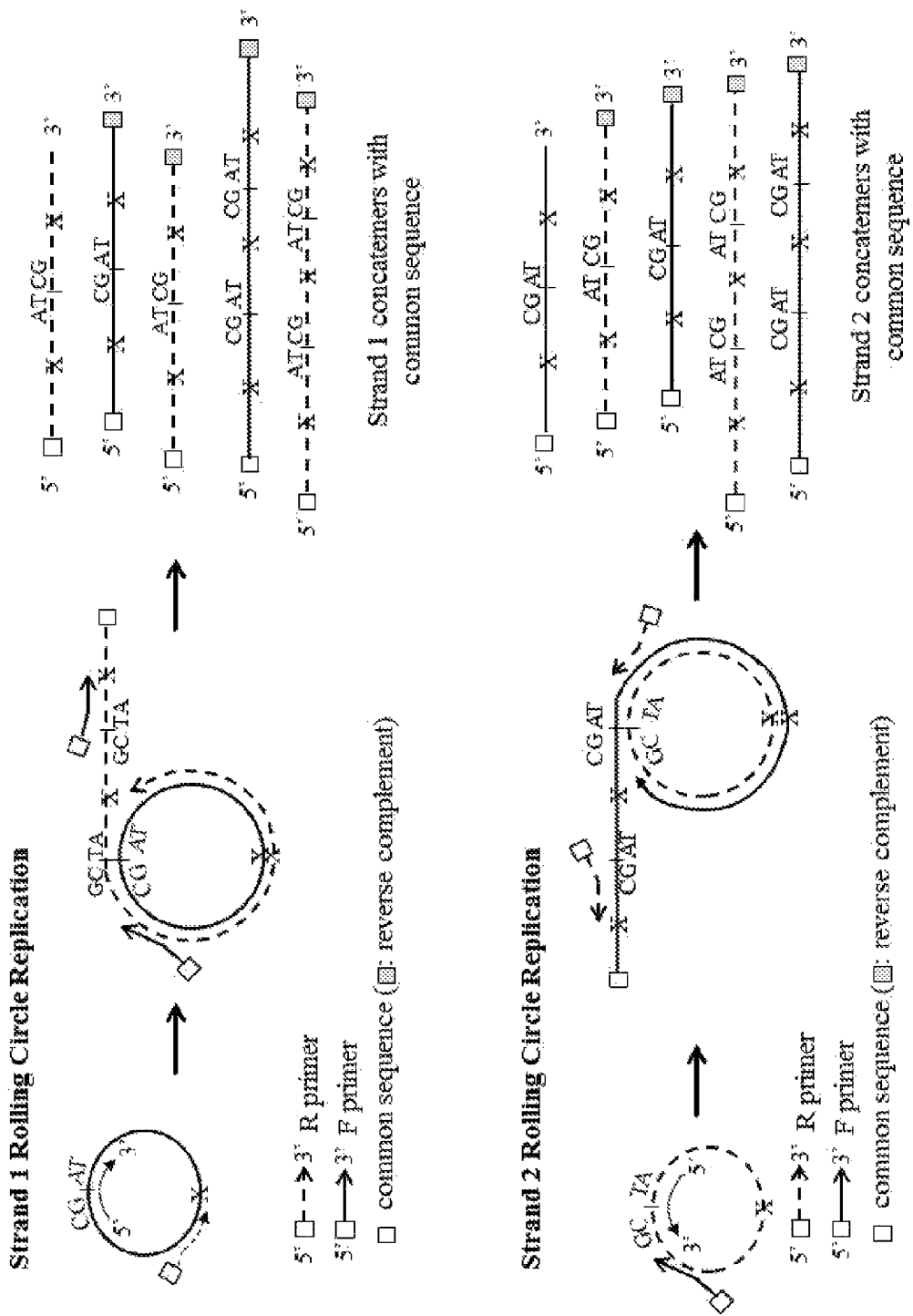
Figure 5D:
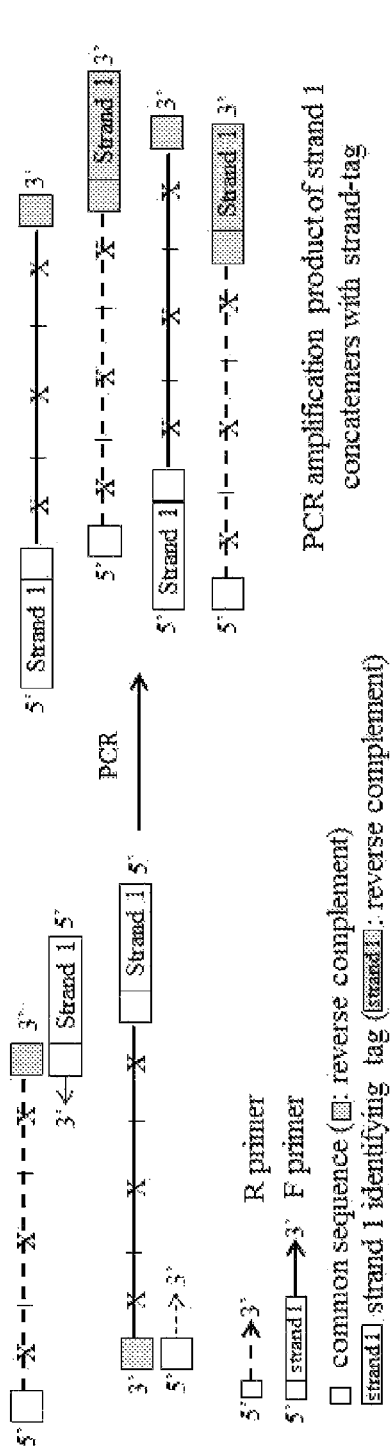
Figure 5D:
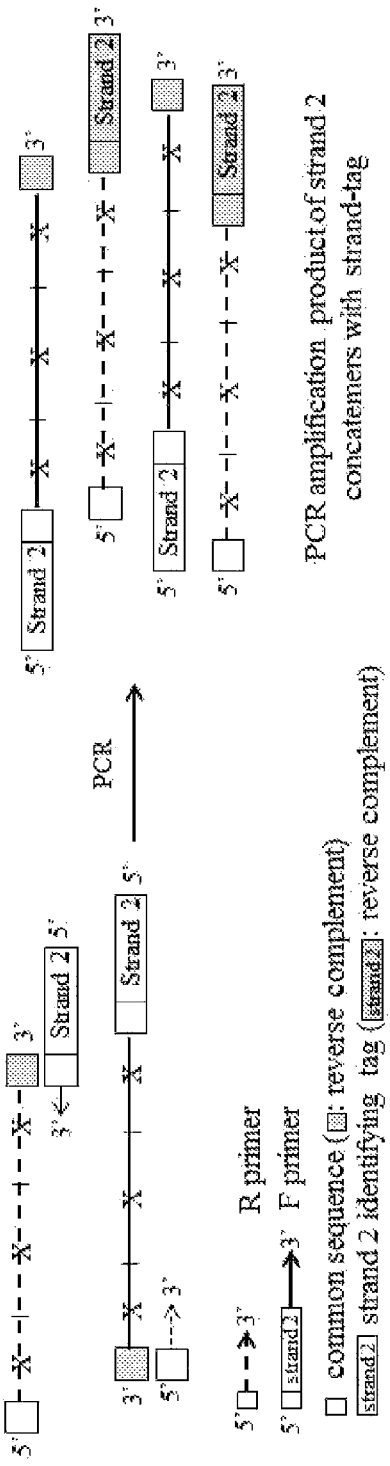

FIGS. 5C and 5D illustrate schematically a primer extension reaction comprising rolling circle replication and polymerase chain reaction. As illustrated in FIG. 5C, a pair of forward and reverse amplification primers are used in rolling circle replication to generate a plurality of linear double-stranded concatemers comprising common sequences. Both primers of the pair comprise, at a 3' end, target specific sequences which can initiate primer extension from a portion of the circular single-stranded polynucleotide or amplification products thereof. Both primers of the pair comprise a common sequence at a 5' end. Linear double-stranded concatemers are generated by primer extension of a pair of forward and reverse primers for strand 1 and strand 2 as illustrated in FIG. 5C. Following the generation of concatemers in individual reaction volumes, the concatemers are subjected to polymerase chain reaction to yield strand-tagged concatemers. As schematically illustrated in FIG. 5D, a pair of forward and reverse strand-tagging primers are used in polymerase chain reaction to generate a plurality of strand-tagged, linear double-stranded concatemers. Both primers of the pair comprise, at a 3' end, the common sequence which can initiate primer extension from the common sequence of concatemers previously obtained from rolling circle replication. At least one of the primers of the pair comprises that strand-identifying tag. Strand-tagged, linear double-stranded concatemers are generated by primer extension of a pair of forward and reverse primers for strand 1 and strand 2 amplification products as illustrated in FIG. 5D. As previously discussed, the strand identifying tag sequence is unique to a circularized single-stranded polynucleotide in a given reaction volume and thus strand 1 concatemers are linked to a strand-tag sequence that is different from that of strand 2 concatemers. The strand-tagged concatemers can then be optionally further processed and sequenced to yield sequencing reads for variant analysis as previously discussed herein.

Tailing Reactions

As mentioned above, in some embodiments, a tailing reaction may be carried out using an untemplated 3' nucleotide addition activity, such as TdT activity, an exo-polymerase activity, or the like, and the polynucleotides to which 3' tails are added may be single stranded or double stranded. Any of a variety of protocols may be employed for extending 3' ends of target polynucleotides in a tailing reaction. Typically, the 5' end of the molecule being tailed is not extended.

By way of example, in some embodiments, a TdT tailing reaction (for adding polyT tails) may comprise the following components: 5.0 µl 10× TdT Buffer (NEB); 5.0 µl 2.5 mM $CoCl_2$ solution; 5.0 pmols DNA (330 ng for 100 bp, 1 µg for 300 bp, and 10 pmols DNA ends); 0.5 µl 10 mM dTTP; 0.5 µl Terminal Transferase (20 units/µl); deionized $H_2O$ to a final volume of 50 µl. This reaction can be incubated at 37° C. for 30 minutes. The reaction can be stopped by heating to 70° C. for 10 minutes or by adding 10 µl of 0.2 M EDTA (pH 8.0). DNA can then be purified before proceeding to ligation. The rate of addition of dNTP's and thus the length of the tail can be a function of the ratio of 3' DNA ends:dNTP concentration, and also the type of dNTP used (where the relative rate of attachment is dT>dA>dC>dG). Length may also be modulated by adjusting reaction time.

By way of further example, in some embodiments, polyT tailing may be performed in the following exemplary ligation reaction mixture: 10 pmol single-stranded DNA; 2 µl CircLigase II 10× Reaction Buffer (NEB); 1 µl 50 mM $MnCl_2$; 4 µl 5 M Betaine (optional); 1 µl CircLigase II ssDNA Ligase (100 U); 0.5 µl 10 mM dTTP; 0.5 µl Terminal Transferase (20 units/µl); deionized $H_2O$ to a final volume of 20 µl. The reaction can be incubated at 37° C. for 30 minutes followed by 60° C. for 1 hour.

In some embodiments, tailing is performed with an exo-polymerase, such as Klenow Fragment (3'→5' exo-) in the following exemplary protocol. Mix the following components in a sterile microfuge tube: end-repaired, blunt DNA (amount variable); NEB Next dA-Tailing Reaction Buffer (10×), 5 µl; Klenow Fragment (3'→5' exo-), 3 µl; sterile $H_2O$, amount variable to total volume of 50 µl. The reaction can be incubated in a thermal cycler for 30 minutes at 37° C. The DNA sample is purified on one spin column.

Samples of Cell-Free Polynucleotides

In some embodiments, polynucleotides analyzed by methods of the present disclosure are "cell-free" polynucleotides. Any cell-free polynucleotide can be used by embodiments of the present disclosure. Cell-free polynucleotides can be obtained from a subject, such as any animal or living organism Non-limiting examples of subjects are mammals, such as humans, non-human primates, rodents such as mice and rats, dogs, cats, pigs, sheep, rabbits and others. In some embodiments, a subject is healthy, and cell-free polynucleotides obtained from the subject may not comprise a sequence variant associated with a disease or disorder. In some embodiments, a subject is suspected of having a disease or disorder, and cell-free polynucleotides obtained from the subject may comprise a sequence variant associated with the disease or disorder. In some embodiments, a subject is pregnant, and cell-free polynucleotides obtained from the subject comprise fetal polynucleotides.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are obtained from a subject. In some embodiments, samples are obtained by venipuncture. In some embodiments, samples are obtained by aspiration.

Various methods and commercial kits are available for obtaining cell-free polynucleotides, such as cell-free DNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments, a reaction mixture of the present disclosure comprises a circularized cell-free DNA as a circular target polynucleotide. In some embodiments, a reaction mixture of the present disclosure comprises a circularized fragment of genomic DNA as a circular target polynucleotide. In some embodiments, the circular target polynucleotide comprises sequences resulting from a chromosomal rearrangement. In certain embodiments, the chromosomal rearrangement is at least one of a deletion, duplication, inversion, and translocation. In some embodiments, circular target polynucleotides of the subject methods are single-stranded. In some embodiments, circular target polynucleotides of the subject methods are double-stranded.

In some embodiments, a reaction mixture of the present disclosure comprises a combined length of sequence portions of the target polynucleotide corresponding to (a) from 5' to 3' along the target polynucleotide, (i) sequence complementary to the first 3' end, and (ii) sequence identical to the second 3' end; and (b) intervening sequence between (i) and (ii), that together are 75 nucleotides or less. In some embodiments, the combined length of sequence portions of the target polynucleotide is 60 nucleotides or less. In some embodiments, the combined length of the sequence portions of the target polynucleotide is 50 nucleotides or less. In some embodiments, the combined length of the sequence portions of the target polynucleotide is 40 nucleotides or less. In some embodiments, the combined length of the sequence portions of the target polynucleotide is 30 nucleotides or less.

In some embodiments of the various aspects described herein, including the methods and reaction mixtures of the present disclosure, a circular target polynucleotide is formed from ligating a linear target polynucleotide. A circularized target polynucleotide formed from a linear target polynucleotide can comprise a sequence to be characterized, for example, a rare sequence variant or fusion gene. In some embodiments, a linear target polynucleotide is single-stranded. In other embodiments, a linear target polynucleotide is double-stranded. Non-limiting examples of target polynucleotides include DNA, RNA, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

In some embodiments of any of the various aspects disclosed herein, a circular target polynucleotide comprises a cell-free polynucleotide, including but not limited to a cell-free DNA or RNA (cfDNA or cfRNA). In some embodiments, a cell-free polynucleotide is a circulating tumor DNA or RNA (ctDNA or ctRNA). In some embodiments, a cell-free polynucleotide comprises fetal DNA or RNA. In some embodiments, cell-free polynucleotides are polynucleotides originating from a cell but not directly obtained from a cellular source, such as a tissue sample. Non-limiting examples of sources from which cell-free polynucleotides may originate are normal cells and tissue, abnormal cells and tissue (e.g., cancerous cells or tissue), fetal cells and tissue, and pathogens. A cell-free polynucleotide present in a non-cellular source can result from cell death (e.g., apoptosis or necrosis) or cell shedding. Sequence analysis of cell-free polynucleotides can be used to characterize the cell or population of cells from which the cell-free DNA is derived, such as tumor cells (e.g. in cancer detection), fetal cells (e.g. in prenatal diagnostics), cells from transplanted tissue (e.g. in early detection of transplant failure), a pathogen (e.g., bacteria or virus), or combinations thereof.

In some embodiments of any of the various aspects disclosed herein, a circular target polynucleotide comprises genomic DNA. In some embodiments, a circular target polynucleotide is derived from genomic DNA. Genomic DNA can be obtained from a cell sample using various methods and commercially available kits, such as a Qiagen DNeasy Tissue Kit. Genomic DNA can be obtained and purified from a sample using any suitable extraction, isolation, and purification method, examples of which are described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988)), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, and ethidium bromide).

In some embodiments, a circular target polynucleotide comprises fragmented cell-free DNA or fragmented genomic DNA. Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

In one aspect, the disclosure provides a method of identifying a sequence variant in a nucleic acid sample comprising less than 50 ng of polynucleotides, each polynucleotide having a 5' end and a 3' end. In some embodiments, the method comprises: (a) circularizing with a ligase individual polynucleotides in the sample to form a plurality of circular polynucleotides; (b) upon separating the ligase from the circular polynucleotides, amplifying the circular polynucleotides to form concatemers; (c) sequencing the concatemers to produce a plurality of sequencing reads; (d) identifying sequence differences between the plurality of sequencing reads and a reference sequence; and (e) calling a sequence difference that occurs with a frequency down to about 0.05% or lower (e.g. down to about 0.01%, 0.005%, 0.001%, 0.0005%, or lower) in the plurality of reads from the nucleic acid sample of less than 50 ng of polynucleotides as the sequence variant.

The starting amount of polynucleotides in a sample may be small. In some embodiments, the amount of starting polynucleotides is less than 50 ng, such as less than 45 ng, 40 ng, 35 ng, 30 ng, 25 ng, 20 ng, 15 ng, 10 ng, 5 ng, 4 ng, 3 ng, 2 ng, 1 ng, 0.5 ng, 0.1 ng, or less. In some embodiments, the amount of starting polynucleotides is in the range of 0.1-100 ng, such as between 1-75 ng, 5-50 ng, or 10-20 ng. In general, lower starting material increases the importance of increased recovery from various processing steps. Processes that reduce the amount of polynucleotides in a sample for participation in a subsequent reaction decrease the sensitivity with which rare mutations can be detected. For example, methods described by Lou et al. (PNAS, 2013, 110 (49)) are expected to recover only 10-20% of the starting material. For large amounts of starting material (e.g. as purified from lab-cultured bacteria), this may not be a substantial obstacle. However, for samples where the starting material is substantially lower, recovery in this low range can be a substantial obstacle to detection of rare variants. Accordingly, in some embodiments, sample recovery from one step to another in a method of the disclosure e.g. the mass fraction of input into a circularization step available for input into a subsequent amplification step (or sequencing step) is about or more than about 50%, 60%, 75%, 80%, 85%, 90%, 95%, or more. Recovery from a particular step may be close to 100%. Recovery may be with respect to a particular form, such as recovery of circular polynucleotides from an input of non-circular polynucleotides.

Circularizing Polynucleotides

Circular target polynucleotides may be formed from linear target polynucleotides by various methods. In some embodiments, a single linear target polynucleotide is circularized by end-joining. In some embodiments, a first linear target polynucleotide is joined to a second linear target polynucleotide, and then the un-joined end of the first target polynucleotide is joined to the un-joined end of the second linear target polynucleotide to form a circular target polynucleotide comprising the first and second target polynucleotides. Polynucleotides to be circularized may be single-stranded or double-stranded. Where single-stranded circles are desired, the polynucleotide may be a single-stranded polynucleotide as originally isolated, or may be treated to render the polynucleotide single-stranded (e.g. by denaturation). In some embodiments, a method for circularizing a polynucleotide involves an enzyme, such as use of a ligase (e.g., an RNA ligase or a DNA ligase). Non-limiting examples of enzymes that can be used to ligate a linear target polynucleotide into a circular target polynucleotide are ATP-dependent double-stranded polynucleotide ligases, NAD+ dependent DNA or RNA ligases, and single-strand polynucleotide ligases. Non-limiting examples of ligases are CircLigase I and CircLigase II (Epicentre; Madison, Wis.), *Escherichia coli* DNA ligase, *Thermus filiformis* DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre®Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions may contain a buffer component, small molecule ligation enhancers, and other reaction components. In some embodiments, the concentration of polynucleotides and enzyme is adjusted to facilitate intermolecular ligation rather than intramolecular ligation. In some embodiments, the reaction temperature and reaction time, or length of the reaction, is adjusted. Reaction temperatures and times can be adjusted as well. In some embodiments, 60° C. is used to facilitate intramolecular circles. In some embodiments, reaction times are between 12-16 hours. Reaction conditions may be those specified by the manufacturer of the selected enzyme. In some embodiments, joining the ends of a polynucleotide to form a circular polynucleotide (either directly to itself or to one or more other polynucleotides, e.g., a circular target polynucleotide comprises two target polynucleotides) produces a junction having a junction sequence. In some embodiments, an exonuclease step can be included to digest any unligated nucleic acids after the circularization reaction. That is, closed circles do not contain a free 5' or 3' end, and thus the introduction of a 5' or 3' exonuclease will not digest the closed circles but will digest the unligated components. This may find particular use in multiplex systems.

After circularization, reaction products may be purified prior to amplification or sequencing to increase the relative concentration or purity of circularized polynucleotides available for participating in subsequent steps (e.g. by isolation of circular polynucleotides or removal of one or more other molecules in the reaction). For example, a circularization reaction or components thereof may be treated to remove single-stranded (non-circularized) polynucleotides, such as by treatment with an exonuclease. As a further example, a circularization reaction or portion thereof may be subjected to size exclusion chromatography, whereby small reagents are retained and discarded, or circularization products are retained and released in a separate volume. A variety of kits for cleaning up ligation reactions are available, such as kits provided by Zymo oligo purification kits made by Zymo Research. In some embodiments, purification comprises treatment to remove or degrade ligase used in the circularization reaction, and/or to purify circularized polynucleotides away from such ligase. In some embodiments, treatment to degrade ligase comprises treatment with a protease, such as proteinase K. Proteinase K treatment may follow manufacturer protocols, or standard protocols (e.g. as provided in Sambrook and Green, Molecular Cloning: A Laboratory Manual, 4th Edition (2012)). Protease treatment may also be followed by extraction and precipitation. In one example, circularized polynucleotides are purified by proteinase K (Qiagen) treatment in the presence of 0.1% SDS and 20 mM EDTA, extracted with 1:1 phenol/chloroform and chloroform, and precipitated with ethanol or isopropanol. In some embodiments, precipitation is in ethanol.

Primer Extension and Amplification

Some embodiments of the present disclosure comprise primer extension and amplification reactions, such as one or more of generating concatemers, generating a plurality of extension products, and amplifying a plurality of extension products. Primer extension reactions can involve changes in temperature (thermocycling) or a constant temperature (isothermal). In some embodiments, primer extension reactions comprise polymerase chain reaction (PCR). PCR typically involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred μL, e.g. 200 μL. Examples of polymerase enzymes that can be used for PCR are thermostable polymerases, including but not limited to, *Thermus thermophilus* HB8; mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some embodiments, a hot start polymerase is used. A hot start polymerase is a modified form of a DNA Polymerase that requires thermal activation. Such a polymerase can be used, for example, to further increase sensitivity, specificity, and yield; and/or to further improve low copy target amplification. Typically, the hot start enzyme is provided in an inactive state. Upon thermal activation the modification or modifier is released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Mirus Bio; USB Corp.; Yorkshire Bioscience Ltd; and the like.

In some embodiments, primer extension and amplification reactions comprise isothermal reactions. Non-limiting examples of isothermal amplification technologies are ligase chain reaction (LCR) (e.g., U.S. Pat. Nos. 5,494,810 and 5,830,711); transcription mediated amplification (TMA) (e.g., U.S. Pat. Nos. 5,399,491, 5,888,779, 5,705,365, 5,710,029); nucleic acid sequence-based amplification (NASBA) (e.g., Malek et al., U.S. Pat. No. 5,130,238); signal mediated amplification of RNA technology (SMART) (e.g., Wharam et al., Nucleic Acids Res. 2001, 29, e54); strand displacement amplification (SDA) (e.g., U.S. Pat. No. 5,455,166); thermophilic SDA (Spargo et al., Mol Cell Probes 1996, 10:247-256; European Pat. No. 0684315; rolling circle amplification (RCA) (e.g., Lizardi, "Rolling Circle Replication Reporter Systems," U.S. Pat. No. 5,854,033); loop-mediated isothermal amplification of DNA (LAMP) (e.g., Notonii et al., "Process for Synthesizing Nucleic Acid," U.S. Pat. No. 6,410,278); helicase-dependent amplification (HDA) (e.g., U.S. Pat. Appl. US 20040058378); single primer isothermal amplification (SPIA) (e.g., WO2001020035 and U.S. Pat. No. 6,251,639); and circular helicase-dependent amplification (cHDA) (e.g., U.S. patent application Ser. No. 10/594,095).

In some embodiments, primer extension reactions are effected by polymerases having strand-displacement activity, such as for RCA. In some embodiments, isothermal amplification comprises rolling circle amplification (RCA). A RCA reaction mixture can comprise one or more primers, a polymerase having strand displacement activity, and dNTPs. Strand displacement refers to the ability to displace down-stream DNA during synthesis. Polymerases having strand-displacement activity may have varying degrees of strand displacement activity. In some embodiments, a polymerase may have weak or no strand-displacement activity. In some embodiments, polymerases may have strong strand displacement activity. In some embodiments, polymerases with strand displacement activity may have different levels of strand-displacement activity at different reaction temperatures. In some embodiments, a polymerase may display strand displacement activity at moderate temperatures, e.g., 20° C.-37° C. In some embodiments, a polymerase may display strand displacement activity at elevated temperatures, e.g., 65° C. Reaction temperatures can be adjusted to favor a level of activity of a polymerase having strand-displacement activity. In some embodiments, a reaction temperature is at least 20° C., 25° C., 30° C., 35° C., 40° C., 45° C., 50° C., 55° C., 60° C., 65° C., 70° C., 75° C., 80° C., 85° C., or 90° C. In some embodiments, a reaction temperature is between 20° C. and 80° C. In some embodiments, a reaction temperature is between 20° C. and 70° C. In some embodiments, a reaction temperature is between 20° C. and 60° C. In some embodiments, a reaction temperature is between 20° C. and 50° C. In some embodiments, various reaction temperatures can be cycled through in different stages to increase or decrease the strand displacement activity of a polymerase. Non-limiting examples of polymerases having strand displacement activity include Bst DNA polymerase, large fragment; Bsu DNA polymerase, large fragment; Deep VentRTM DNA polymerase; Deep VentRTM (exo-) DNA polymerase; Klenow fragment (3'-5' exo-); DNA polymerase I, large fragment; M-MuLV reverse transcriptase; phi29 DNA polymerase; VentR® DNA polymerase; and VentR® (exo-) DNA polymerase.

Concatemers and Sequencing

Concatemers generated as products of amplification reactions, including thermocycling methods, isothermal methods, and combinations of these, can comprise two or more copies of a target polynucleotide. A concatemer may comprise about 2, 3, 4, 5, 6, 7, 8, 9, 10 or more copies of the target polynucleotide. In some embodiments, concatemers are generated as products of primer extension reactions from a plurality of target polynucleotides, wherein constituents of the plurality are non-uniform in length and comprise a plurality of sequences.

In some embodiments of any of the various aspects of the disclosure, a primer may comprise one or more portions. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof. In some embodiments, a primer such as a third primer comprises a sequencing adapter element (herein also referred to as an adaptor), which generally refers to oligonucleotides incorporated at the 5' and/or 3' ends of polynucleotides to facilitate one or more steps of a polynucleotide sequencing reaction. In some embodiments, a sequencing adapter is used to bind a polynucleotide comprising the sequencing adapter to a flow cell for next generation sequencing. Non-limiting examples of next-generation sequencing methods are single-molecule real-time sequencing, ion semiconductor sequencing, pyrosequencing, sequencing by synthesis, sequencing by ligation, and chain termination. Sequencing adapters for flow cell attachment may comprise any suitable sequence compatible with next generation sequencing systems, e.g., 454 Sequencing, Ion Torrent Proton or PGM, and Illumina X10. Non-limiting examples of sequencing adapters for next generation sequencing methods include P5 and P7 adapters suitable for use with Illumina sequencing systems; TruSeq Universal Adapter; and TruSeq Indexed Adapter. In some embodiments, a sequencing adapter can be used to enrich, e.g., via amplification, such as polymerase chain reaction (PCR), for polynucleotides comprising the adapter sequence. Sequencing adapters can further comprise a barcode sequence and/or a sample index sequence.

Certain embodiments of the present disclosure comprise sequencing a plurality of amplicons. A variety of sequencing methodologies are available for sequencing the plurality of amplicons. In some embodiments, high-throughput sequencing methodologies are used. Non-limiting examples of sequencing methodologies that can be used include sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300 nucleotides or more in length. In some embodiments, sequencing comprises a sequencing-by-synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In certain embodiments of any of the various aspects of the present disclosure, amplicons are purified prior to sequencing. Amplicons can be purified by various methods. Amplicons may be purified to remove excess or unwanted reagents, reactants, or products. Amplicons may further be purified by size, sequence, or other physical or chemical characteristic. In some embodiments, amplicons may be subjected to size exclusion chromatography, whereby amplicons comprising only one copy of the target polynucleotide and/or small reagents (e.g., primers) are retained and discarded, or amplicons comprising two or more copies of the target polynucleotide are retained and released in a separate volume. In some embodiments, amplicons may be subjected to fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp). In some embodiments, amplification products are treated to filter the resulting amplicons on the basis of size to reduce and/or eliminate the number of monomers in a mixture comprising concatemers. This can be done using any purification technique as described elsewhere herein.

Sequence Variants

In some embodiments, the amplicons are sequenced to detect a sequence variant, e.g., inversion, deletion, duplication, translocation, single base changes, and rare somatic mutations, with respect to a reference sequence or in a background of no mutations. In some embodiments, the sequence variant is correlated with disease. In some embodiments, the sequence variant is not correlated with disease. In general, sequence variants for which there is statistical, biological, and/or functional evidence of association with a disease or trait are referred to as "causal genetic variants." A single causal genetic variant can be associated with more than one disease or trait. In some cases, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Additional non-limiting examples of causal genetic variants are described in WO2014015084. Additional non-limiting examples of methods for the identification of rare sequence variants are described in WO2015089333.

Sequence Analysis and Base Calling

According to some embodiments, a sequence difference between sequencing reads and a reference sequence is called as a genuine sequence variant (e.g. existing in the sample prior to amplification or sequencing, and not a result of either of these processes) if it occurs in at least two different polynucleotides (e.g. originating from two different circular polynucleotides, which can be distinguished as a result of having different junctions). Because sequence variants that are the result of amplification or sequencing errors are unlikely to be duplicated exactly (e.g. position and type) on two different polynucleotides comprising the same target sequence, adding this validation parameter greatly reduces the background of erroneous sequence variants, with a concurrent increase in the sensitivity and accuracy of detecting actual sequence variation in a sample. In some embodiments, a sequence variant having a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate call. In some embodiments, the sequence variant occurs with a frequency of about or less than about 0.1%. In some embodiments, the frequency of a sequence variant is sufficiently above background when such frequency is statistically significantly above the background error rate (e.g. with a p-value of about or less than about 0.05, 0.01, 0.001, 0.0001, or lower). In some embodiments, the frequency of a sequence variant is sufficiently above background when such frequency is about or at least about 2-fold, 3-fold, 4-fold, 5-fold, 6-fold, 7-fold, 8-fold, 9-fold, 10-fold, 25-fold, 50-fold, 100-fold, or more above the background error rate (e.g. at least 5-fold higher). In some embodiments, the background error rate in accurately determining the sequence at a given position is about or less than about 1%, 0.5%, 0.1%, 0.05%, 0.01%, 0.005%, 0.001%, 0.0005%, or lower. In some embodiments, the error rate is lower than 0.001%. In some embodiments, additional or alternative verification steps are used in distinguishing sequence differences that result from sample processing, from true sequence variants. Examples of such validation steps are provided herein, such as with regard to any of the various aspects of the present disclosure, including comparison between differentially tagged complementary strands from a single double-stranded sample molecule.

In some embodiments, identifying a genuine sequence variant (also referred to as "calling" or "making a call") comprises optimally aligning one or more sequencing reads with a reference sequence to identify differences between the two, as well as to identify junctions. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as from a reference genome or from a consensus generated from sequencing reads under analysis.

Typically, the sequencing data is acquired from large scale, parallel sequencing reactions. Many of the next generation high-throughput sequencing systems export data as FASTQ files, although other formats may be used. In some embodiments, sequences are analyzed to identify repeat unit length (e.g. the monomer length), the junction formed by circularization, and any true variation with respect to a reference sequence, typically through sequence alignment. Identifying the repeat unit length can include computing the regions of the repeated units, finding the reference loci of the sequences (e.g. when one or more sequences are particularly targeted for amplification, enrichment, and/or sequencing), the boundaries of each repeated region, and/or the number of repeats within each sequencing read. In some embodiments, a sequence variant may be considered a confirmed, or genuine, variant if it occurs in more than one repeated unit of the same polynucleotide, as the same sequence variation is likewise unlikely to occur at the same position in a repeated target sequence within the same concatemer. The quality score of a sequence may be considered in identifying variants and confirmed variants, for example, the sequence and bases with quality scores lower than a threshold may be filtered out. Sequence analysis can also include analyzing sequence data for both strands of a duplex. As noted above, in some embodiments, an identical variant that appears in the sequences of reads from different polynucleotides from the sample (e.g. circularized polynucleotides having different junctions) is considered a confirmed variant. Other bioinformatics methods can be used to further increase the sensitivity and specificity of the variant calls.

In some embodiments, statistical analyses may be applied to determination of variants (mutations) and quantitate the ratio of the variant in total DNA samples. Total measurement of a particular base can be calculated using the sequencing data. For example, from the alignment results calculated in previous steps, one can calculate the number of "effective reads," that is, number of confirmed reads for each locus. The allele frequency of a variant can be normalized by the effective read count for the locus. The overall noise level, that is the average rate of observed variants across all loci, can be computed. The frequency of a variant and the overall noise level, combined with other factors, can be used to determine the confidence interval of the variant call. Statistical models such as Poisson distributions can be used to assess the confidence interval of the variant calls. The allele frequency of variants can also be used as an indicator of the relative quantity of the variant in the total sample.

EXAMPLES

The following examples are given for the purpose of illustrating various embodiments of the disclosure and are not meant to limit the present disclosure in any fashion. The present examples are exemplary and are not intended as limitations on the scope of the disclosure. Changes therein and other uses will occur to those skilled in the art.

Example 1

Identification of Two Strands of Double-Stranded DNA Molecules Using 3' Labeling and Rolling Circle Amplification (RCA)

Figure 6:
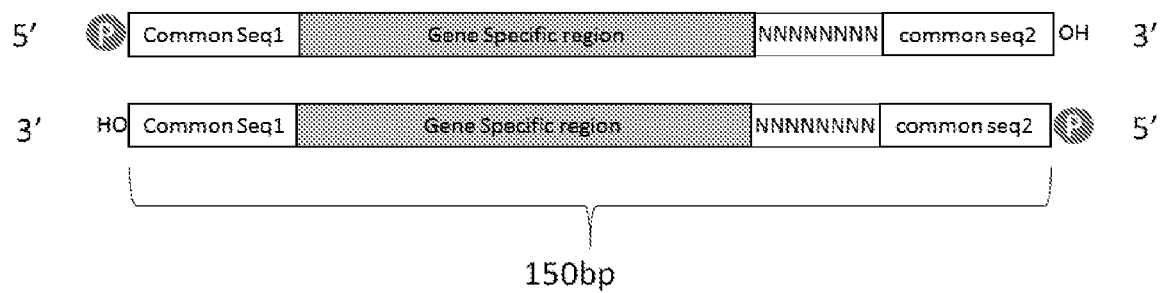
FIG. 6 provides a schematic illustration of the synthetic test DNA construct used in Examples 1 and 2.

To demonstrate the ability to identify two strands of a double-stranded DNA molecule using 3' end labeling methods provided herein, a synthetic test DNA construct 150 bp in length was synthesized. The synthetic DNA construct contains an eight-base random barcode (denoted by 'NNNNNNNN'), gene specific primer binding sites, and common primer binding sites (common seq 1 and common seq 2) for amplification as illustrated in FIG. 6. Concentration of the synthetic DNA construct was determined by ddPCR.

The DNA construct was mixed with a 20 ng/μl carrier DNA stock at 100 molecule/μl concentration based on ddPCR quantification. For 3' end labeling, 5 μl of NEBNext dA-tailing reaction buffer and 3 μl of Klenow fragment (3'→5' exo-) was added to 20 ng of the mixed DNA sample. The final volume was 50 μl. The reaction was incubated at 37° C. for 30 minutes before spin column purification using 0.9× AMPure XP beads.

The dA-tailed DNA sample was then ligated to form circular target polynucleotides. For ligation, 12 μl of purified DNA fragments was denatured by heating at 95° C. for 30 seconds and chilling on ice for 2 minutes. Then, 8 μl of ligation mix containing 2 μl of 10x CircLigase buffer, 4 μl of 5M Betaine, 1 μl of 50mM MnCl$_2$, and 1 μl of CircLigase II was added to the denatured DNA samples and the reactions were incubated at 60° C. for at least 3 hours. Linear single-stranded DNA molecules not circularized were removed by an exonuclease treatment step. For exonuclease treatment, ligation products were heated at 80° C. for 45 seconds and then 1 μl of exonuclease mix (ExoI 20U/μl: ExoIII 100U/μl, at a 1:2 ratio) was added to the sample. The sample was incubated on a thermal cycler at 37° C. for 30 minutes and then at 80° C. for 20 minutes. After exonuclease treatment, 1 μl of 50mM EDTA was added to each tube.

Circular target polynucleotides were then subjected to rolling circle amplification (RCA). For each reaction, 0.34 ul of 1M Tris-HCl (pH 9.2), 1 μl of 100 mM MgSO$_4$, 2.78 μl of 180 mM (NH$_4$)$_2$SO$_4$, 0.75 uL of dNTP mix (25 mM each), 0.5 μl of 10% Tween 20, 1.20 μl of 1M KCl, 2 μl of 10 μM back-to-back forward and reverse primers binding the gene specific primer binding sites, and 18.28 μl of water was added to each 10 ng of DNA samples. The reactions were heated at 80° C. for 1 minute and incubated at 63° C. for 5 minutes before cooling down to 4° C. Next, 15 units of Bst 2.0 warm start DNA polymerase was added to each reaction. The reaction was incubated in a thermal cycler with the following program: 8 cycles of 60° C. for 30 seconds; 70° C. for 4.5 minutes; 94° C. for 20 seconds; and 58° C. for 10 seconds. At the end of every two cycles, 15 units of Bst 2.0 warm start DNA polymerase was added.

All amplification products were purified by addition of 50 μl AMPure beads, following the manufacturer's instructions for the remaining wash steps. For elution, 55 μl of elution buffer was added to each tube and the beads were incubated at 65° C. for 5 minutes. After spinning briefly, the tubes were returned to the magnets. About 50 μl of eluted product was recovered from each reaction.

Each 50 μl of eluent was mixed with 5.7 μl of 10× AccuPrime buffer, 1 μl of 25 μM adaptor primers that were complementary to common sequences at the 3' end of the primers used in RCA, and 2 units of AccuPrime HiFi Taq polymerase. Adaptors were attached by amplification using the following PCR program: 95° C. for 2 minutes; 20 cycles of 95° C. for 30 seconds, 60° C. for 30 seconds, 72° C. for 2.5 minutes; and final extension at 72° C. for 7 minutes. PCR amplified library products were analyzed by agarose gel and products in size range 550 bp-1000 bp were further collected for sequencing. The resulting amplification products sequenced.

For bioinformatics analysis on sequencing data, FASTQ files were obtained from a HiSeq run. The FASTQ files were aligned to a reference file containing the DNA construct sequence to identify the target of interest. Reads containing the specific DNA construct sequence with the same 8-base barcode sequence were grouped together. The last base at the end of the DNA construct sequence was identified as either A or T, indicating forward or reverse strands of the same double-stranded molecule. For two replicate experiments, Table 1 provides the number of unique barcodes observed in the sequencing data, the number of unique barcodes with either an A- or T-tail (e.g., forward or reverse strand), end labeling efficiency (calculated as the ratio of the number of unique barcodes with either an A- or T-tail to the number of unique barcodes observed), the number of unique barcodes for which both forward and reverse strands (e.g., A-tailed and T-tailed) were detected, and a corresponding double-strand confirmation ratio.

TABLE 1

| Experiment | Number of Unique Barcodes Observed | Unique Barcodes With Either A- or T-Tail (e.g., end labeled) | End Labeling Efficiency | Unique Barcodes With Complementary Strands Identified | Confirm Ratio |
|---|---|---|---|---|---|
| Replicate 1 | 66 | 62 | 94% | 28 | 42% |
| Replicate 2 | 60 | 58 | 97% | 23 | 38% |

Example 2

Identification of Two Strands of Double-Stranded DNA Molecules Through Partitioning To demonstrate the ability to identify two strands of a double-stranded DNA molecule by separating complementary strands into individual reaction volumes as described for embodiments of methods provided herein, a synthetic test DNA construct containing an eight-base random barcode (denoted by 'NNNNNNNN'), gene specific primer binding sites, and common primer binding sites for amplification (common seq 1 and common seq 2), illustrated schematically in FIG. 6, was synthesized. Concentration of the DNA construct was determined by ddPCR.

The DNA construct was mixed with a 20 ng/µl carrier DNA stock at 100 molecule/µl concentration based on ddPCR quantification. The mixed DNA sample was then ligated to form circular target polynucleotides. For ligation, 20 ng of DNA fragments was denatured by heating at 95° C. for 30 seconds and chilling on ice for 2 minutes. Then, 8 µl of ligation mix containing 2 of 10× CircLigase buffer, 4 µl of 5M Betaine, 1 µl of 50 mM MnCl$_2$, and 1 µl of CircLigase II was added to the denatured DNA samples and the reactions were incubated at 60° C. for at least 3 hours. Linear single-stranded DNA molecules not circularized were removed by an exonuclease treatment step. For exonuclease treatment, ligation products were heated at 80° C. for 45 seconds and then 1 µl of exonuclease mix (ExoI 20U/µl: ExoIII 100U/µl, at a 1:2 ratio) was added to the sample. The sample was incubated on a thermal cycler at 37° C. for 30 minutes and then at 80° C. for 20 minutes. After exonuclease treatment, 1 µl of 50 mM EDTA was added to each tube.

Ligation products were split into 4 wells before rolling circle amplification (RCA). 0.34 uL of 1M Tris-HCl (pH 9.2), 1 µl of 100 mM MgSO$_4$, 2.78 µl of 180 mM (NH$_4$)$_2$SO$_4$, 0.75 uL of dNTP mix (25 mM each), 0.5 µl of 10% Tween 20, 1.20 µl of 1M KCl, and 2 µl of 10 µM back-to-back forward and reverse primers binding the gene specific primer binding sites and water was added to make the total volume 50 uL in each well. The reactions were heated at 80° C. for 1 minute and incubated at 63° C. for 5 minutes before cooling down to 4° C. Next, 15 units of Bst 2.0 warm start DNA polymerase was added to each reaction. The reaction was incubated in a thermal cycler with the following program: 8 cycles of 60° C. for 30 seconds; 70° C. for 4.5 minutes; 94° C. for 20 seconds; and 58° C. for 10 seconds. At the end of every two cycles, 15 units of Bst 2.0 warm start DNA polymerase was added.

All amplification products were purified by addition of 50 µl AMPure beads, following the manufacturer's instructions for the remaining wash steps. For elution, 55 µl of elution buffer was added to each tube and the beads were incubated at 65° C. for 5 minutes. After spinning briefly, the tubes were returned to the magnets. About 50 µl of eluted product was recovered from each reaction.

Each 50 µl of eluent was mixed with 5.7 µl of 10× AccuPrime buffer, 1 µl of 25 µM adaptor primers that were complementary to common sequences at the 3' end of the primers used in RCA, and 2 units of AccuPrime HiFi Taq polymerase. Adaptors were attached by amplification using the following PCR program: 95° C. for 2 minutes; 20 cycles of 95° C. for 30 seconds, 60° C. for 30 seconds, 72° C. for 2.5 minutes; and final extension at 72° C. for 7 minutes. PCR amplified library products were analyzed by agarose gel and products in size range 550 bp-1000 bp were further collected for sequencing. The resulting amplification products were sequenced.

For bioinformatics analysis on sequencing data, FASTQ files were obtained from a HiSeq run. The FASTQ files were aligned to a reference file containing the DNA construct sequence to identify the targets. Reads containing a specific DNA construct sequence with the same 8-base barcode sequence were grouped together. Table 2 provides the number of unique barcodes observed in the sequencing data, the number of unique barcodes detected in two of the four independent wells (e.g., complementary strands split into two independent wells), and a corresponding confirmation ratio.

TABLE 2

| Experiment | Number of Unique Barcodes Observed | Unique Barcodes detected in two independent wells | Confirm Ratio |
|---|---|---|---|
| Replicate-1 | 85 | 41 | 48% |
| Replicate-2 | 98 | 35 | 36% |

The invention claimed is:

1. A method of identifying complementary strands in a nucleic acid sample comprising a plurality of double-stranded polynucleotides, each double-stranded polynucleotide of the plurality comprising a first complementary strand and a second complementary strand, each having a 5' end and a 3' end, the method comprising:
   (a) modifying a polynucleotide sequence of at least one of a first complementary strand and a second complementary strand of individual double-stranded polynucleotides by adding one or more predetermined nucleotides in a base by base manner to the 3' end of at least one of the first complementary strand and the second complementary strand;
   (b) circularizing a plurality of first complementary strands and a plurality of second complementary strands to form a plurality of single stranded polynucleotide circles, the one or more predetermined nucleotides defining a boundary between 3' sequences and 5' sequences of each single stranded polynucleotide circle;
   (c) amplifying by rolling circle amplification the single stranded polynucleotide circles to form a plurality of concatemers;
   (d) sequencing said plurality of concatemers, to yield a plurality of sequencing reads; and
   (e) identifying from the plurality of sequencing reads, a given first complementary strand and a given second complementary strand as originating from a common double-stranded polynucleotide based on (i) sequences of the respective 3' ends and 5' ends adjacent to the one or more predetermined nucleotides, and (ii) sequences of the one or more predetermined nucleotides.

2. The method of claim 1, wherein modifying a polynucleotide sequence further comprises attaching a polynucleotide having a predefined polynucleotide sequence to a 5' end, a 3' end, or both 5' and 3' ends of at least one of the first complementary strand and the second complementary strand or altering at least one nucleotide of the polynucleotide sequence.

3. The method of claim 2, wherein modifying the polynucleotide sequence comprises altering at least one nucleotide of the polynucleotide sequence, and altering at least one nucleotide of the polynucleotide sequence is effected by treatment with bisulfite.

4. The method of claim 1, further comprising identifying two first complementary strands or two second complementary strands as originating from different double-stranded polynucleotides based on extension of the respective 3' ends by a different number of predetermined nucleotides.

5. The method of claim 4, wherein the step of amplifying the extended polynucleotides comprises extending a primer hybridized to an adaptor polynucleotide.

6. The method of claim 1, wherein circularizing is effected by subjecting the extended polynucleotides to a ligation reaction.

7. The method of claim 1, wherein the polynucleotides are denatured to form single-stranded polynucleotides prior to circularization.

8. The method of claim 1, wherein amplification produces linear concatemers, and further wherein each concatemer comprises more than one copy of the corresponding circularized polynucleotide, or a complement thereof.

9. The method of claim 1, wherein the amplifying comprises extension of random primers.

10. The method of claim 1, wherein the primers comprise a tag sequence, a sequencing primer binding sequence, or both.

11. The method of claim 1, wherein the amplifying comprises extension of one or more primers specific to a target sequence.

12. A method of identifying a sequence variant in a nucleic acid sample comprising a plurality of double-stranded polynucleotides, each double-stranded polynucleotide of the plurality comprising a first complementary strand and a second complementary strand, each having a 5' end and a 3' end, the method comprising:
   (a) modifying a polynucleotide sequence of at least one of a first complementary strand and a second complementary strand of individual double-stranded polynucleotides by adding one or more predetermined nucleotides in a base by base manner to the 3' end of at least one of the first complementary strand and the second complementary strand;
   (b) circularizing a plurality of first complementary strands and a plurality of second complementary strands to form a plurality of single stranded polynucleotide circles, the one or more predetermined nucleotides defining a boundary between 3' sequences and 5' sequences of each single stranded polynucleotide circle;
   (c) amplifying by rolling circle amplification the single stranded polynucleotide circles to form a plurality of concatemers;
   (d) sequencing a plurality of first complementary strands and a plurality of second complementary strands, or amplification products thereof, to yield a plurality of sequencing reads;
   (e) identifying from the plurality of sequencing reads, a given first complementary strand and a given second complementary strand as originating from a common double-stranded polynucleotide based on (i) sequences of the respective 3' end and 5' ends adjacent to the one or more predetermined nucleotides, and (ii) sequences of the one or more predetermined nucleotides;
   (f) comparing polynucleotide sequences of the given first complementary strand and the given second complementary strand originating from the common double-stranded polynucleotide; and
   (g) calling a sequence difference in the given first complementary strand relative to a reference sequence as the sequence variant only when the given second complementary strand originating from the common double-stranded polynucleotide comprises a complement of the sequence difference.

13. The method of claim 12, wherein modifying a polynucleotide sequence further comprises attaching a polynucleotide having a predefined polynucleotide sequence to a 5' end, a 3' end, or both 5' and 3' ends of at least one of the first complementary strand and the second complementary strand or altering at least one nucleotide of the polynucleotide sequence.

14. The method of claim 13, wherein modifying the polynucleotide sequence comprises altering at least one nucleotide of the polynucleotide sequence, and altering at least one nucleotide of the polynucleotide sequence is effected by treatment with bisulfite.

15. The method of claim 12, further comprising joining an adaptor polynucleotide to the 3' end of: (i) one or both strands of the double-stranded polynucleotides; or (ii) the extended polynucleotides.

16. The method of claim 12, wherein amplification produces linear concatemers, and further wherein each concatemer comprises more than one copy of the corresponding circularized polynucleotide, or a complement thereof.

* * * * *